(12) United States Patent
Kita et al.

(10) Patent No.: US 9,991,453 B2
(45) Date of Patent: *Jun. 5, 2018

(54) ELECTRONIC DEVICE, ORGANIC ELECTROLUMINESCENT ELEMENT, ORGANIC THIN-FILM SOLAR CELL, AND DYE-SENSITIZED SOLAR CELL

(71) Applicant: Konica Minolta, Inc., Tokyo (JP)

(72) Inventors: Hiroshi Kita, Hachioji (JP); Tatsuo Tanaka, Fuchu (JP); Rie Katakura, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/888,295

(22) PCT Filed: May 21, 2014

(86) PCT No.: PCT/JP2014/063449
§ 371 (c)(1),
(2) Date: Oct. 30, 2015

(87) PCT Pub. No.: WO2014/189072
PCT Pub. Date: Nov. 27, 2014

(65) Prior Publication Data
US 2016/0079548 A1    Mar. 17, 2016

(30) Foreign Application Priority Data

May 22, 2013   (JP) ................................ 2013-107556

(51) Int. Cl.
*H01L 51/00*    (2006.01)
*C07F 15/00*    (2006.01)
(Continued)

(52) U.S. Cl.
CPC ...... *H01L 51/0084* (2013.01); *C07F 15/0033* (2013.01); *C09K 11/06* (2013.01);
(Continued)

(58) Field of Classification Search
None
See application file for complete search history.

(56) References Cited

U.S. PATENT DOCUMENTS 7,807,992 B2   10/2010  Wang
2004/0105614 A1*  6/2004  Kobayashi ............ G02F 1/1354
                                                385/16

(Continued)

FOREIGN PATENT DOCUMENTS

JP   2001271061 A   10/2001
JP   2002163926 A    6/2002
(Continued)

OTHER PUBLICATIONS

International Search Report; International Application No. PCT/JP2014063449; International filing date: May 21, 2014; Applicant: Konica Minolta, Inc.; total of 3 pages; English Translation of International Search Report; total of 3 pages; Grand total of 6 pages.

(Continued)

*Primary Examiner* — Katie L Hammer
(74) *Attorney, Agent, or Firm* — Lucas & Mercanti, LLP

(57) ABSTRACT

This invention addresses the problem of providing an electronic device, organic electroluminescent device, conductive film, organic thin-film solar cell, and dye-sensitized solar cell provided with a charge-transporting thin film that exhibits excellent stability. In the presence of external disturbances, the charge-transporting thin film exhibits little in the way of fluctuations, and the resistance of the charge-transporting thin film changes little over time as current is supplied. As one of the secondary effects thereof, the charge- (Continued)

transporting thin film results in little in the way of changes in emission characteristics over time. This electronic device, which is provided with a charge-transporting thin film that contains one or more functional organic compounds having chiral elements, is characterized by the provision of a charge-transporting thin film wherein the total of the number of chiral elements per molecule in each type of the functional organic compounds summed over all types of the functional organic compounds is four or more.

16 Claims, 13 Drawing Sheets

(51) Int. Cl.

| | | |
|---|---|---|
| *C09K 11/06* | (2006.01) | |
| *H01B 1/12* | (2006.01) | |
| *C09K 11/08* | (2006.01) | |
| *H05B 33/20* | (2006.01) | |
| *H01L 51/42* | (2006.01) | |
| *H01L 51/50* | (2006.01) | |
| *H05B 33/14* | (2006.01) | |

(52) U.S. Cl.
CPC ........... *H01B 1/12* (2013.01); *H01L 51/0085* (2013.01); *H01L 51/4226* (2013.01); *H01L 51/4253* (2013.01); *H01L 51/5016* (2013.01); *H01L 51/5056* (2013.01); *H05B 33/20* (2013.01); *C09K 2211/1007* (2013.01); *C09K 2211/1011* (2013.01); *C09K 2211/1029* (2013.01); *C09K 2211/1037* (2013.01); *C09K 2211/1044* (2013.01); *C09K 2211/1074* (2013.01); *C09K 2211/1088* (2013.01); *C09K 2211/1092* (2013.01); *C09K 2211/185* (2013.01); *H01L 51/006* (2013.01); *H01L 51/0036* (2013.01); *H01L 51/0043* (2013.01); *H01L 51/0047* (2013.01); *H01L 51/0052* (2013.01); *H01L 51/0054* (2013.01); *H01L 51/0059* (2013.01); *H01L 51/0067* (2013.01); *H01L 51/0072* (2013.01); *H01L 51/0073* (2013.01); *H01L 51/0074* (2013.01); *H01L 51/0081* (2013.01); *H01L 51/5012* (2013.01); *H05B 33/14* (2013.01); *Y02E 10/542* (2013.01); *Y02E 10/549* (2013.01)

(56) References Cited

U.S. PATENT DOCUMENTS

| | | | | |
|---|---|---|---|---|
| 2006/0008673 | A1* | 1/2006 | Kwong | C07F 15/0033 |
| | | | | 428/690 |
| 2009/0072712 | A1* | 3/2009 | Stoessel | C09K 11/06 |
| | | | | 313/504 |
| 2010/0141125 | A1 | 6/2010 | Otsu et al. | |
| 2011/0057559 | A1 | 3/2011 | Xia et al. | |
| 2011/0309307 | A1* | 12/2011 | Zeika | C07D 497/04 |
| | | | | 252/500 |
| 2012/0186652 | A1 | 7/2012 | Pan | |
| 2012/0248419 | A1* | 10/2012 | Thompson | B82Y 10/00 |
| | | | | 257/40 |

FOREIGN PATENT DOCUMENTS

| | | | |
|---|---|---|---|
| JP | 2006342318 | A | 12/2006 |
| JP | 4110160 | B2 | 4/2008 |
| JP | 2008112976 | A | 5/2008 |
| JP | 2008525995 | A | 7/2008 |
| KR | 10-2007-0083986 | A | 8/2007 |
| KR | 10-2012-0089376 | A | 8/2012 |
| WO | 2008/096239 | A1 | 8/2008 |

OTHER PUBLICATIONS

International Search Report dated Aug. 5, 2014 for Application No. PCT/JP2014/063449 and English translation.
Office Action dated Jun. 20, 2017 from corresponding Korean Patent Application No. 10-2015-7032891 and English translation.
Extended European Search Report dated Dec. 16, 2016 from the corresponding European Application No./ Patent No. 14800515.0-1555 / 3001475 PCT/JP2014063449; Applicant: Konica Minolta, Inc.; Total of 9 pages.

* cited by examiner

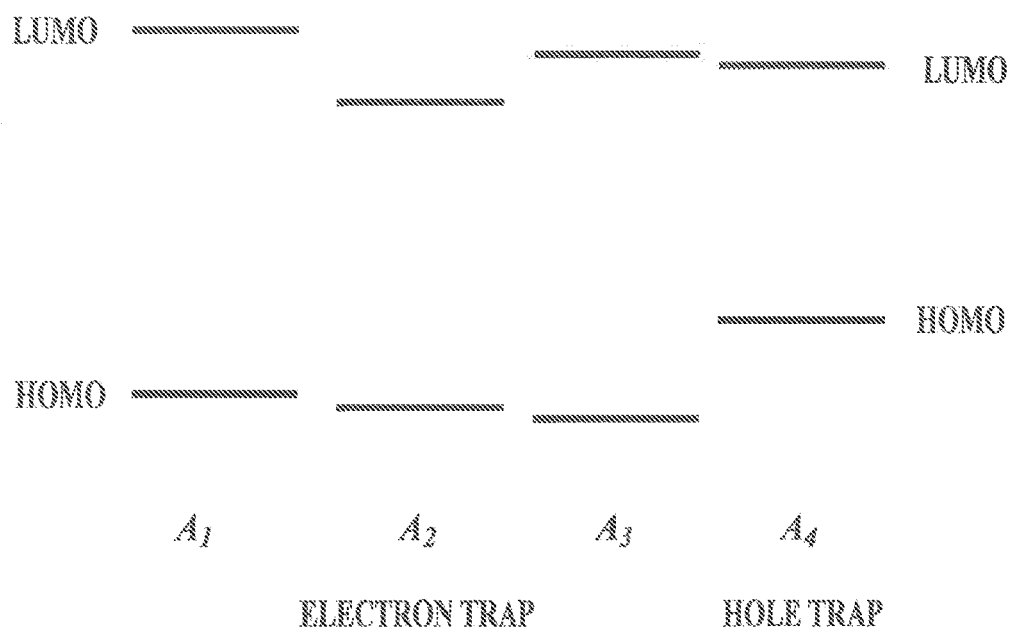
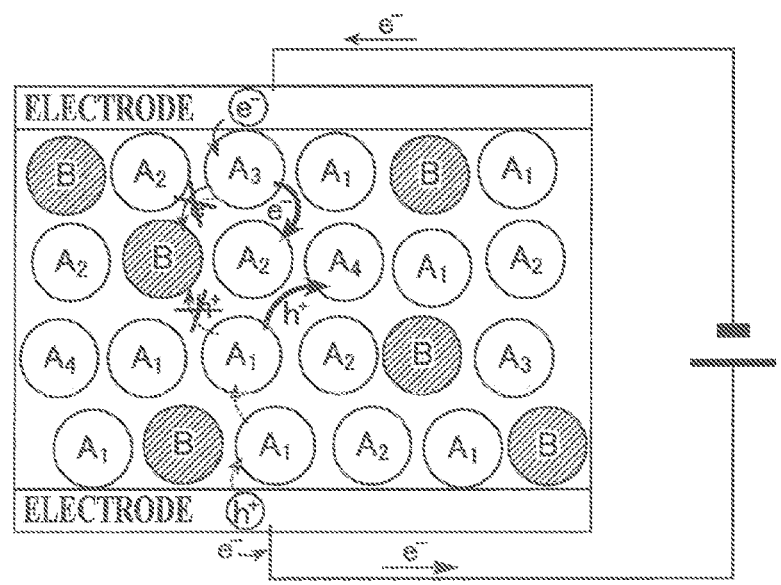

LIGHT

LIGHT

US 9,991,453 B2

ELECTRONIC DEVICE, ORGANIC ELECTROLUMINESCENT ELEMENT, ORGANIC THIN-FILM SOLAR CELL, AND DYE-SENSITIZED SOLAR CELL

CROSS REFERENCE TO RELATED APPLICATION

This Application is a 371 of PCT/JP2014/063449 filed on May 21, 2014, which, in turn, claimed the priority of Japanese Patent Application No. JP2013-107556 filed on May 22, 2013, both applications are incorporated herein by reference.

TECHNICAL FIELD

The present invention relates to an electronic device, an organic electroluminescent element, an electrically conductive film, an organic thin-film solar cell, and a dye-sensitized solar cell which have high stability.

BACKGROUND ART

Electronic devices to which an electric field is applied, such as organic electroluminescent elements (hereinafter, also referred to as "organic EL elements"), solar cells, and organic transistors, generally include charge-transporting thin films containing organic materials capable of transporting charge carriers (generic terms including electrons and holes) during application of electric fields. Various properties are required for functional organic materials contained in charge-transporting thin films, and such functional organic materials have been extensively developed in recent years.

Industrial components made of organic materials, particularly electronic devices and electronic components to which a high electric field is applied, generally involve problems due to the nature of the organic materials used therein, i.e. thermal degradation and electrochemical deterioration that are characteristics of organic substances. Most of technical improvements have been directed to enhance the robustness of such organic materials per se. For example, organic materials, such as copper phthalocyanine complexes, have been traditionally used in industrial applications. They are dyes, but have characteristics like those of pigments; they have a rigid chemical structure which renders them insoluble to any solvent, unlike other organic materials. The use of such organic materials unfortunately fails to exploit properties common organic materials have, such as solubility, flexibility, chemical reactivity, and compatibility with other materials. Such characteristics of organic materials are inappropriate for future industrial applications.

Organic materials are barely used in the form of a single isolated molecule in usual cases. They are often present in the form of an aggregate composed of a single type or different types of molecules (including different materials, such as metals or inorganic substances).

Meanwhile, molecular design has been essentially based on data of an isolated single molecule, typically data of structural analysis by X-ray diffractometry and molecular orbital calculation. In the actual circumstances, the way of molecular design has not been very active in view of the coexistence of multiple molecules. A technique has been therefore desired which focuses on the aggregates formed of molecules, to improve the stability of the aggregates at macroscopic level.

If no change occurs in a film or an article containing an organic material during preservation or use, its properties should not change in any way. Properties required for such a film or article may vary depending on its application field. Examples of the required properties include a specific color, charge transfer properties, and optical properties such as a specific refractive index. In any case, if the film or the article experience no change in its condition, its properties should not change in any way, that is, it should have infinite durability.

For example, charge-transporting thin films require continuous application of an electric field during use. Thus, they should have sufficient durability over time during application of current. In particular, they should not show unfavorable variations in charge transfer characteristics, i.e. variations in resistance, in view of their intended purpose of use. A charge-transporting thin film is therefore desired which shows a small change in resistance during the application of current.

Disclosed conventional techniques of improving the stability of the thin film rely on use of various compounds alone or in combination. For example, PTL 1 discloses a metal complex having a specific ligand as a blue phosphorescent compound. Some reports also disclose that combined use of two dopants which emit light of similar colors provide a device with higher efficiency, a prolonged lifetime, and a lower driving voltage (see, for example, PTLs 2, 3 and 4).

Unfortunately, even such techniques fail to achieve sufficient stability required for charge-transporting thin films, where a current is generally applied for a long time, under conditions expected in the market. There has been therefore need for a radical solution to such a problem.

RELATED ART DOCUMENTS

Patent Documents

PTL 1: U. S. Patent Application Publication No. 2011/0057559
PTL 2: Japanese Patent Application Laid-Open Publication No. 2008-112976
PTL 3: Japanese Patent No. 4110160
PTL 4: U.S. Pat. No. 7,807,992

SUMMARY OF THE INVENTION

Problems to be Solved by the Invention

An object of the invention, which has been accomplished under such circumstances, is to provide an electronic device, an organic electroluminescent element, an electrically conductive film, an organic thin-film solar cell, and a dye-sensitized solar cell, which include a very stable charge-transporting thin film with small variations in properties due to disturbance and small variations in resistance over time during application of current. The invention further provides a secondary effect caused by such small variations, i.e., stable luminescent properties over time.

Means for Solving the Problems

The inventors have been studying the source and solution of the problems described above, and have consequently reached the following findings. The extent of a variation in film characteristics due to disturbance, i.e. the stability of the film, can be expressed by the magnitude of the Gibbs free energy change ($\Delta G$) in the film, from a thermodynamic perspective. The more negative the value of ΔG is, the higher stability the film has. The value of ΔG is represented by the expression below. In the present invention, the inventors have intended to accomplish the object of the invention by actively exploiting effects of entropy change (ΔS) as a measure to achieve a more negative value of ΔG.

$$\Delta G = \Delta H - T\Delta S$$

The inventors have made extensive studies based on the idea of actively exploiting ΔS, and have consequently found that use of functional organic compound(s) having chiral elements can increase the value of ΔS, resulting in a significant increase in stability of the film, without substantial changes in physicochemical properties of the film. Based on such findings, the inventors have completed the present invention.

The present invention involves the following aspects:

1. An electronic device including a charge-transporting thin film containing one or more types of functional organic compounds having chiral elements, wherein the total of the number of chiral elements per molecule in each type of the functional organic compounds summed over all types of the functional organic compounds is four or more.
2. The electronic device according to item 1, wherein the total of the number of chiral elements per molecule summed over all types of the functional organic compounds is within a range of five to fifteen.
3. The electronic device according to item 1 or 2, wherein the electronic device includes at least two types of the functional organic compounds having chiral elements, and each of the at least two types of the functional organic compounds includes at least one isomer selected from enantiomers and diastereomers.
4. The electronic device according to any one of items 1 to 3, wherein the electronic device includes at least two types of the functional organic compounds having chiral elements, at least one of the functional organic compounds includes both enantiomers and diastereomers.
5. The electronic device according to any one of items 1 to 4, wherein
the electronic device includes at least two types of the functional organic compounds having chiral elements, at least one of the functional organic compounds is a metal complex; and
the metal complex has two or more chiral elements per molecule, and thereby includes both enantiomers and diastereomers.
6. The electronic device according to any one of items 1 to 5, wherein the electronic device includes at least two types of the functional organic compounds having chiral elements, all of the at least two types of the functional organic compounds includes both enantiomers and diastereomers.
7. The electronic device according to any one of items 1 to 6, wherein the functional organic compounds having chiral elements have a biaryl structure which has chiral elements due to hindered rotation between two aryl moieties, such that the functional organic compounds include an atropisomer.
8. The electronic device according to any one of items 1 to 7, wherein the at least one type of the functional organic compounds having chiral elements is a compound which emits light during excitation under an electric field.
9. The electronic device according to item 8, wherein the compound which emits light during excitation under an electric field is the metal complex.
10. The electronic device according to any one of items 1 to 9, wherein
the charge-transporting thin film contains the functional organic compounds having chiral elements; and
a volatile organic material having a boiling point lower than 300° C. under normal pressure, wherein the volatile organic material has an asymmetric carbon atom.
11. The electronic device according to any one of items 1 to 10, wherein
each of the functional organic compounds contained in the charge-transporting thin film includes a mixture of the enantiomers and diastereomers;
the charge-transporting thin film contains a volatile organic material having a boiling point lower than 300° C. under normal pressure; and
the volatile organic material has an asymmetric carbon atom.
12. An electroluminescent element which is the electronic device according to any one of items 1 to 11.
13. An electrically conductive film which is the electronic device according to any one of items 1 to 11.
14. An organic thin-film solar cell which is the electronic device according to any one of items 1 to 11.
15. A dye-sensitized solar cell which is the electronic device according to any one of items 1 to 11.

Advantageous Effects of the Invention

The present invention provides an electronic device, an organic electroluminescent element, an electrically conductive film, an organic thin-film solar cell, and a dye-sensitized solar cell, which include a very stable charge-transporting thin film with small variations in properties due to disturbance and small variations in resistance over time during application of current. The invention further provides a secondary effect of stable luminescent properties over time caused by such small variations.

The mechanism of the advantageous effect of the present invention is presumed as described below.

The present invention effectively exploits entropic effects of functional organic compound(s) having chiral elements. Unlike conventional techniques, the configuration of the invention intentionally employs a configuration with a combination of functional organic compounds such that intended effects are achieved at a very high level.

BRIEF DESCRIPTION OF DRAWINGS

FIG. 6 is a schematic view of HOMO and LUMO energy levels of the individual molecules $A_1$ to $A_4$.

FIG. 7 is a schematic view illustrating a charge recombination thin film composed of five types of molecules.

EMBODIMENTS FOR CARRYING OUT THE INVENTION

Figure 1A:
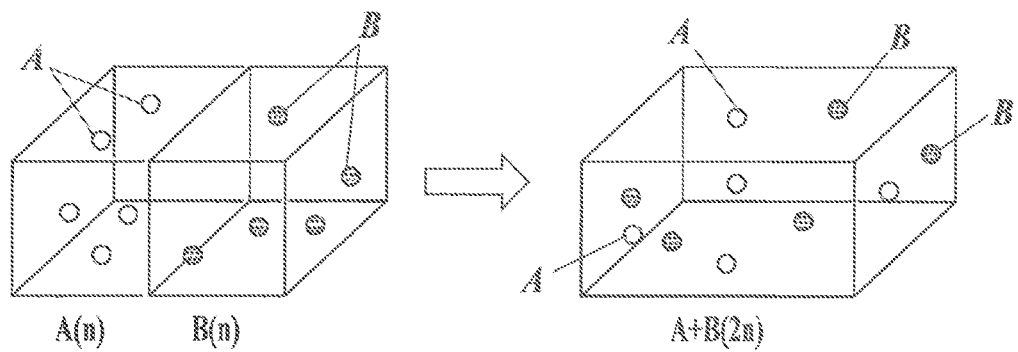
FIG. 1A is a schematic view illustrating entropy change in mixing of two gases.

The present invention provides an electronic device including a charge-transporting thin film containing one or more types of functional organic compounds having chiral elements, wherein the total of the number of chiral elements per molecule in each type of the functional organic compounds, when summed over all types of the functional organic compounds, is four or more. These technical features are commonly owned by the inventions according to claims 1 to 15.

In an embodiment of the present invention, the total of the number of chiral elements per molecule summed over all types of the functional organic compounds is preferably within a range of five to fifteen, from the viewpoint of the advantageous effects of the present invention. The electronic device of the invention preferably contains at least two types of the functional organic compounds having chiral elements, and each of the at least two types of the functional organic compounds includes at least one isomer selected from enantiomers and diastereomers. The electronic device of the invention preferably contains at least two types of the functional organic compounds having chiral elements, and at least one of the functional organic compounds includes both enantiomers and diastereomers.

The electronic device of the invention preferably contains at least two types of the functional organic compounds having chiral elements, and at least one of the functional organic compounds is a metal complex; and the metal complex preferably has two or more chiral elements per molecule, and thereby includes both enantiomers and diastereomers.

According to the present invention, the electronic device preferably contains at least two types of the functional organic compounds having chiral elements, and all of the at least two types of the functional organic compounds include both enantiomers and diastereomers.

The functional organic compounds preferably have a biaryl structure which has chiral elements due to hindered rotation between two aryl moieties, such that the functional organic compounds include an atropisomer.

At least one type of the functional organic compounds having chiral elements is preferably a compound which emits light during excitation under an electric field. The compound which emits light during excitation under an electric field is preferably the metal complex.

The charge-transporting thin film of the electronic device of the invention preferably contains the one or more types of functional organic compounds having chiral elements; and a volatile organic material having a boiling point lower than 300° C. under normal pressure, wherein the volatile organic material has an asymmetric carbon atom. Each of the functional organic compounds contained in the charge-transporting thin film includes a mixture of the enantiomers and diastereomers. The charge-transporting thin film preferably further contains a volatile organic material having a boiling point lower than 300° C. under normal pressure. The volatile organic material preferably has an asymmetric carbon atom.

The charge-transporting thin film of the present invention may be appropriately included in an electronic device, an organic electroluminescent element, an electrically conductive film, an organic thin-film solar cell, and a dye-sensitized solar cell.

The elements and embodiments of the present invention will now be described in detail. As used herein, the expression "to" indicating a numerical range is meant to be inclusive of the boundary values.

Before getting to the body of the description, the thermodynamic background on the technical idea of the present invention will be described.

[Thermodynamic Background]

One of the industrial products primarily composed of organic materials is a color photographic material. In particular, color papers (color photographic paper) are to be visually enjoyed; hence, an important technical element for the color image is high stability over time (referred to as preservability).

Color paper, for example, contains an ultraviolet absorber for the purpose of preventing light fading in color photographic images. Hydroxyphenylbenzotriazole derivatives are typical ultraviolet absorbers, and two or more of the derivatives are frequently present in color paper in the form of a mixture, for several reasons. For example, prevention of crystallization during long-term preservation is a fundamental requirement for ultraviolet absorbers and a mixture of several hydroxyphenylbenzotriazole derivatives effectively can inhibit crystallization for practical use. This phenomenon will be now discussed from thermodynamic viewpoints.

If no change occurs in a film or an article containing an organic material during preservation or use, its properties should not vary in any way. Characteristics required for such a film or article may vary depending on its application field. Examples of the required characteristics include development of colors, charge transfer characteristics, and optical characteristics such as a specific refractive index. In any case, if the film or the article experience no change in its condition, its characteristics should not vary in any way, that is, it should have infinite durability.

The stability of a film or an article (hereinafter, merely referred to as "film" for simpler explanation) depends on a change in Gibbs free energy ($\Delta G$) as defined in the second law of thermodynamics. Specifically, a film having a more negative value of $\Delta G$ has higher stability and thus barely undergoes variations in characteristics due to disturbance in use. The value of $\Delta G$ is represented by the following expression involving enthalpy change ($\Delta H$) and the product of entropy change and temperature ($T\Delta S$):

$$\Delta G = \Delta H - T\Delta S$$

The essence of the technique of the present invention lies in effective exploitation of entropic effects as a measure to achieve a more negative value of $\Delta G$ to increase the stability of a formed film, which consequently achieves smaller variations in characteristics of the film.

The concept of entropy will be now explained.

Figure 1B:
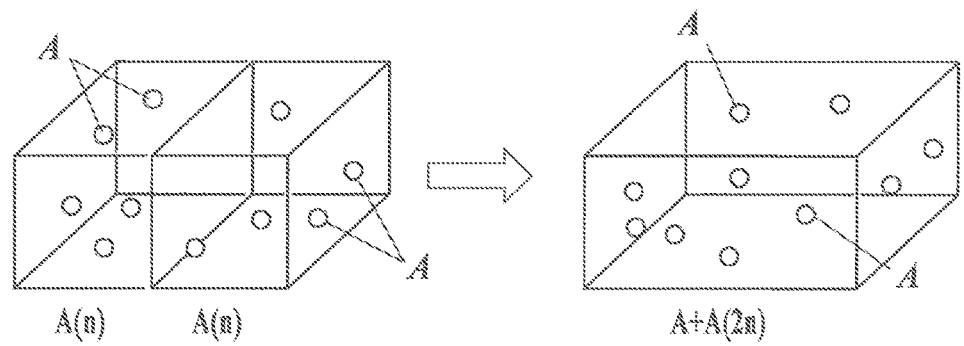
FIG. 1B is a schematic view illustrating entropy change in mixing of two gases.

In general, all gases are completely miscible with other gases. Almost all types of gas molecules are miscible with each other homogeneously, for the reason explained below with reference to FIG. 1A and FIG. 1B. FIG. 1A and FIG. 1B are schematic views illustrating entropy change in mixing of two gases.

It is supposed that a box divided by a partition in the central portion contains nitrogen molecules (component A) and oxygen molecules (component B) at the same packing density in the respective sections of the box (see FIG. 1A, left). When the partition is removed, the oxygen molecules and the nitrogen molecules mix with each other completely (see FIG. 1A, right). Since they are both gases, it is believed that the enthalpy does not substantially decrease. When the partition is removed, for example, the degree of disorder of the nitrogen molecules increases due to the coexistence of different molecules, i.e., the oxygen molecules, as compared to that before the removal. Such disorder means an increase in entropy. Unless the absolute temperature is zero (0K (Kelvin)), the value of $T\Delta S$ is positive, and thus the value of $\Delta G$ is negative. In other words, the entropic effect contributes to homogeneous mixing of gases.

Another case is supposed where both sections of the box contain nitrogen molecules (component A) at the same packing density (i.e. the same number of molecules). In such a case, the removal of the partition (see FIG. 1B, right) does not result in increase in the number of different molecules for the nitrogen molecules or change in the packing density of the nitrogen molecules, as compared to those before the removal (see FIG. 1B, left). Thus, no entropy change occurs. In other words, the coexistence of different molecules is essential for exertion of entropic effects.

This principle is applied to ultraviolet absorbers.

[Chemical Formula 1]

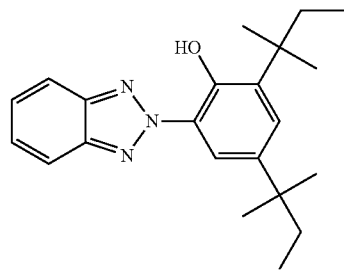

BT-1

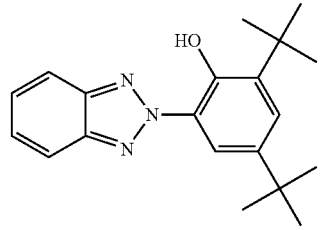

BT-2

A benzotriazole derivative having tert-amyl substituent group is referred to as BT-1 (component A), and another benzotriazole derivative having tert-butyl substituent group is referred to as BT-2 (component A).

The schematic view shown in FIG. 1A corresponds to combined use of BT-1 and BT-2 and that shown in FIG. 1B corresponds to use of BT-2 alone, in film formation.

It can be understood that the Gibbs free energy of the resulting film has a more negative value, that is, the film is more stable, in the combined use of BT-1 and BT-2 (corresponding to FIG. 1A) than in the single use of BT-2 (corresponding to FIG. 1B), as in the case of mixing of nitrogen and oxygen. Since BT-1 and BT-2 have a common basic structure, hydroxyphenylbenzotriazole, which is involved in the interaction, it is believed that they have substantially identical enthalpy values. This effect of improving stability is due to the entropic effect caused by the coexistence of different molecules. In other words, in use of a mixture of ultraviolet absorbers BT-1 and BT-2, it is believed that the entropic effect contributes to the effect of preventing crystallization of ultraviolet absorbers during long-term use. Very few evidences have been reported which demonstrate or discuss such prevention of crystallization from thermodynamic viewpoints. Entropy (degree of disorder) is more difficult to imagine in a real situation than enthalpy (attractive force). Due to such difficulty, most evidences do not discuss a technique of improving durability by active exploitation of entropy regardless of its significant effect.

The most representative examples of exploitation of entropic effects for stability are metal complexes. Table 1 shows thermodynamic parameters for various amine complexes of cadmium, as calculated based on the stability of each complex measured at a room temperature.

TABLE 1

| No. | Complex compound | log β | −ΔG⁰ (kJ/mol) | −ΔH⁰ (kJ/mol) | TΔS⁰ (kJ/mol) |
|---|---|---|---|---|---|
| 1 | $Cd(NH_2)_2^{2+}$ | 4.95 | 28.2 | 29.8 | −1.5 |
| 2 | $Cd(MeNH_2)_2^{2+}$ | 4.81 | 27.4 | 29.4 | −1.9 |
| 3 | $Cd(H_2NC_2H_4NH_2)$ | 5.84 | 33.3 | 29.4 | 3.9 |

[Chemical Formula 2]

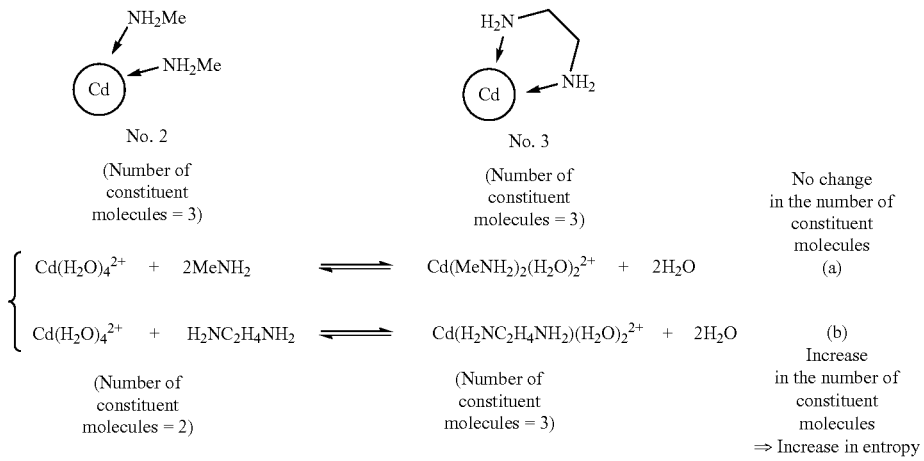

For example, the complex No. 3 (cadmium-ethylenediamine complex) is a chelate complex, while the complex No. 2 (cadmium-bismethylamine complex) is not a chelate complex. Comparison of these complexes indicates that they are the same in enthalpy (which may be interpreted as attractive force) but significantly differ in entropy. The difference in entropy, i.e. 5.8 kJ/mol, indicates the difference in stability between the chelate and non-chelate complexes. This value indicates a significant stabilization energy corresponding to 21% of the Gibbs free energy of the complex No. 2.

The high stability of chelate complexes can be intuitively understood, and is generally and widely known. It, however, is not commonly known that entropic effects largely contribute to the significant energy. The source of the entropic effects will be now described. Entropy can also be represented by the product of Boltzmann constant and the number of constituent molecules. A change in the number of constituent molecules helps better understanding of entropic effects of chelate complexes.

Formula (a) shows that the number of constituent molecules in the non-chelate complex No. 2 is three both before and after complex formation. Meanwhile, Formula (b) shows that the number of constituent molecules in the chelate complex No. 3 is two before complex formation and increases to three after complex formation, which indicates an increase in entropy.

The extent of influence of the chelate complex formation on the durability of a resulting product will now be explained with a specific example (see KONICA TECHNICAL REPORT, pp. 83-86, vol. 14(2001)).

Konica Photo Chelate (registered trademark) is a print material for post-chelating dye transfer print. In its image formation method, a dye having a structure as a ligand is transferred by diffusion onto an image receiving layer containing a metal ion compound, and then reacts with the metal ion compound to form a chelate. A chelate dye is thereby produced and fixed on the image receiving layer. The produced image dye (chelate complex dye) provides improved image fixation and light and heat resistances, which achieves excellent durability for printed images.

Figure 2A:
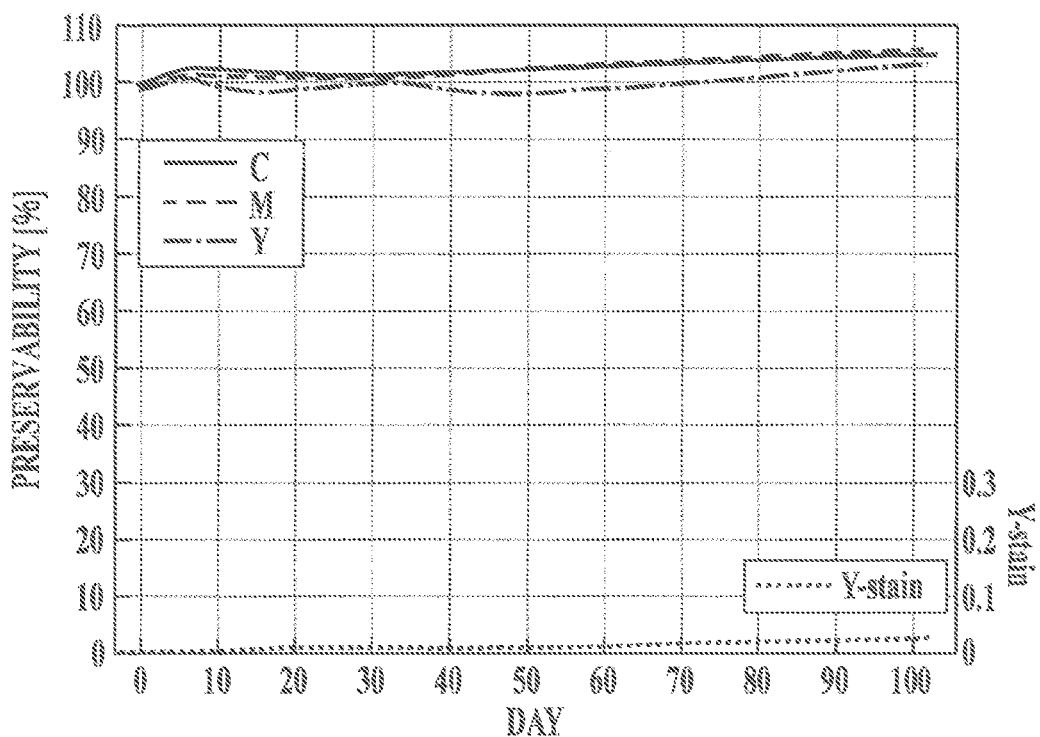
FIG. 2A shows an example of color image fastness achieved with a chelate complex dye.
Figure 2B:
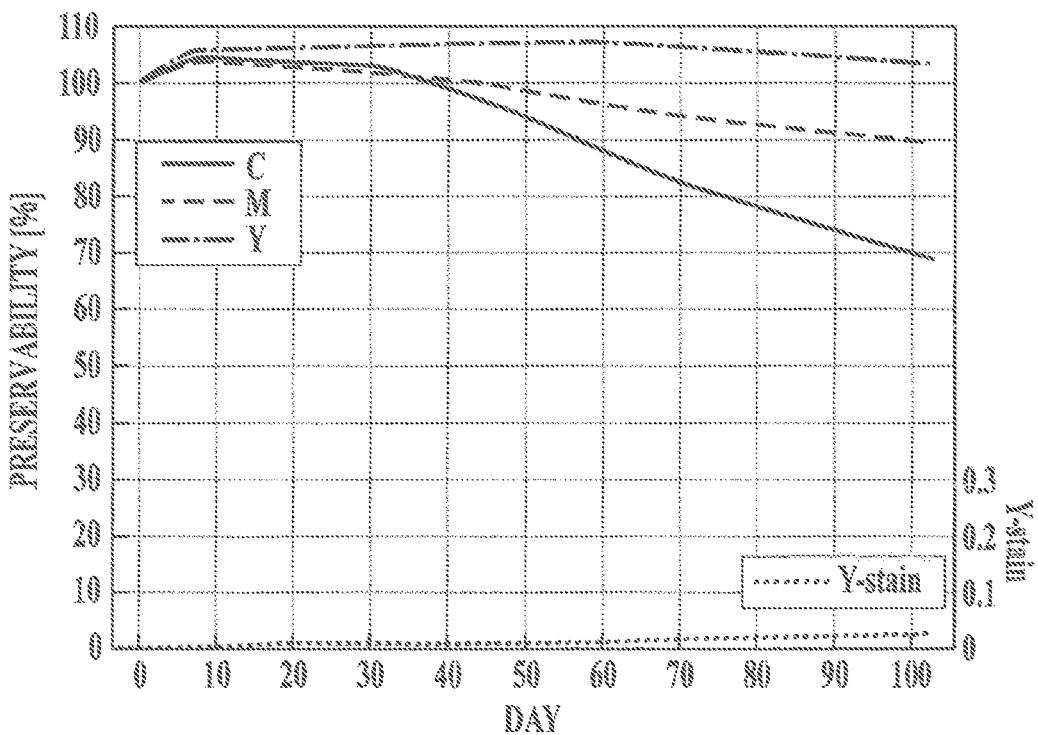
FIG. 2B shows an example of color image fastness achieved with a chelate complex dye.

The effect is demonstrated by comparing FIG. 2A and FIG. 2B. FIG. 2A and FIG. 2B respectively show examples of color image fastness achieved with individual chelate complex dyes based on results of dark fading test at a temperature of 65° C., indicating variations in color density for cyan, magenta, and yellow dyes respectively represented by C, M, and Y. FIG. 2A shows the results of a test achieved in printing with Konica Photo Chelate using chelate complex dyes, and FIG. 2B shows those achieved in ordinary thermal dye transfer printing. The results are clearly distinct, and indicate that no fading occurs in the image dyes of Photo Chelate even under high-temperature preservation.

Specifically, in Photo Chelate, the entropy of the film containing dyes is greater at the time of image formation and the entropic effect provides a stable film. As a result, the film satisfies industrial requirements of image preservability.

Thus, by effectively exploiting the entropic effect, it is possible to provide a film mainly composed of organic materials with increased Gibbs free energy in the initial state. This effect of increasing Gibbs free energy is high enough to prevent variations in characteristics of the film even under severe environments, such as long-term or high-temperature preservation.

[Increase in Entropy in Charge-Transporting Thin Film]

Figure 3A:
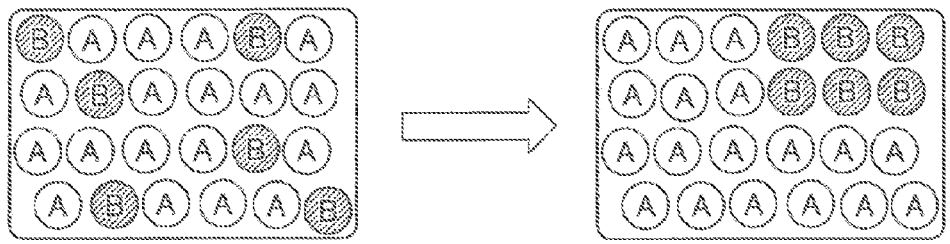
FIG. 3A is a schematic view illustrating a change in state of a charge transport layer or a transporting thin film.
Figure 3B:
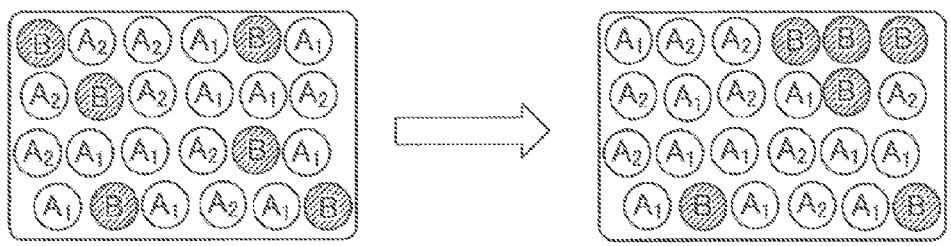
FIG. 3B is a schematic view illustrating a change in state of a charge transport layer or a transporting thin film.

The main subject of the present invention is a charge-transporting thin film. The concept of the invention will now be described with reference to the drawings, focusing on a technique of increasing Gibbs free energy of the film, from the view point of charge transfer. FIG. 3A and FIG. 3B are each a schematic view illustrating a change in state of a charge transport layer or a thin transport film.

For example, a film is supposed which contains molecules A and B having mutually different functions as shown in FIG. 3A, left, and which undergoes changes in state of the molecules A and B as shown in FIG. 3A, right, after application of current or long-term preservation.

Other molecules $A_1$ and $A_2$ are supposed which have the same function as the molecule A but are different from the molecule A in structure. The molecules $A_1$ and $A_2$ are different molecules although they have the same function, and thus may be a factor to cause disorder, according to the concept of entropy. In other words, the film containing a mixture of three components, i.e. the molecules $A_1$, $A_2$, and B, as shown on the left in FIG. 3B has a higher degree of disorder, in comparison with the film shown on the left in FIG. 3A. This indicates that the original Gibbs free energy is more negative in the film shown on the left in FIG. 3B than in that shown on the left in FIG. 3A. Thus, even if the film shown in the schematic view of the left in FIG. 3B is exposed to the same conditions where the film shown on the left in FIG. 3A undergoes a change as shown on the right in FIG. 3A, the change in state shown on the right in FIG. 3B is smaller than that shown on the right in FIG. 3A.

Figure 4A:
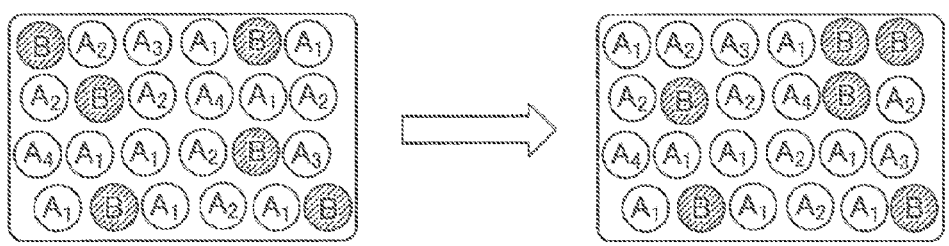
FIG. 4A is another schematic view illustrating a change in state of a charge transport layer or a transporting thin film.
Figure 4B:
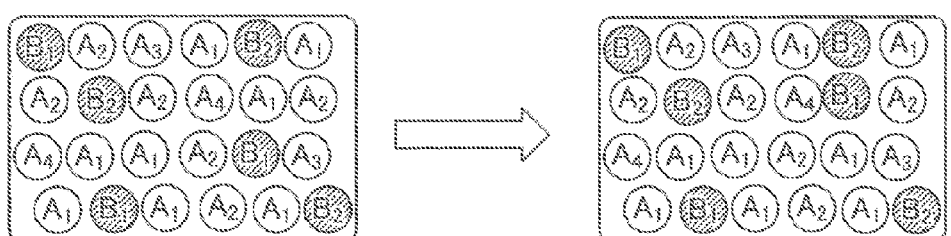
FIG. 4B is another schematic view illustrating a change in state of a charge transport layer or a transporting thin film.

This technical concept is expanded as shown on the left in FIG. 4A and the left in FIG. 4B.

In FIG. 4A, left, molecules A consist of four mutually different molecules $A_1$, $A_2$, $A_3$ and $A_4$. In FIG. 4B, left, molecules B are also shown as two mutually different molecules $B_1$ and $B_2$. From the viewpoint of entropy, such an increase in the number of components directly contributes to an increase in entropy, so as to achieve a significant effect on an improvement in stability.

Polymer materials are generally believed to have excellent film-forming properties. In other words, the initially formed thin film is less likely to undergo variations in its characteristics over time.

A polymer has a molecular weight distribution, and even polymer chains having the same molecular weight have different conformations, such as linear, random coil, and flexed conformations. In other words, one of the polymer chains is a foreign chain to any other polymer chain. In view of this fact, polymers have a high entropy.

Since a polymer composed of the same repeating units is believed to have similar enthalpy values corresponding to attractive force between molecules, the excellent film forming properties of polymers are probably due to the entropic effect.

Meanwhile, use of a polymer in a charge-transporting thin film as in the subject of the present invention involves the following disadvantages: If the charge-transporting thin film is mainly composed of organic molecules, most charge transfer occurs via intermolecular hopping. In such a case, trace amounts of impurities produce trap levels, which hinders the charge transfer and thus impairs original properties of the polymer. For this reason, when polymers are applied to organic EL devices or organic thin-film solar cells, removal of such impurities is a major obstacle.

Radically polymerized polymers also involves a problem: the presence of the moiety from a radical initiator in the end of the resulting polymer is disadvantageous for a charge-transporting thin film to be applied to electric field devices. In polymer synthesis involving a reaction such as Suzuki coupling or Negishi coupling, use of a transition metal catalyst is essential, and the residual catalyst frequently produce trap levels, which causes fatal defects. Thus, atoms and ions of the transition metal must be perfectly removed to ppm levels, which is a great limitation for such industrial application.

Polymers also have fatal defect that fine purification such as recrystallization or sublimation cannot be applied, unlike low-molecular weight compounds.

Another disadvantage of polymers is that they do not have the same physicochemical properties of their repeating units, and essential physical properties for a charge-transporting thin film, for example HOMO and LUMO levels, absorption spectrum, and emission spectrum, vary depending on their degree of polymerization and conformation, which causes a higher level of difficulty in active molecular design of a polymer molecule having a specific action of interest, as compared to molecular design of a low-molecular weight compound composed of a single molecule.

If the advantage of polymers can be achieved with low-molecular compounds while solving the disadvantages of polymers, then low-molecular weight compounds can be actively applied to both vapor deposition and wet deposition process, such as coating and ink jetting. If future electronic devices are required to have higher performances, use of such low-molecular weight compounds can combine the excellent film forming properties of polymers, i.e. higher stability of a charge-transporting thin film, with their characteristics of low-molecular weight compounds, i.e. easy molecular design, easy fine purification, and easy achievement of major physical properties of interest, such as specific energy levels and spectra. Such low-molecular weight compounds are appropriate for future industrial applications.

It is an essential requirement for industrial developments to provide such an ideal low-molecular weight material, and technological innovation in the field of materials depends on achievement of such a material. In other words, it is no exaggeration to say that the technological innovation depends on achievement of a technique for activation of entropic effect in a low-molecular weight material.

[Stability of Charge-Transporting Thin Film]

In the foregoing description, ideal low-molecular-weight materials are discussed from the viewpoint of film stability. Meanwhile, since the present invention is applied to an electronic device including a charge-transporting thin film, materials used in the charge-transporting thin film have limitations as described below. Organic materials are basically insulating materials, and thus charge transfer therein occurs via a phenomenon referred to as hopping.

Figure 5A:
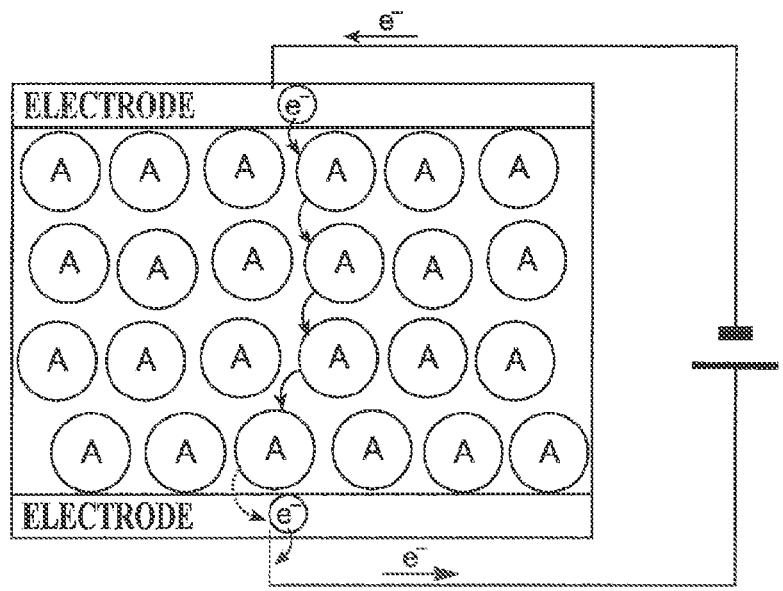
FIG. 5A is a schematic view illustrating hopping transfer and recombination in charge transfer.
Figure 5B:
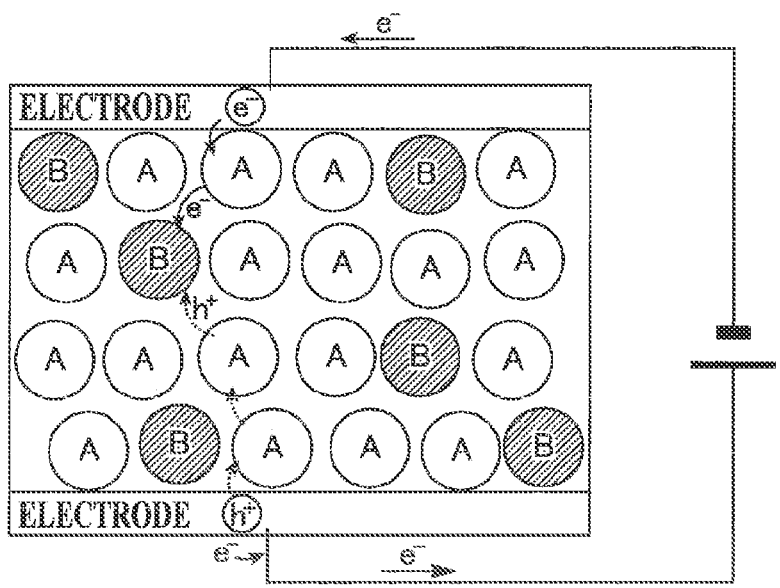
FIG. 5B is a schematic view illustrating hopping transfer and recombination in charge transfer.

Charge transfer via hopping is explained with reference to the drawings. FIG. 5A and FIG. 5B are schematic views illustrating hopping transfer and recombination in charge transfer, respectively.

As shown in FIG. 5A, charge carriers (in FIG. 5A, electrons) are injected from an electrode into organic material A, and transfer by hopping from a molecule A to an adjacent molecule A, and finally the electrons are donated to the counter electrode to produce electron current. A phenomenon referred to as charge recombination is another type of charge transfer based on the same principle. Regarding holes as empty molecules from which electrons have been ejected, donation of electrons to the counter electrode is synonymous to injection of holes from the counter electrode.

FIG. 5B schematically shows a model of charge recombination. In this model, electrons are injected from a cathode and holes are injected from an anode, and charges from the individual carriers recombine together on the molecule B. If the molecule B is a luminescent substance, light is emitted when the excited molecule B returns to the ground state, that is, an organic EL device is provided.

In charge transfer occurring in a thin film composed of organic materials, carrier trap should be taken into consideration.

FIG. 6 is a schematic view of HOMO (highest occupied molecular orbital) and LUMO (lowest unoccupied molecular orbital) energy levels of the individual molecules $A_1$ to $A_4$ which have the same function as the molecule A. FIG. 7 is a schematic view illustrating a thin charge recombination film composed of five types in total of molecules, i.e. molecules $A_1$ to $A_4$ having the same function as the molecule A and molecule B having a different function.

In FIG. 6, the HOMO and LUMO energy levels shown at a lower portion of the figure is farther from the vacuum level (i.e. deeper level). Electrons injected from one of the electrodes do not enter all the molecules $A_1$ to $A_4$ at the same probability. They are always injected or localized at higher probability in molecules having deeper LUMO levels. When holes are injected from an anode, they are injected or localized at higher probability in a molecule having a shallower HOMO level.

For example, it is supposed that the molecules $A_2$ have a deeper LUMO level than the other three types of molecules and the molecules $A_4$ have a shallower HOMO level than the other three types of molecules. If electric fields are applied to a thin film containing such molecules, electrons are trapped by the molecules $A_2$ at high probability and holes are trapped by the molecules $A_4$ at high probability, which consequently decreases the probability of intended recombination of the electrons and the holes at the molecules B.

If the molecule B is a luminescent substance and the film shown in FIG. 7 is used in an organic EL device, increased amounts of electrons and holes are required to generate a sufficient amount of excitons in the molecules B in order to achieve a specific luminance. Increases in amounts of carriers to be injected results in a higher driving voltage, and continuous application of high driving voltage increases amounts of carriers to be captured in carrier traps. Since energy of captured carriers is converted to vibrational energy that is not involved in emission of light, the additionally injected electrons and holes eventually waste their energy in the form of heat. The thin film containing the molecules B is then locally heated to a high temperature, which results in higher tendency of changes in the state of the thin film. Therefore, a mere increase in the number of components does not work, and it is essentially required to use in combination multiple types of molecules which have a certain common function and substantially identical energy levels.

In this theory, some industrial issues should also be taken into consideration.

First, it is required to design multiple types of molecules having substantially identical energy levels. Of course, the molecules should be prepared in a sufficient amount and so as to satisfy the specification, such as purity, required for practical use. If vacuum vapor deposition is employed in formation of a film, the required number of vapor deposition sources corresponds to the number of components. It is substantially impossible to prepare five or more vapor deposition sources in a single vacuum chamber, from the viewpoint of manufacturing costs.

The essence of the present invention lies in a method to solve these problems simultaneously. A measure to solve the problems is to use functional organic compounds having chiral elements, which can increase $\Delta S$, resulting in a significant increase in stability of the film, without substantial changes in physicochemical characteristics of the film. Preferably, functional organic compounds including at least one isomer selected from enantiomers and diastereomers is used. Use of materials composed of many different molecules having a common function causes the resulting charge-transporting thin film to have a more negative Gibbs free energy at the initial state after the formation (i.e. the resulting thin film barely undergoes variations in characteristics due to thermal, electric, or light disturbance). As explained above, this effect is caused by increased entropy, not depending on a specific chemical structure, and thus can be exploited as a universal measure for improving the stability.

Enantiomers are defined as isomers that have identical physicochemical properties, except for physiological activity. Diastereomers are defined as isomers which do not have identical physicochemical properties like enantiomers but have very similar physicochemical properties. The enantiomers and diastereomers therefore do not substantially lead to undesired carrier traps explained with reference to FIG. 7.

At the time of purification to obtain a final product, enantiomers and diastereomers are not completely separated as single materials, when a purification method without chiral sources is applied. Thus, use of enantiomers and diastereomers is very reasonable to prepare a mixture of a large number of different molecules by a single synthetic and purification procedure.

<<Enantiomers and Diastereomers>>

Enantiomers and diastereomers will now be described in detail.

[Chemical Formula 3]

(I)

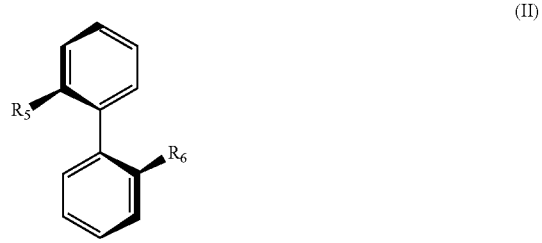

(II)

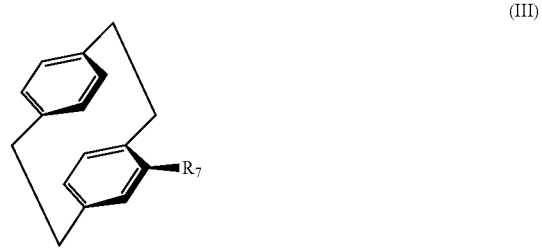

(III)

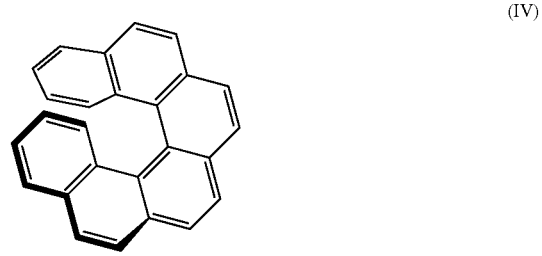

(IV)

[Chemical Formula 4]

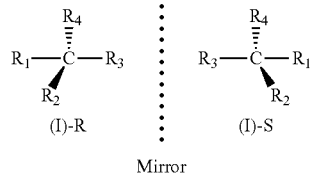

Mirror

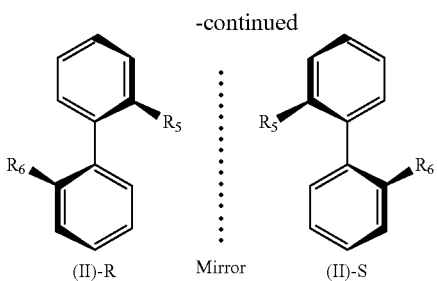

(II)-R   Mirror   (II)-S

Figure 19:
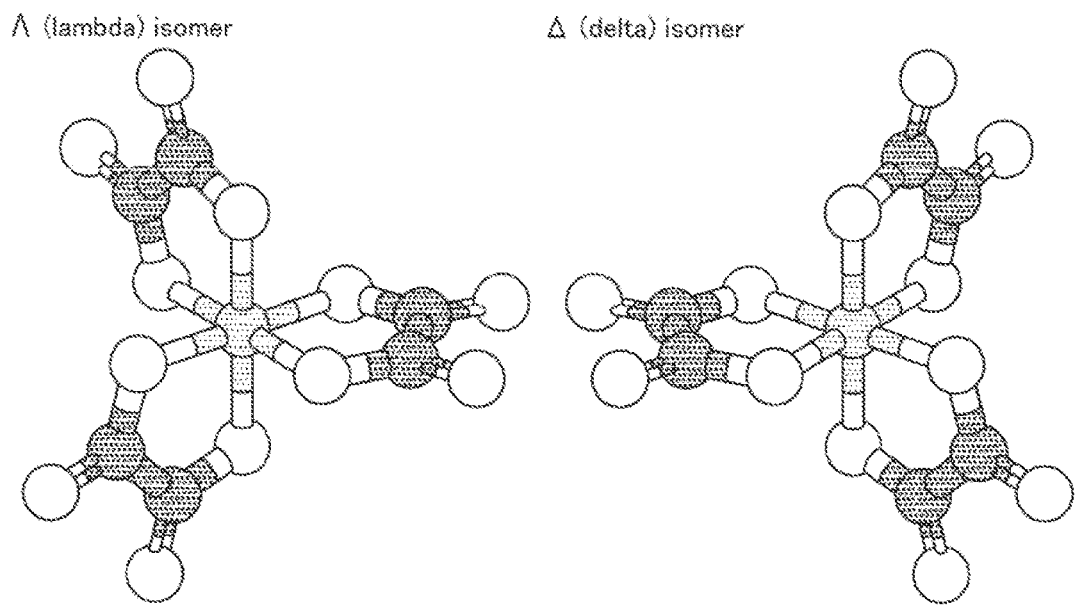
FIG. 19 illustrates octahedral complexes coordinated with bidentate ligands having delta and lambda isomers.

The compounds shown above are major types of the organic functional compound having chiral elements according to the present invention. Formula (I) shows the most common type, a compound with an asymmetric carbon atom, i.e. a compound having a carbon atom (or an atom having unpaired electrons, such as nitrogen, sulfur, or phosphorus atom) which has four different substituent groups. Formula (II) shows an axially chiral compound, i.e., a molecule which has a bulky substituent groups at ortho positions of individual moieties such that the bond axis between the two moieties is rotationally hindered (atropisomeric axis), resulting in rotational isomerism of the molecule. An example of such a structure is a biaryl structure. Formula (III) shows a compound with planar chirality, i.e., a compound having two aromatic rings which are fixed or cannot easily rotate, so as to cause chiral elements. Formula (IV) shows a helical compound having a predetermined direction of twist. An examples of such a compound is helicene. The organic functional compound of the present invention also include compounds which exhibit asymmetric mirror images by complex formation. Octahedral complexes coordinated with bidentate ligands include enantiomers, i.e. isomers which are mutually in mirror-image relationship, referred to as Δ (delta) and Λ (lambda) isomers (respectively corresponding to right-handed and left-handed propellers) is shown in FIG. 19.

Enantiomers are also referred to as mirror-image isomers which are in a mirror-image relationship like right and left hands. This applies not only to compounds with an asymmetric carbon atom but also to the compounds of Formulae (II), (III) and (IV), and other materials having chiral elements. In any of these types, isomers in a mirror-image relationship are referred to as enantiomers, and in other words, they are in an enantiomeric relationship to each other.

"Diastereomers" refers to molecules which arise if two or more chiral elements are present and which are not in a mirror-image relationship but appear identical based on two-dimensional representation of their molecular structure. In other words, the molecules are in a diastereomeric relationship.

Figure 20:
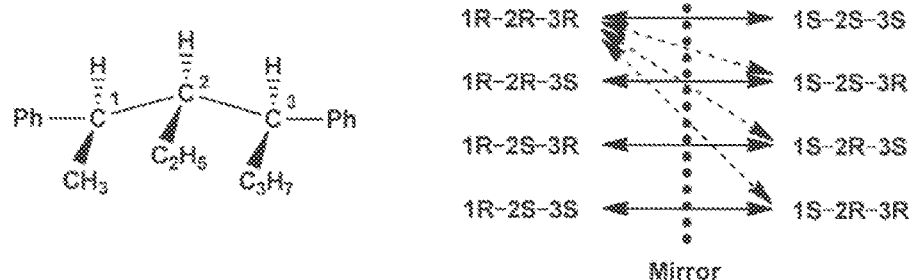
FIG. 20 illustrates a compound having three asymmetric carbon atoms.

A specific example of a compound having three asymmetric carbon atoms is shown in FIG. 20.

This molecule has eight isomers. Among them, four pairs of isomers are each in a mirror-image relationship, that is, enantiomeric, and the other pairs are each diastereomeric. Double-headed solid arrows represent an enantiomeric relationship, and double-headed dashed arrows represent a diastereomeric relationship.

Figure 21:
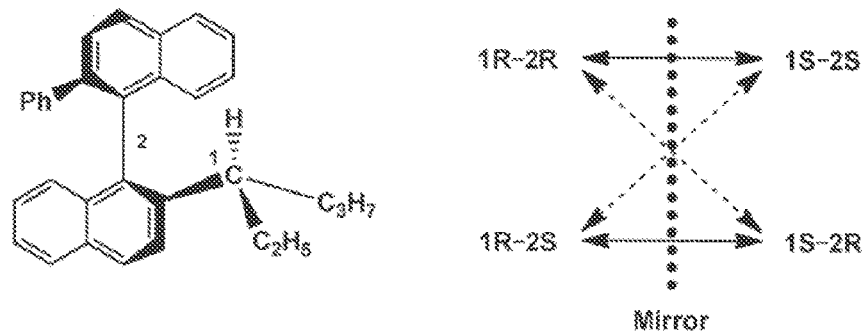
FIG. 21 illustrates a compound having one axial chirality and one asymmetrical carbon atom.

A specific example of a compound having one axial chirality and one asymmetric carbon atom is shown in FIG. 21. Any types of chirality can be combined.

In complexes having multiple ligands, such as trivalent hexacoordinate iridium complexes, if one of their ligands has a chiral element, the resulting complex has multiple chiral elements. As a result, the complex naturally includes diastereomers.

Even if a ligand itself does not have any chiral element or any possibility of the presence thereof, complex formation may induce axial chirality, planar chirality, or helicity, and the resulting complex may have multiple chiral elements. Such complexes may also be used in the present invention.

The following point should be remembered.

Some documents, for example, Japanese Unexamined Patent Application Publication No. 2008-525995 and Japanese Patent Application Laid-Open Publication No. 2007-177252, disclose techniques of improving device lifetime with isomeric compounds. Unfortunately, these techniques happen to exploit entropic effects, and do not intentionally employ a configuration with a combination of compounds in order to achieve intended effects. Although the conventional techniques happen to provide some effects, the effects have been inadequate for general use in industrial applications. Consequently, it would not have been easily inferred from the conventional techniques which just happen to exploit entropic effects to apply the effect as a measure to solve the problems to arrive at the solution to the problems provided by the present invention as will be described below. The solution to the problems has been achieved by the present invention for the first time.

Many other documents disclose exemplary compounds without identifying whether they are enantiomers or diastereomers, although two-dimensional representation thereof implies possible presence of enantiomers or diastereomers. Of course, some of the known compounds should contribute to high entropic effects when they are actively used in combination with at least one isomer selected from enantiomers and diastereomers for the following reason: The essence of the technical idea of the present invention lies in "coexistence of different molecules having identical energy level", basically regardless of the types (known or unknown) and molecular weights and chemical structures of the compounds to be used.

In other words, even if some of the compounds disclosed in these known documents incidentally contribute to the coexistence of multiple enantiomers or diastereomers, these known techniques should be distinguished from the present invention, unless they clearly indicate the intention to actively use such isomers to achieve a thin film with more negative Gibbs free energy, or the intention to use a mixture of isomers to achieve a film with increased entropy in the initial state. The inventors have carefully researched conventional documents, but have found no disclosure of such a technical idea.

<<Charge-Transporting Thin Film>>

The charge-transporting thin film according to the present invention contains one or more types of functional organic compounds having chiral elements, wherein the total of the number of chiral elements per molecule in each type of the functional organic compounds, when summed over all types of the functional organic compounds, is four or more.

For example, ortho-metalated iridium complexes having a facial configuration with a hexadentate ligand have one chiral element in structure, and are known as materials for organic EL thin films. However, the advantageous effects of the present invention cannot be achieved with such complexes alone, and slight effects observed with compounds having two or three chiral elements are still insufficient. Meanwhile, an increased number of chiral elements should increase the advantageous effect of the present invention.

This is probably because a smaller number of chiral elements renders the resulting thin film more subject to influences by other factors.

As explained above, a greater total number of chiral elements is preferred. The total number of chiral elements is preferably at least five, more preferably at least six, and further more preferably at least seven. The total number of optically active elements has no particular upper limit, and a greater total number of chiral elements is more preferable for achieving the advantageous effects of the present invention, because it enhances the entropic effects while having substantially identical energy levels.

The term "charge-transporting thin film" (also referred to as "organic functional layer") refers to a layer containing a functional organic compound capable of transporting charge carriers (generic terms including electrons and holes) during application of electric fields. Such a charge-transporting thin film is applied to electronic devices, such as organic EL devices, organic thin-film solar cells, dye-sensitized solar cells, and organic thin-film transistors.

Examples of the charge-transporting thin film used in the present invention include a hole blocking layer, an electron blocking layer, an electron injection layer, and a hole injection layer, in addition to a hole transport layer, a photoelectric unit (bulk heterojunction layer), and an electron transport layer.

(Organic EL Device)

For example, the organic EL device may have the following layer configuration (i) or (ii):
(i) anode/hole injection layer/hole transport layer/luminous layer/electron transport layer/electron injection layer/cathode; or
(ii) anode/hole injection layer/hole transport layer/luminous layer/hole blocking layer/electron transport layer/electron injection layer/cathode.

The organic EL device may further be provided with other layer(s) containing functional organic compounds, such as an electron blocking layer. The organic EL device may have a tandem structure (multiphoton structure) composed of repeating units of organic functional layers deposited on an electron injection layer through charge generating layers.

Examples of the charge-transporting thin film include a hole injection layer, a hole transport layer, an electron blocking layer, a luminous layer, a hole blocking layer, an electron transport layer, and an electron injection layer.

(Organic Thin-Film Solar Cell)
(Structure of Organic Photoelectric Device and Solar Cell)

The organic photoelectric device includes both devices for converting electric energy into light and devices for converting light into electric energy. Typical examples of the former include light-emitting diodes and semiconductor laser devices, and typical examples of the latter include photodiodes and solar cells.

For example, a solar cell having a single structure including a bulk heterojunction organic photoelectric device (i.e. a structure composed of a single bulk heterojunction layer) may have the following layer configuration (i): (i) substrate/transparent electrode (anode)/hole transport layer/photoelectric unit (bulk heterojunction layer)/electron transport layer/counter electrode (cathode).

The bulk heterojunction photoelectric device is formed by laminating a transparent electrode (anode), a hole transport layer, a bulk heterojunction layer as a photoelectric unit, an electron transport layer, and a counter electrode (cathode) in sequence onto one side of a substrate.

The substrate is an element to support the transparent electrode, the photoelectric unit, and the counter electrode which are laminated thereon in sequence. In the present embodiment, since the incident light to be subjected to photoelectric conversion enters the substrate, the substrate is composed of a material which can transmit the light to be subjected to photoelectric conversion, that is, a material which is transparent to the wavelength of the light to be subjected to photoelectric conversion. The substrate may be, for example, a glass substrate or a resin substrate. The substrate is not an essential element. For example, a bulk heterojunction organic photoelectric device may be produced by depositing a transparent electrode and a counter electrode on both sides of the photoelectric unit.

The photoelectric unit is a layer which converts light energy into electric energy, and is composed of a bulk heterojunction layer containing a homogeneous mixture of p-type and n-type semiconductor materials. P-type semiconductor materials function relatively as an electron donor (donor), and n-type semiconductor materials function relatively as an electron acceptor (acceptor). As used herein, the terms "electron donor" and "electron acceptor" refer to "an electron donor and an electron acceptor which form a hole-electron pair (charge separation state) via electron transfer from the electron donor to the electron acceptor due to light absorption". In other words, they donate or accept electrons via a photoreaction, unlike electrodes that simply donate or accept electrons.

The light incident on the transparent electrode through the substrate is absorbed by an electron acceptor or an electron donor in the bulk heterojunction layer as the photoelectric unit. An electron is transferred from the electron donor to the electron acceptor to form a hole-electron pair (charge separation state). The generated charge is transported by an internal electric field (for example, the electric potential difference between the transparent electrode and the counter electrode, if they have different work functions). An electron passes through electron acceptors, while a hole passes through electron donors, and they are respectively transported to different electrodes. A photocurrent is thus detected. For example, if the transparent electrode has a work function higher than that of the counter electrode, electrons are transported to the transparent electrode, while holes are transported to the counter electrode. If the transparent electrode and the counter electrode have reverse levels of work function, electrons and holes are respectively transported to reverse directions. The directions of transportation of electrons and holes can be controlled by applying a potential across the transparent electrode and the counter electrode.

(Dye-Sensitized Solar Cell)

For example, the dye-sensitized solar cell may have the following layer configuration (i):
(i) electrically conductive support/photosensitive layer/charge transfer layer/counter electrode.

When the solar cell of the invention is irradiated with sunlight or electromagnetic waves equivalent to sunlight, the sensitizing dye adsorbed on a semiconductor photoelectric material absorbs the incident light or electromagnetic waves and is excited. Electrons generated by the excitation of the dye transfer to the semiconductor, pass through the electrically conductive support to the counter electrode, and then reduce the redox electrolyte in the charge transfer layer. Meanwhile, materials (functional organic compounds) of the organic solar cell of the present invention are oxidized by transfer of electrons to the semiconductor, and are then reduced to the original state by electrons supplied from the counter electrode through the charge transfer layer. As a result, the redox electrolyte in the charge transfer layer also returns to the oxidized state that can be reduced again by electrons supplied from the counter electrode. Electrons flow in this way. A solar cell including a photoelectric device of the present invention may have such a structure.

(Organic Thin-Film Transistor)

Figure 8A:
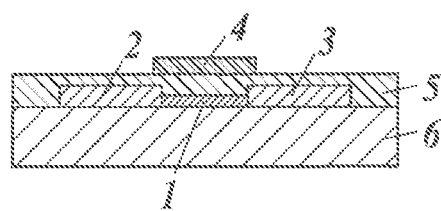
FIG. 8A is a view illustrating an exemplary structure of an organic thin-film transistor.
Figure 8B:
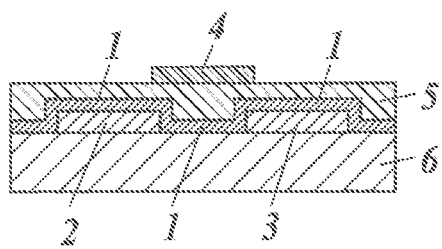
FIG. 8B is a view illustrating another exemplary structure of an organic thin-film transistor.
Figure 8C:
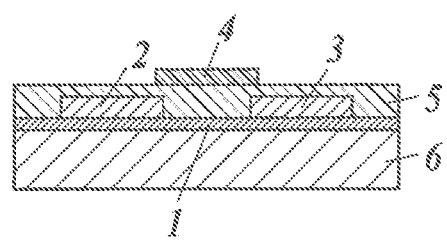
FIG. 8C is a view illustrating another exemplary structure of an organic thin-film transistor.

FIG. 8A to FIG. 8F each show a structure of an organic thin-film transistor. FIG. 8A shows a structure of a field effect transistor manufactured by depositing a material, such as a metal foil onto a support 6 to form a source electrode 2 and a drain electrode 3; forming a charge-transporting thin film (organic semiconductor layer 1) composed of organic thin-film transistor materials, i.e. functional organic compounds of the present invention, between the two electrodes; depositing an insulation layer 5 on the organic semiconductor layer 1; and then depositing a gate electrode 4 on the insulating layer 5. FIG. 8B shows a structure of the organic semiconductor layer 1 formed by a process such as coating so as to entirely cover the electrodes and the surface of the support, unlike the organic semiconductor layer 1 provided between the electrodes in the structure shown in FIG. 8A. FIG. 8C shows a structure in which an organic semiconductor layer 1 is first formed on a support 6 by a process such as coating, and a source electrode 2, a drain electrode 3, an insulation layer 5, and a gate electrode 4 are then formed thereon.

Figure 8D:
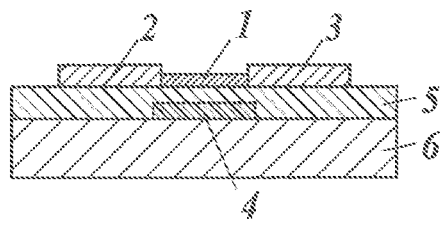
FIG. 8D is a view illustrating another exemplary structure of an organic thin-film transistor.
Figure 8E:
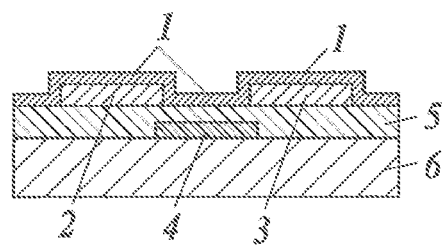
FIG. 8E is a view illustrating another exemplary structure of an organic thin-film transistor.
Figure 8F:
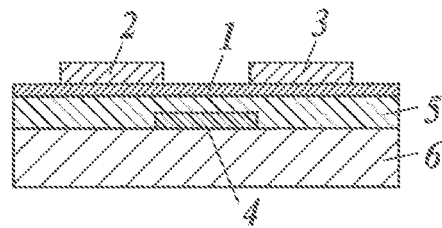
FIG. 8F is a view illustrating another exemplary structure of an organic thin-film transistor.

FIG. 8D shows a structure in which a material such as metal foil is deposited onto a support 6 to form a gate electrode 4; an insulation layer 5 is then formed thereon; a material such as metal foil is deposited thereon to form a source electrode 2 and a drain electrode 3; and then an organic semiconductor layer 1 is formed between the electrodes with an organic thin-film transistor material according to the present invention. FIG. 8E and FIG. 8F show other exemplary structures of the organic thin-film transistor of the present invention.

Figure 9:
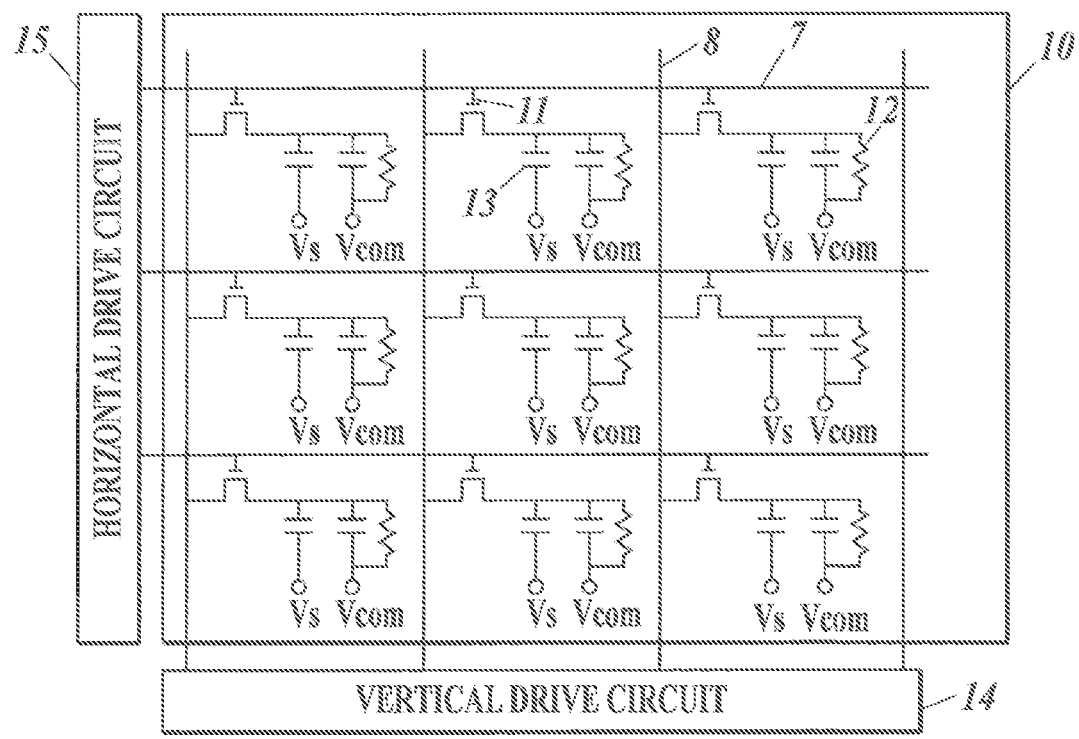
FIG. 9 shows an example of schematic equivalent circuit diagram of organic thin-film transistors.

FIG. 9 shows an example schematic equivalent circuit diagram of organic TFT sheet.

An organic TFT sheet 10 includes a matrix of many organic TFTs 11. Each TFT 11 has a gate bus line 7 and a source bus line 8. Each TFT 11 has a source electrode connected to an output device 12 that is a liquid crystal or electrophoretic device, for example, and constitutes pixels of the display device. Pixel electrodes may be used as input electrodes of photosensors. In the example shown in FIG. 9, a liquid crystal device as an output device is represented by an equivalent circuit including a resistor and a capacitor. FIG. 9 shows a storage capacitor 13, a vertical drive circuit 14, and a horizontal drive circuit 15.

(Electrically Conductive Sheet)

Examples of the electrically conductive sheet include sheet organic EL devices, organic thin-film solar cells, dye-sensitized solar cells, and organic thin-film transistors.

<<Functional Organic Compounds>>

The functional organic compound of the present invention is contained in the thin charge transport film layer described above. Specific examples of the functional organic compound include luminescent dopants, host compounds, hole transport materials, electron transport materials, organic solar cell materials, organic thin-film transistor materials, and solvents. The functional organic compound of the present invention is preferably a material that can transport charge carriers (general term including electrons and holes), among these examples.

The one or more types of functional organic compounds having chiral elements of the present invention are contained in the charge-transporting thin film, and the total of the number of chiral elements per molecule in each type of the functional organic compounds, when summed over all types of the functional organic compounds, is four or more.

If any two molecules in the functional organic compounds of the present invention have identical two-dimensional representation of molecular structure, these molecules are regarded as the same type. For example, enantiomers are counted as the same type.

The total of the number of chiral elements per molecule summed over all types of the functional organic compounds is preferably within a range of five to fifteen, in view of increase in entropy.

From the viewpoints of types of compounds, the electronic device of the present invention preferably contains at least two types of the functional organic compounds having chiral elements, and each of the at least two types of the functional organic compounds includes at least one isomer selected from the enantiomers and diastereomers. In another preferred embodiment, the electronic device contains at least two types of the functional organic compounds having chiral elements, and at least one of the functional organic compounds has two or more chiral elements per molecule, and thereby includes both enantiomers and diastereomers.

In another preferred embodiment, the electronic device contains at least two types of the functional organic compounds having chiral elements, at least one of the functional organic compounds is a metal complex; and the metal complex has two or more chiral elements per molecule, and thereby includes both enantiomers and diastereomers. In a further preferred embodiment, the electronic device contains at least two types of the functional organic compounds having chiral elements, and all of the at least two types of the functional organic compounds include two or more chiral elements per molecule, and thereby include both enantiomers and diastereomers.

The one or more types of functional organic compounds preferably have a biaryl structure which has chiral elements due to hindered rotation between two aryl moieties, such that the functional organic compounds include an atropisomer. Such an embodiment is preferred because the functional organic compound includes isomers with identical energy levels.

The term "chiral element due to hindered rotation" refers to a site of bond forming a rotational axis in which free rotation of over 180° is hindered at a normal temperature and under normal pressure. If a molecule has a structure in which a bond forming a rotational axis is hindered in free rotation of over 180° according to its molecular model, the molecule is defined as a molecule having a chiral element due to hindered rotation. A usable molecule model is a Chem-Tutor student modelling system (available from SIGMA-ALDRICH Co.).

The functional organic compound having chiral elements of the present invention is preferably an aromatic hydrocarbon derivative or a heteroaromatic hydrocarbon derivative. The functional organic compounds of the present invention are preferably aromatic hydrocarbon derivatives or heteroaromatic hydrocarbon derivatives, each of which preferably have three or more aromatic rings and/or heteroaromatic rings in total. Examples of the aromatic hydrocarbon derivative include benzene, naphthalene, anthracene, tetracene, pentacene, chrycene, and helicene. Examples of the heteroaromatic hydrocarbon derivative include furan, thiophene, pyrrole, oxazole, thiazole, imidazole, benzofuran, benzothiophene, indole, dibenzofuran, dibenzothiophene, carbazole, pyridine, pyrazine, pyrimidine, and carboline.

The functional organic compounds having chiral elements are preferably contained in a layer within the charge-transporting thin film at a total content of 10% by mass or more, more preferably 20% by mass or more, the most preferably 50% by mass or more.

Specific examples of the functional organic compound will now be described.

(Luminescent Dopant)

The at least one of the functional organic compounds having chiral elements is preferably a compound which emits light by excitation under an electric field. The compound which emits light by excitation under an electric field is preferably a metal complex.

Examples of such a functional organic compound include luminescent dopants.

The luminescent dopant may be a fluorescent dopant or a phosphorescent dopant, and is preferably a phosphorescent dopant.

(Phosphorescent Dopant)

The luminescent dopant is preferably a phosphorescent dopant, from the viewpoint of higher luminous efficiency. The phosphorescent dopant is a compound which can emit light from the excited triplet state and which has a phosphorescence quantum yield of 0.01 or more at 25° C. The phosphorescence quantum yield is preferably 0.1 or more.

A phosphorescent dopant can emit light on the basis of one of the following two mechanisms. One emission mechanism is based on energy transfer, which involves: the recombination of carriers on a host compound onto which the carriers are transferred to produce an excited state of the host compound; and then light emission from a phosphorescent dopant due to transfer of this energy to the phosphorescent dopant. The other emission mechanism is based on a carrier trap, in which a phosphorescent dopant serves as a carrier trap to cause recombination of carriers on the phosphorescent dopant, and thereby light emission from the phosphorescent dopant occurs. In each case, it is essential that the energy in the excited state of the phosphorescent dopant be lower than that in the excited state of the host compound.

The phosphorescent dopant is preferably a metal complex. Examples of the metal complex include those which contain a transition metal as central metal. Specifically, the metal complex preferably contains Cu, Ag, Pd, Rh, Ru, Au, Pt, Ir, or Os, more preferably Cu, Au, Pt, or Ir, as central metal. The metal complex preferably has two or more chiral elements per molecule, and thereby includes both enantiomers and diastereomers.

Preferred examples of the functional organic compound having chiral elements applicable to the present invention as luminescent dopant are as follows.

In the following structural formulae, the symbol "*" represents an asymmetric carbon atom as a chiral element, and the bold line represents a bond axis which is rotationally hindered to be a chiral element.

[Chemical Formula 8]

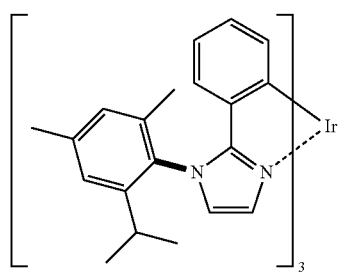

D-101

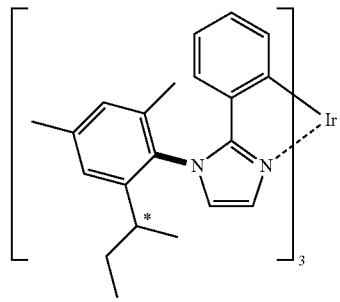

D-102

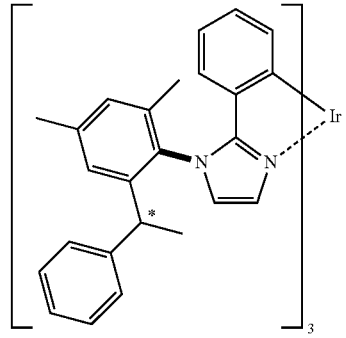

D-103

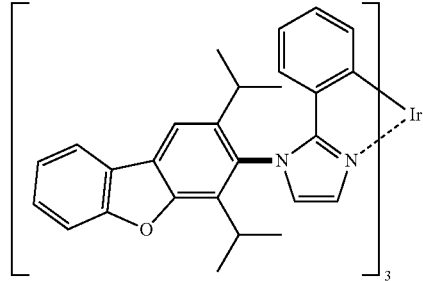

D-104

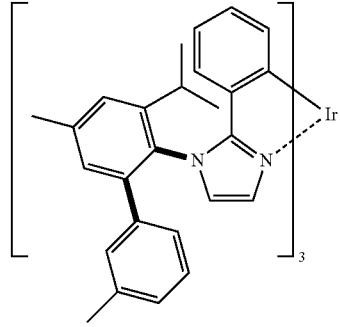

D-105

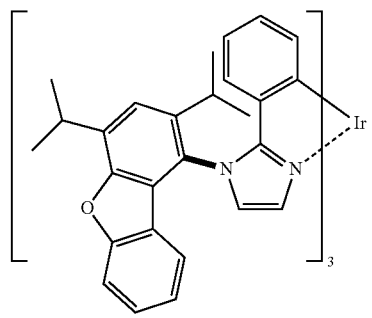

D-106

D-107
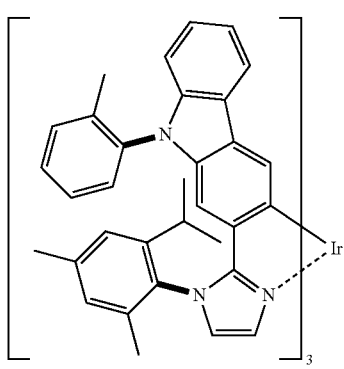
D-108
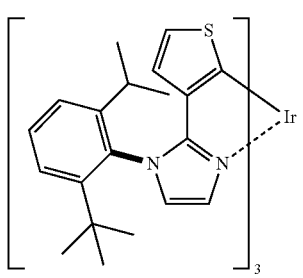
D-109
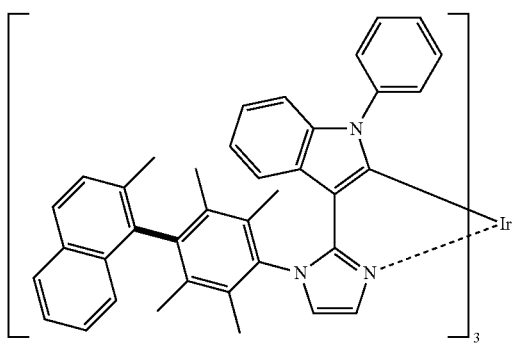
D-110
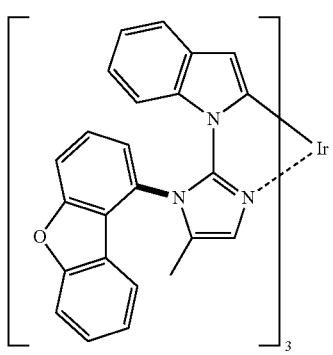
[Chemical Formula 9]
D-111
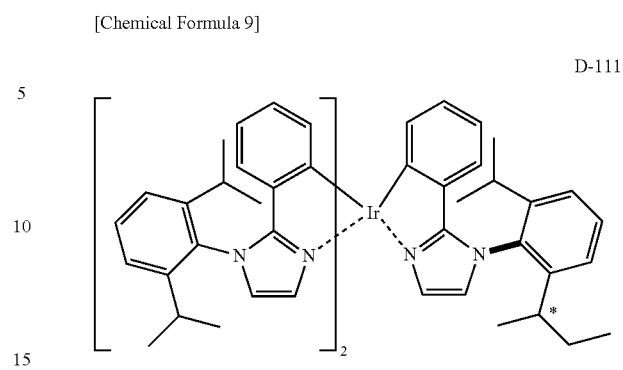
D-112
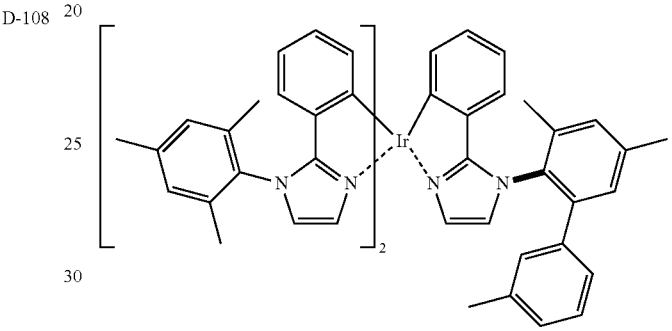
D-113
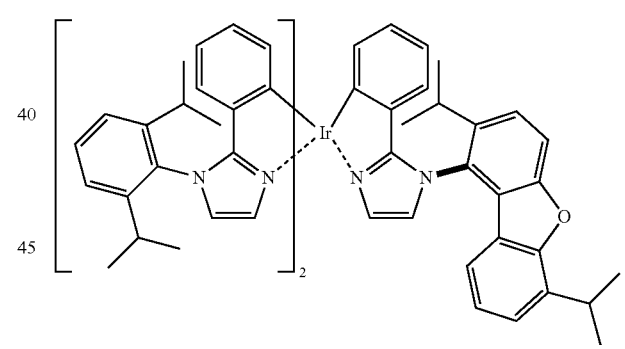
D-114
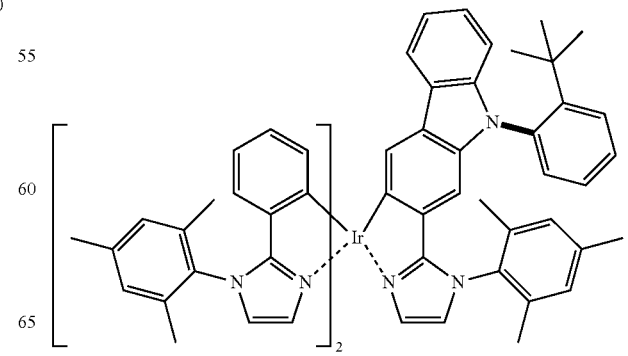

D-115
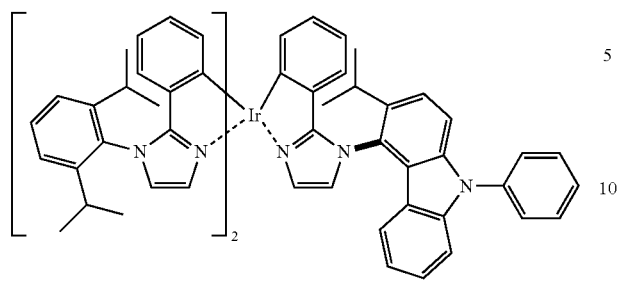
[Chemical Formula 10]
D-116
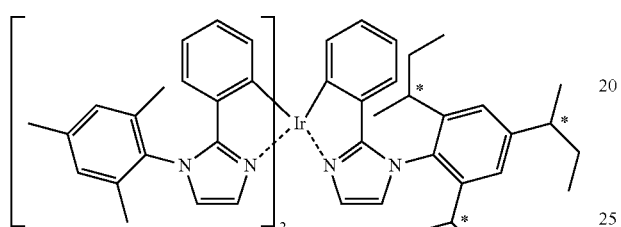
D-117
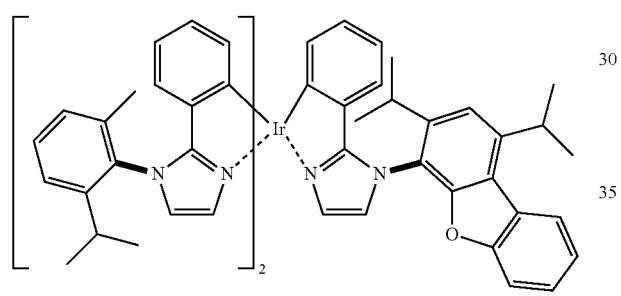
D-118
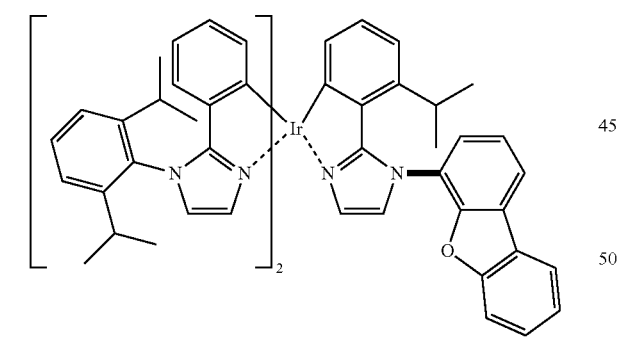
D-119
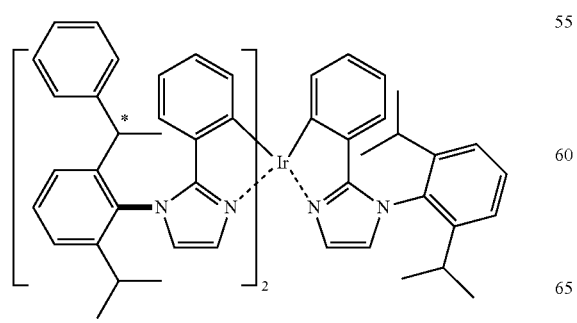
D-120
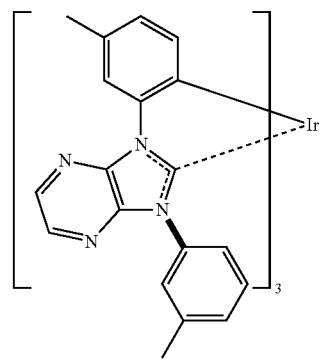
D-121
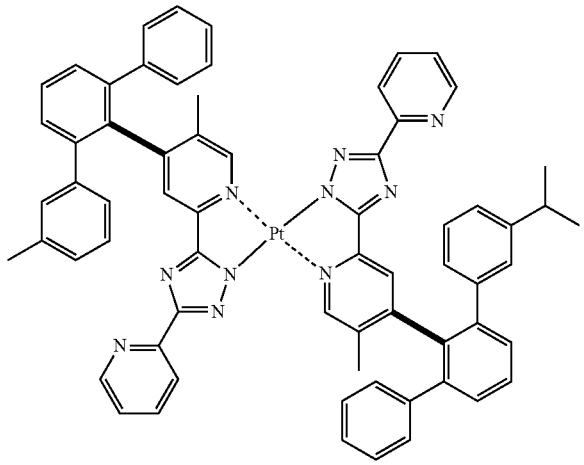
D-122
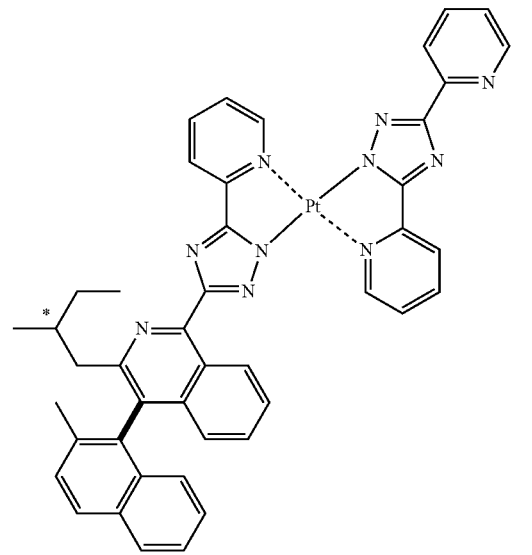

[Chemical Formula 11]

D-123
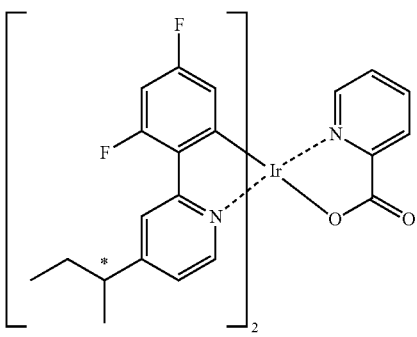

D-124
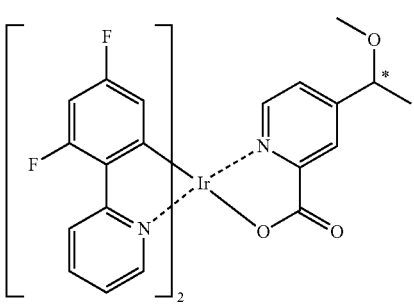

D-125
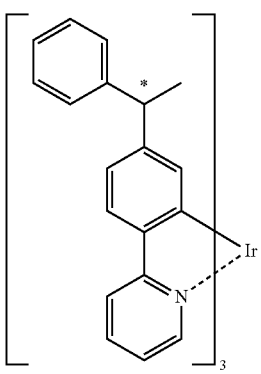

D-126
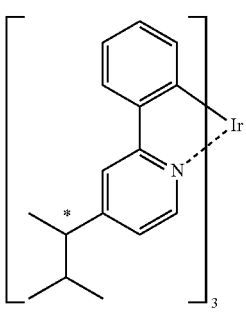

D-127
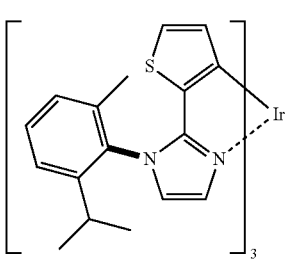

D-128
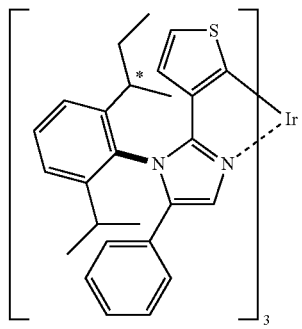

D-129
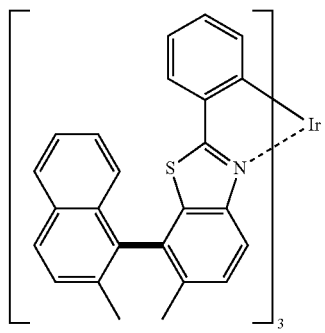

D-130
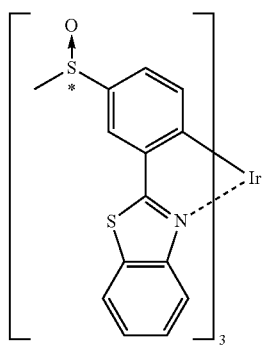

(2) Host Compound

"Host compound" refers to a compound which causes a luminescent dopant to emit light by energy transfer and electron transfer from its excited state to the luminescent dopant. A host compound also has a function to help stable dispersion of a luminescent dopant in a luminous layer.

The luminous efficiency can be increased by a traditional technique using a host compound having a polycyclic aromatic fused ring. Unfortunately, if many host compounds having polycyclic aromatic fused rings are used to increase the luminous efficiency, the host compounds aggregate to cause uneven dispersion of a luminous dopant, resulting in failure to an increase in luminous efficiency and lifetime.

Specifically, conventional film formation of a luminous layer involves a tradeoff between densification of the film with a host compound for an increased lifetime and stable dispersion of luminescent molecules for increased luminous efficiency. Even if intermediate compounds which solve the tradeoff are simply used, there have been limitations in desired improvements in characteristics. Use of a host compound of the present invention can maintain the stability of the luminous layer even if the host compound is contained at high packing density, which achieves both increased luminous efficiency and a prolonged lifetime.

Preferred examples of the functional organic compound having chiral elements applicable to the present invention as a host compound are as follows.
[Chemical Formula 12]
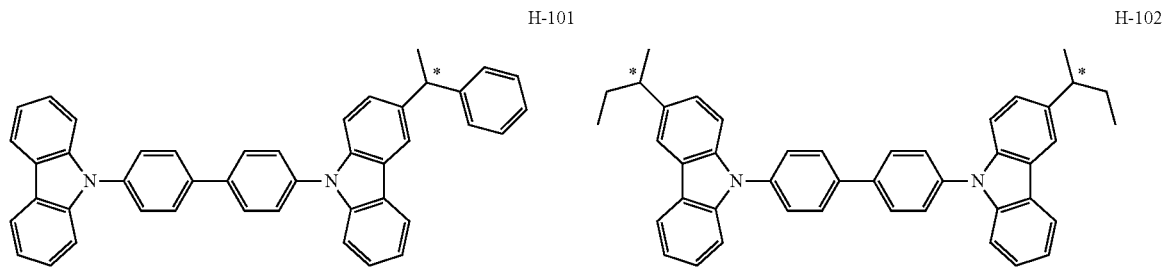
H-101
H-102
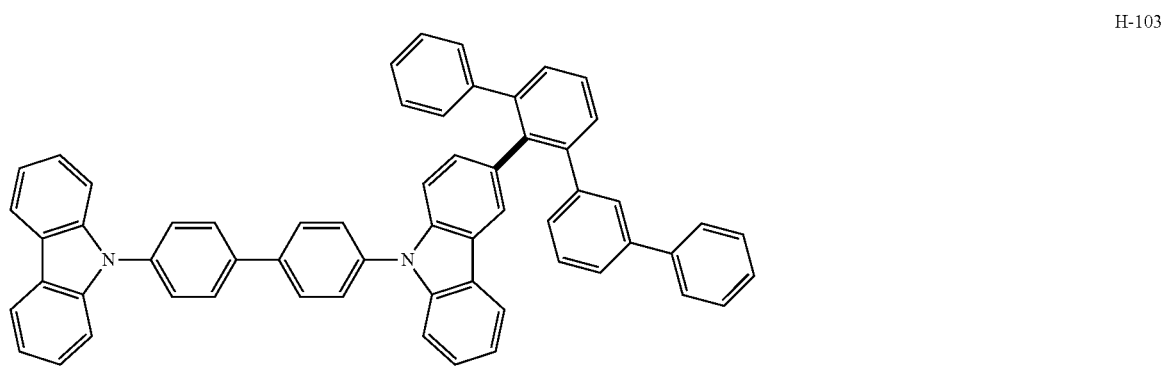
H-103
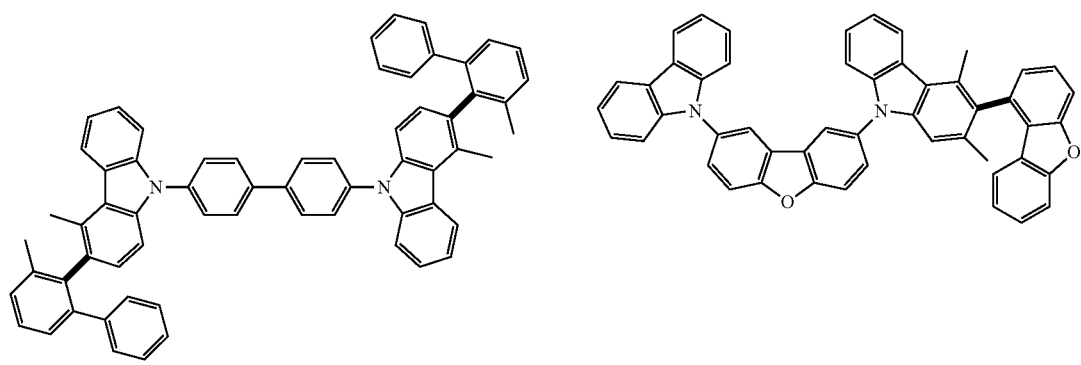
H-104
H-105
[Chemical Formula 13]
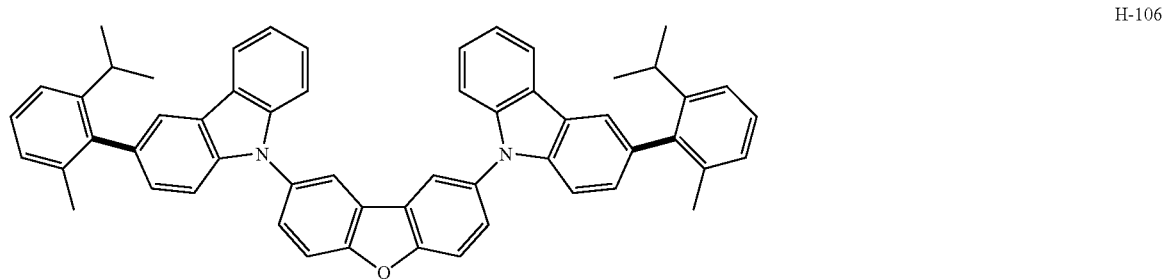
H-106

H-107
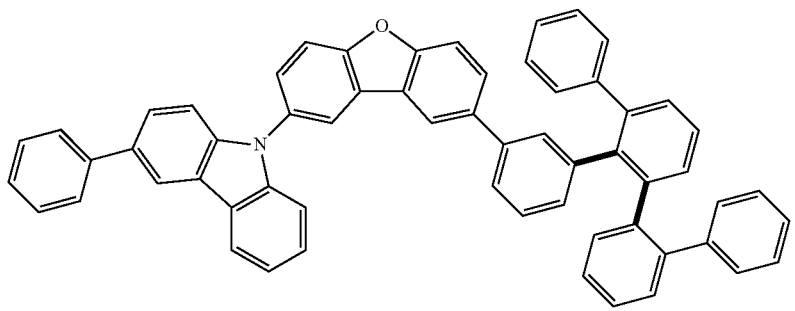
H-108
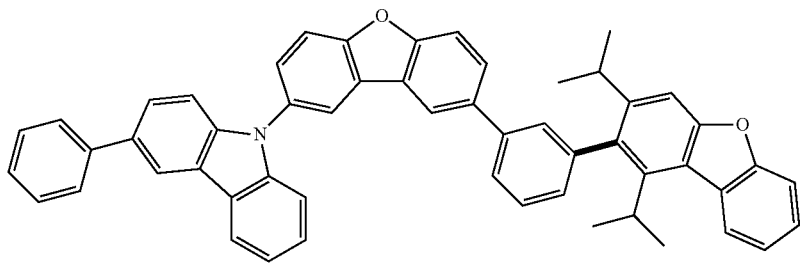
H-109 H-110
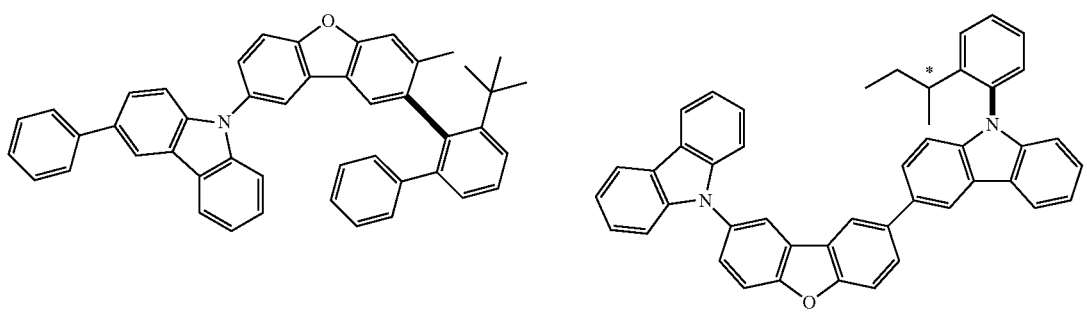
[Chemical Formula 14]
H-111
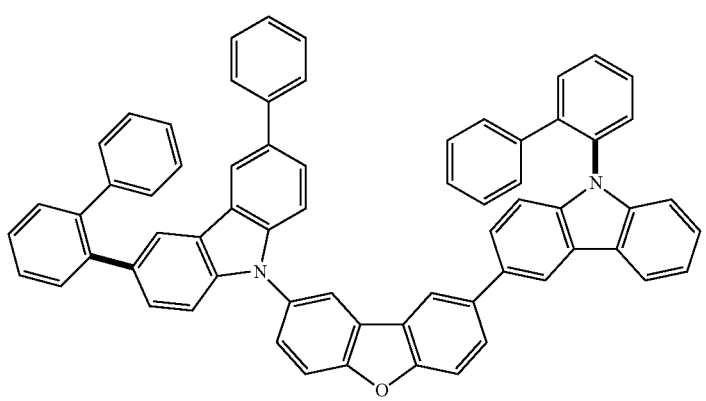
H-112
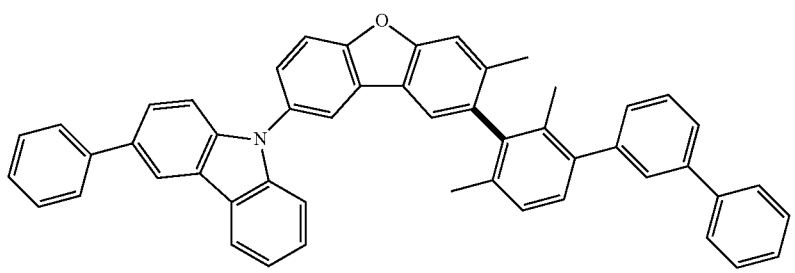

-continued
H-113
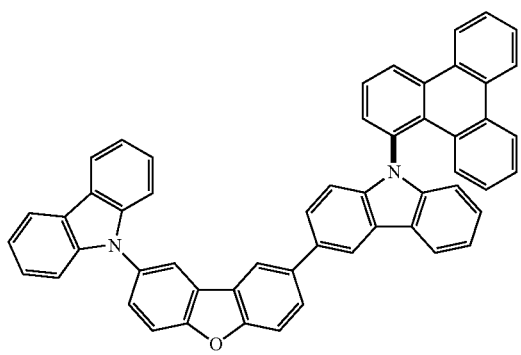
H-114
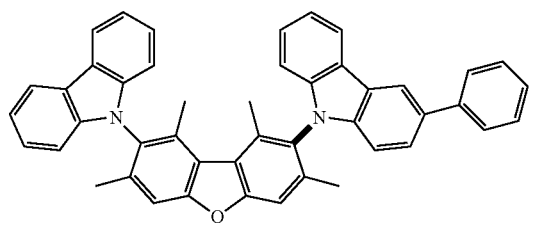
H-115
[Chemical Formula 15]
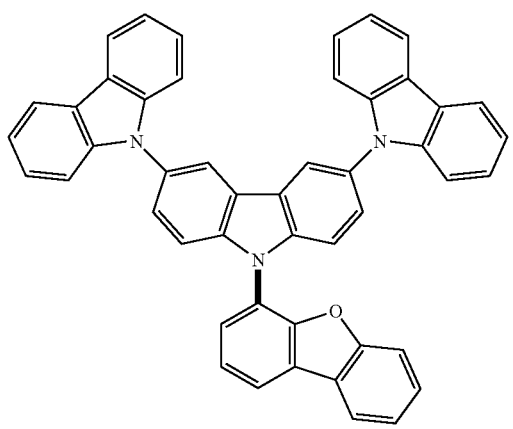
H-116
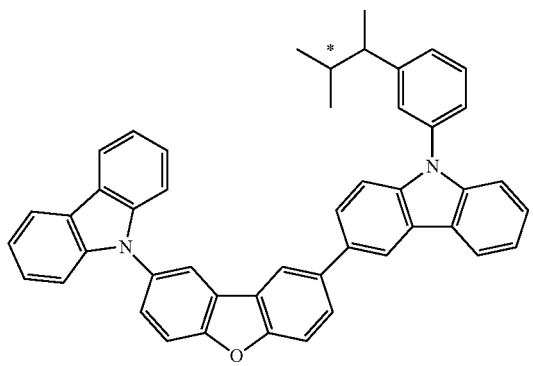
H-117
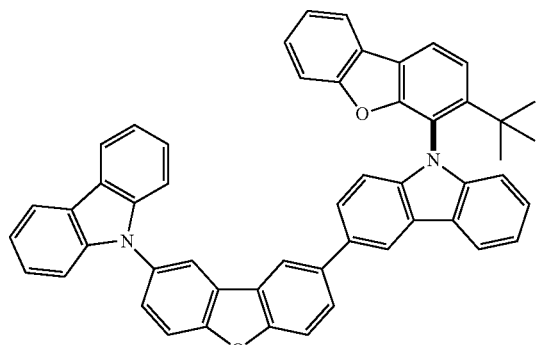
H-118
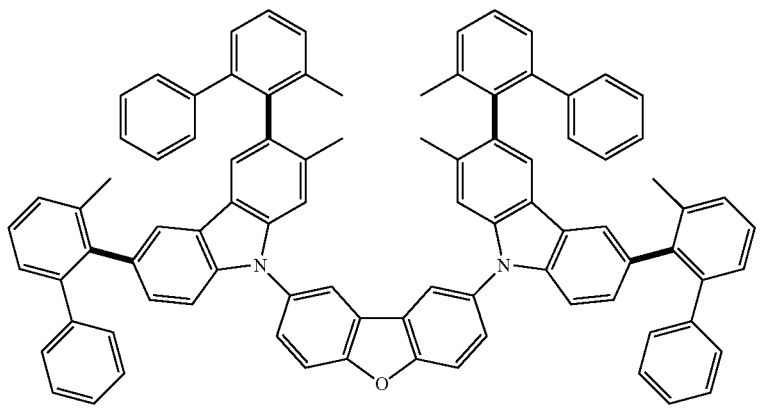

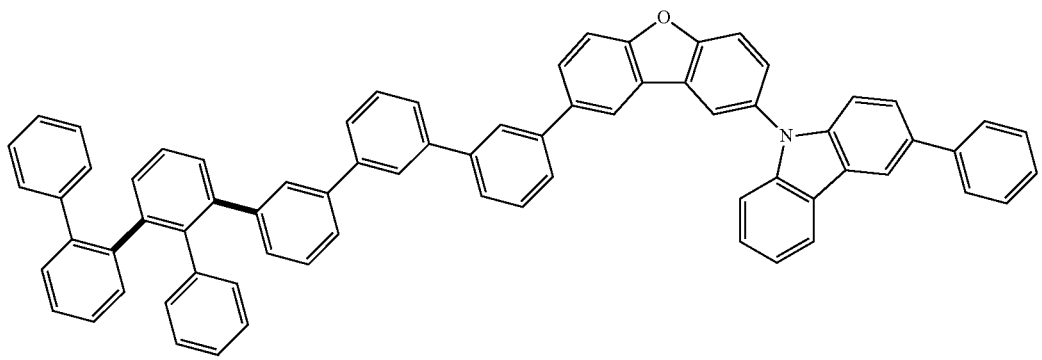

H-119

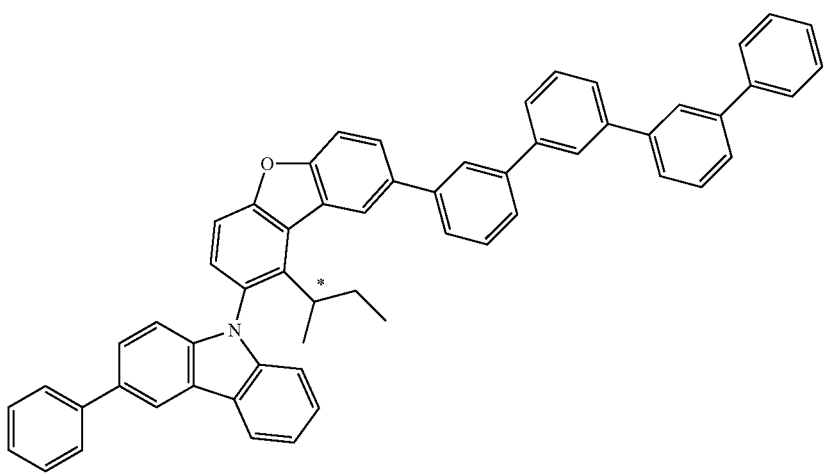

H-120

(Electron Transport Material)

"Electron transport material" refers to materials having electron transportability. A charge-transporting thin film containing such an electron transport material includes an electron transport layer, an electron injection layer, and a hole blocking layer in a broad sense.

Preferred examples of the functional organic compound having chiral elements applicable to the present invention as electron transport material are as follows.

[Chemical Formula 16]

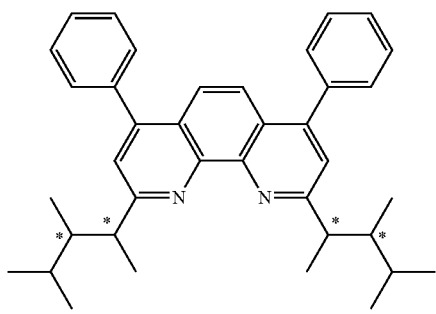

ET-101

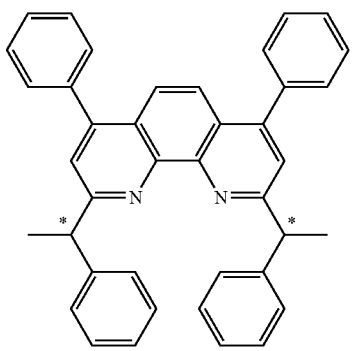

ET-102

-continued
ET-103
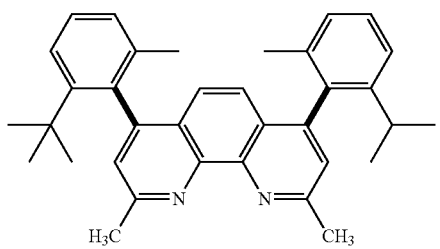
ET-104
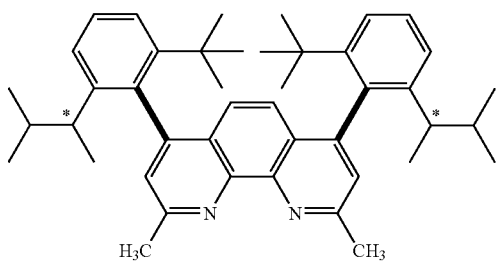
ET-105
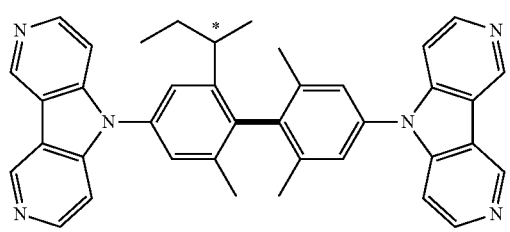
ET-106
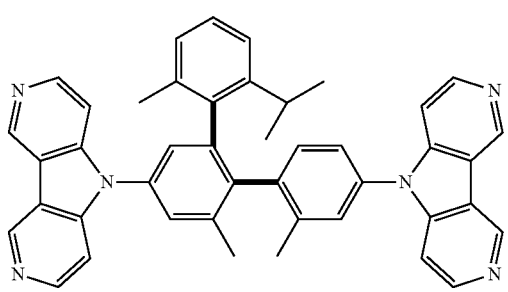
ET-107
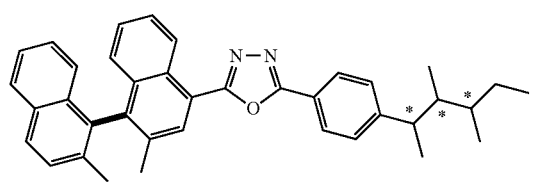
ET-108
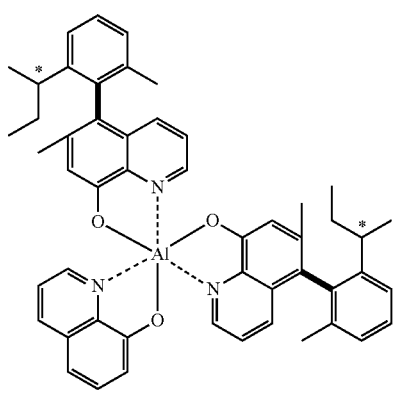
[Chemical Formula 17]
ET-109
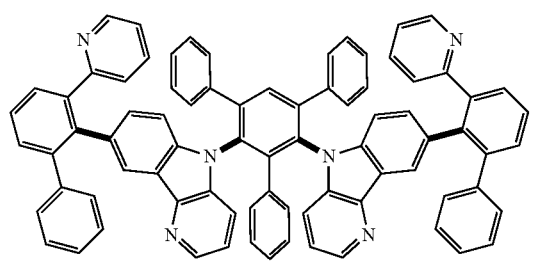
ET-110
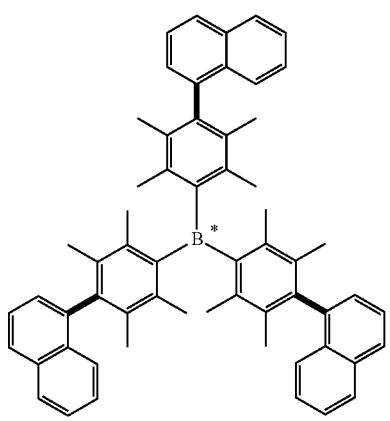

-continued
ET-111
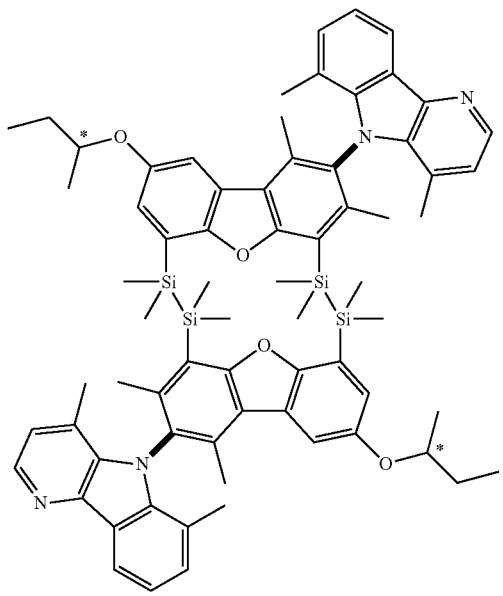
ET-112
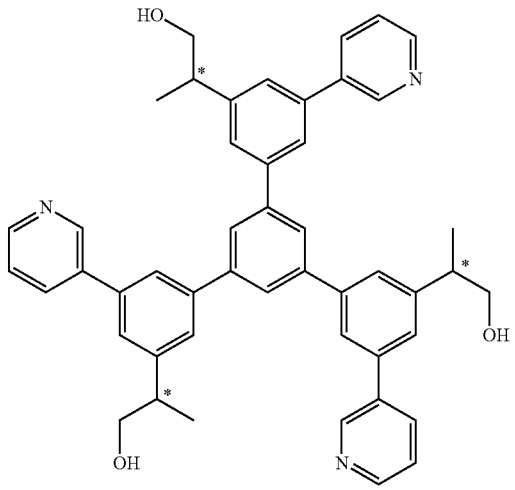
ET-113
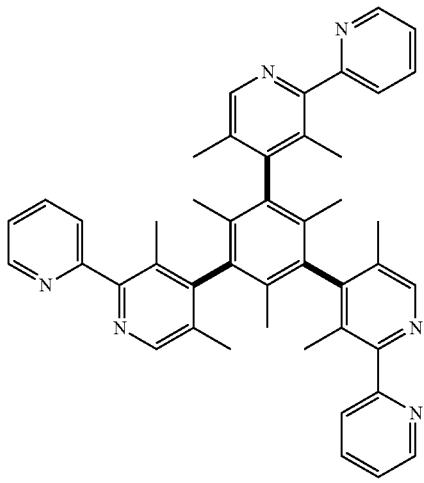
[Chemical Formula 18]
ET-114
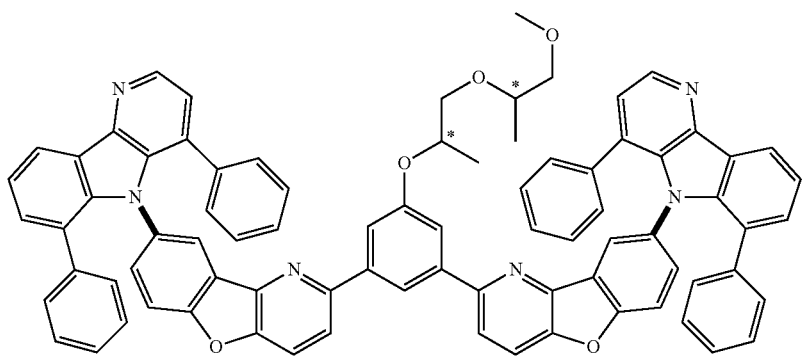

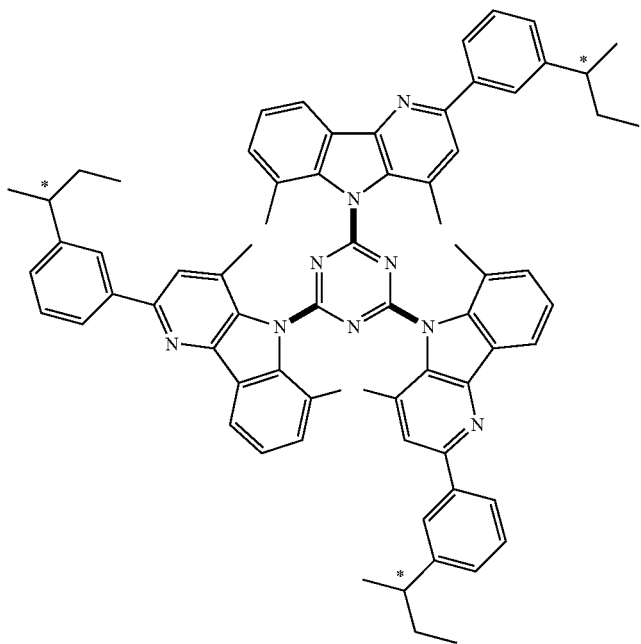

ET-115

(Hole Transport Material)

"Hole transport material" refers to materials having hole transportability. A charge-transporting thin film containing such a hole transport material includes a hole transport layer, a hole injection layer, and an electron blocking layer in a broad sense.

Preferred examples of the functional organic compound having chiral elements applicable to the present invention as hole transport material are as follows.

[Chemical Formula 19]

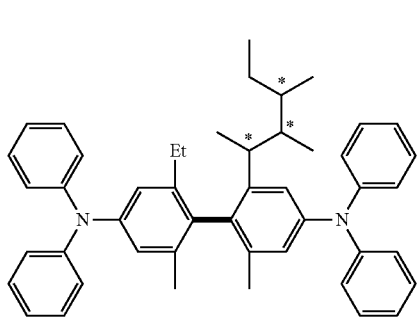

HT-101

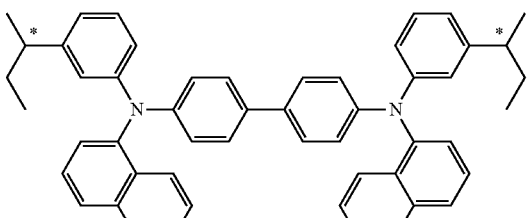

HT-102

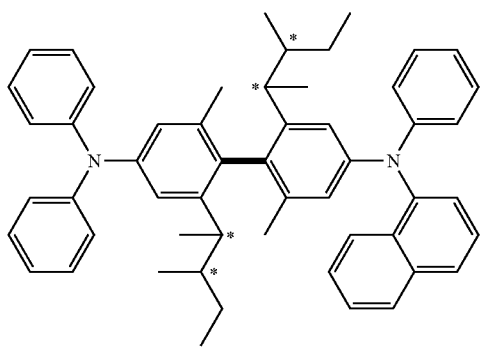

HT-103

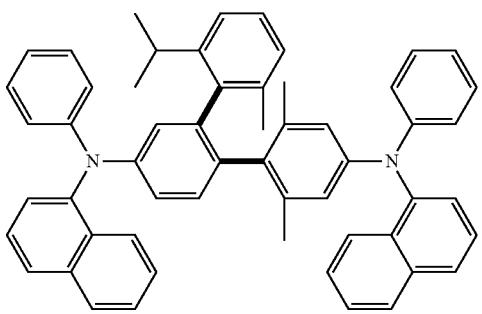

HT-104

-continued
HT-105
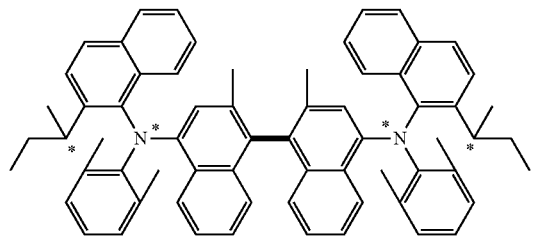
HT-106
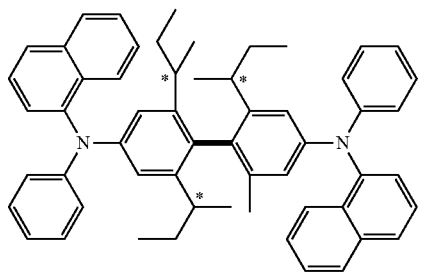
HT-107
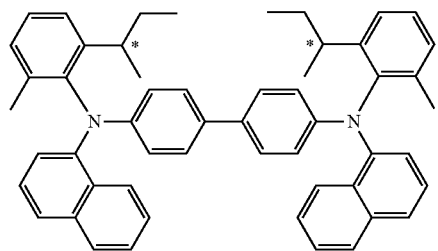
HT-108
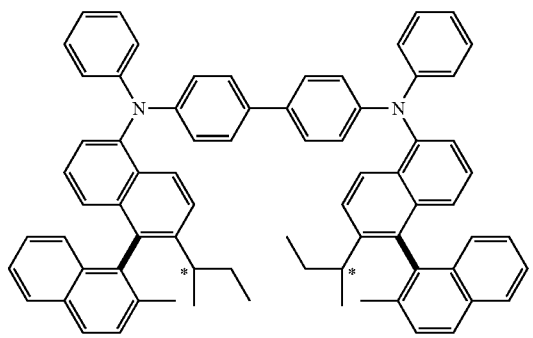
[Chemical Formula 20]
HT-109
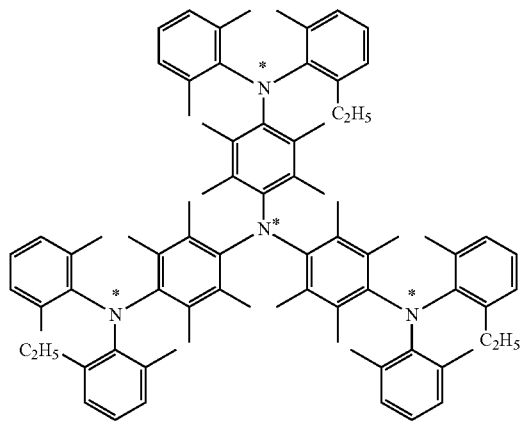
HT-110
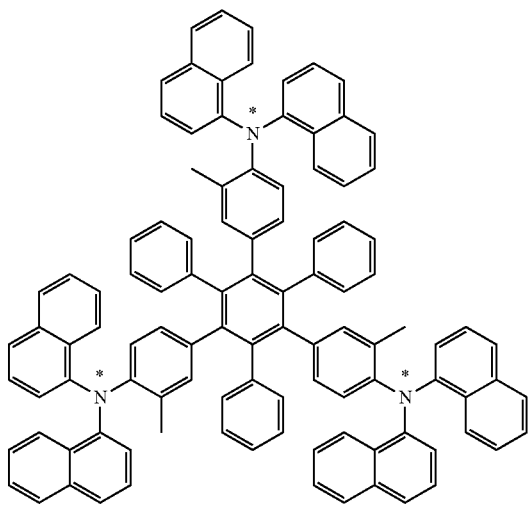
HT-111
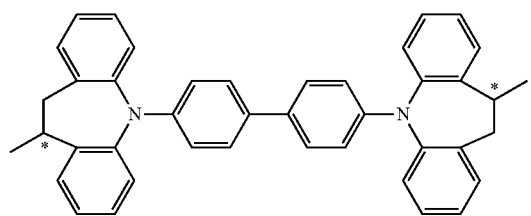
HT-112
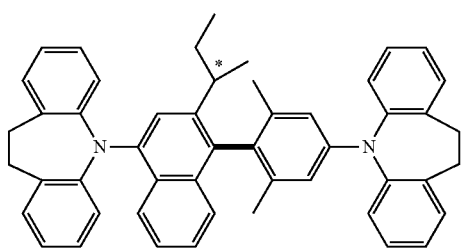
[Chemical Formula 21]
HT-113
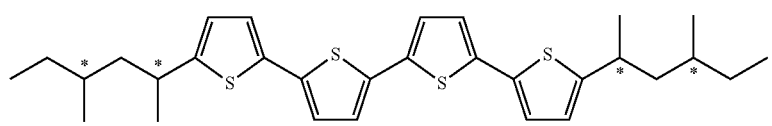

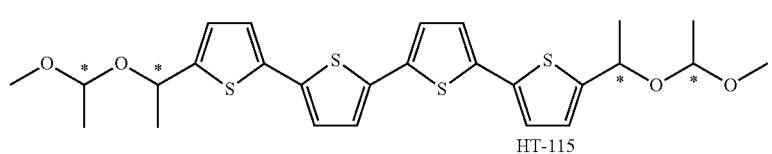
HT-114
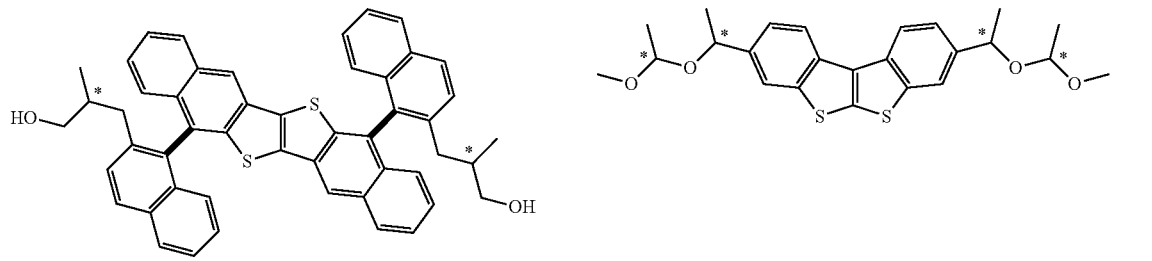
HT-115
HT-116
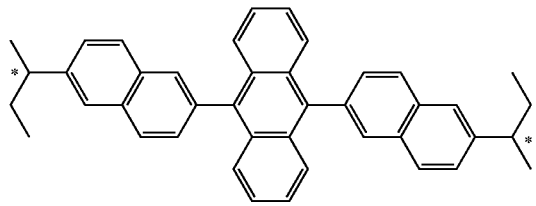
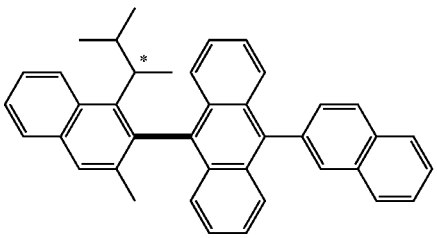
(Fluorescent Material)
Preferred examples of the functional organic compound having chiral elements applicable to the present invention as fluorescent material are as follows.
[Chemical Formula 22]
F-101
F-102
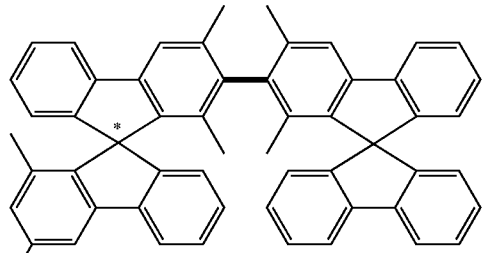
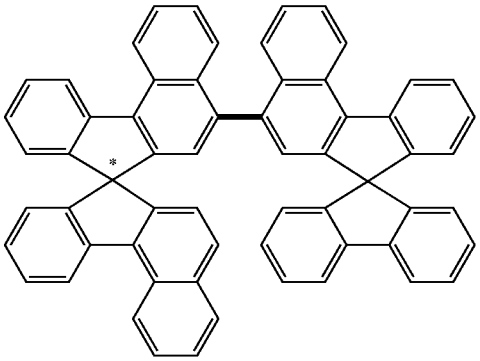
F-103
F-104
F-105
F-106
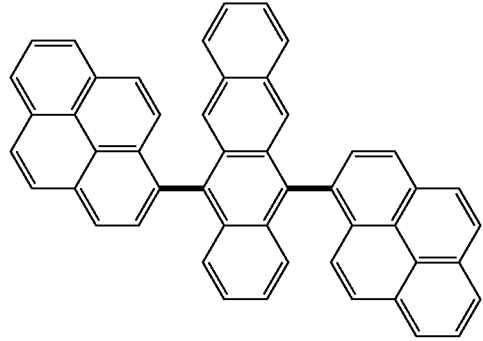
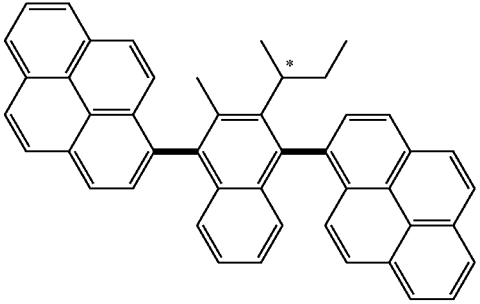

-continued
F-107
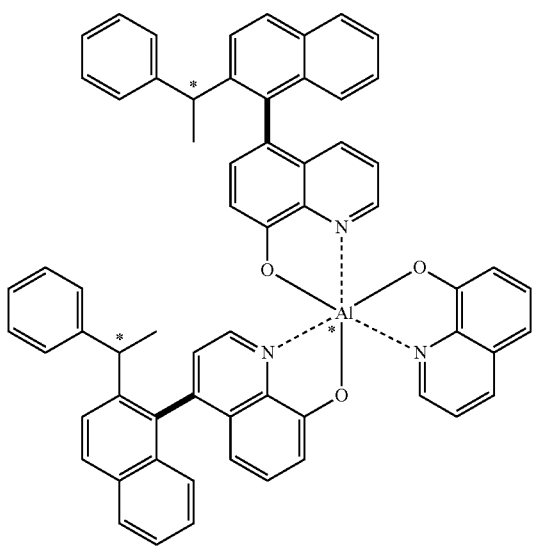
F-108
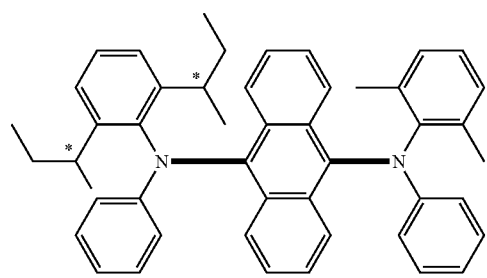
[Chemical Formula 23]
F-109
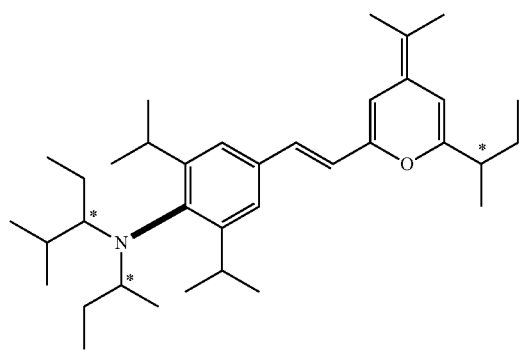
F-110
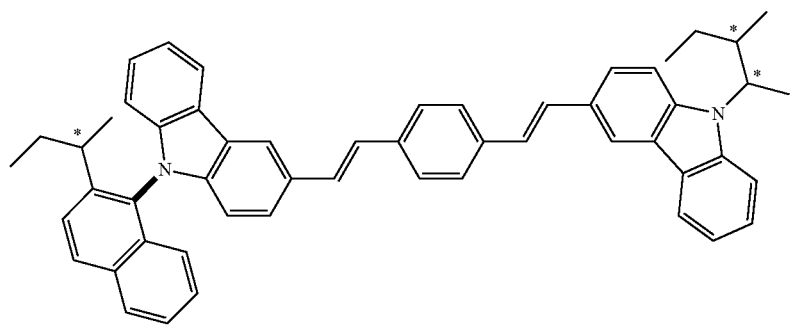
F-111
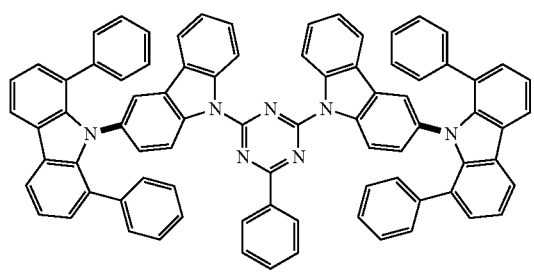
F-112
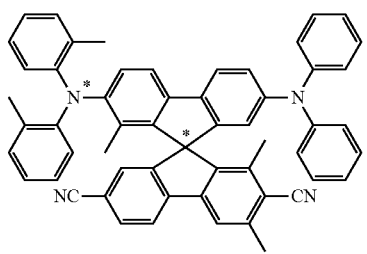

[Chemical Formula 24]
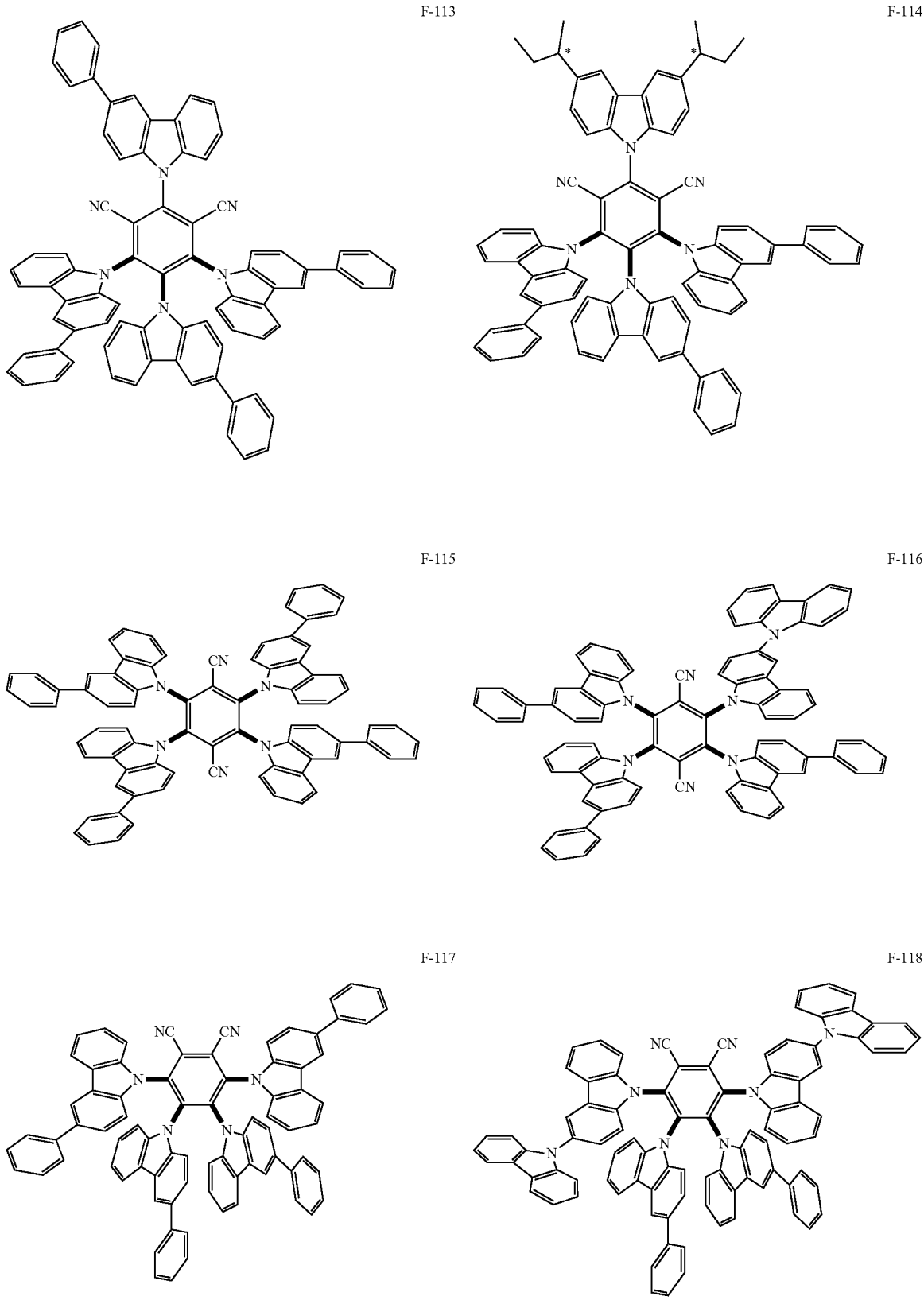

(Organic Solar Cell Material)
Preferred examples of the functional organic compound having chiral elements applicable to the present invention as organic solar cell material are as follows.
[Chemical Formula 25]
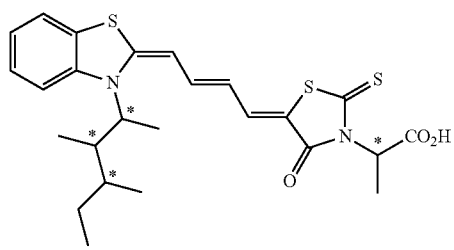
C-201
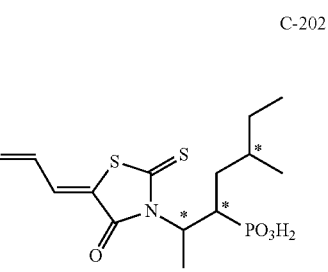
C-202
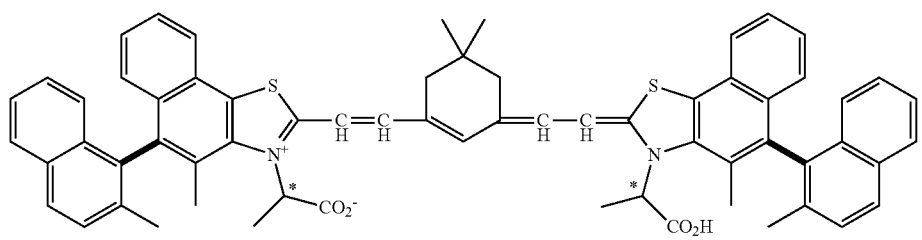
C-203
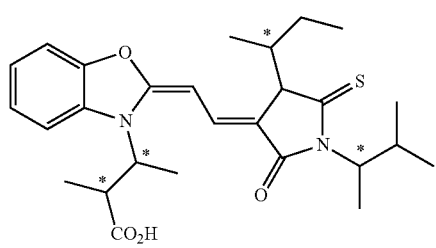
C-204
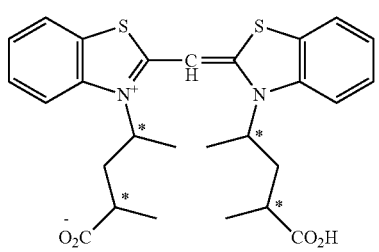
C-205
[Chemical Formula 26]
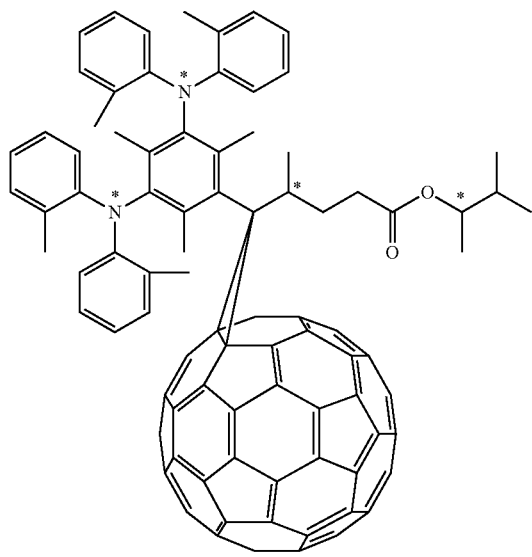
C-101
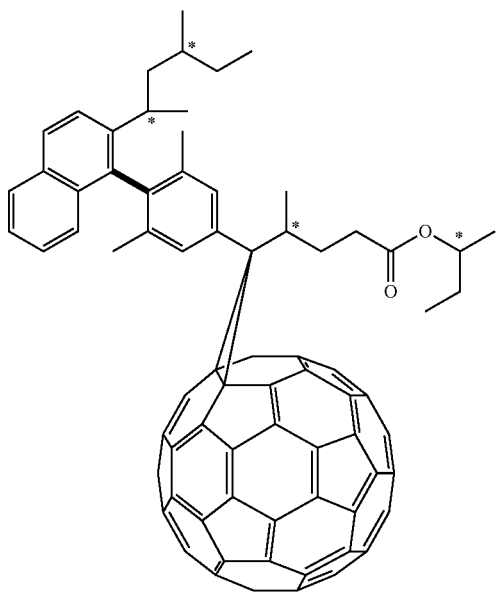
C-102

C-103

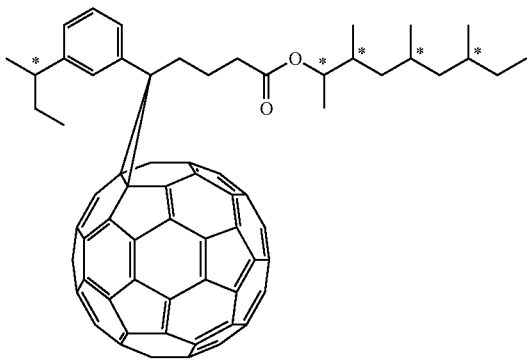

C-104

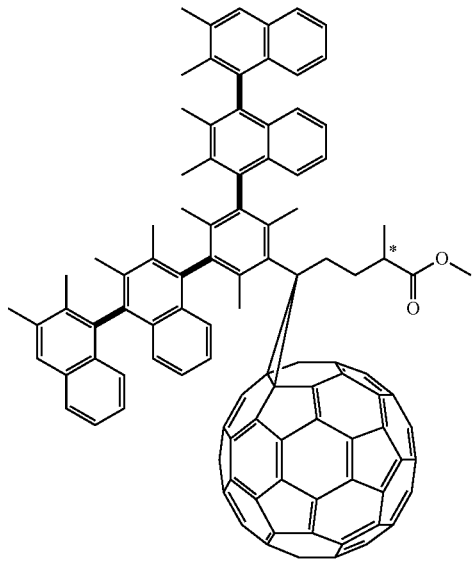

(Solvent)

In a preferred embodiment, the charge-transporting thin film contains the one or more types of functional organic compounds having chiral elements; and a volatile organic material having a boiling point lower than 300° C. under normal pressure, wherein the volatile organic material has an asymmetric carbon atom.

Each of the functional organic compounds contained in the charge-transporting thin film preferably includes a mixture of the enantiomers and diastereomers; the charge-transporting thin film further preferably contains a volatile organic material having a boiling point lower than 300° C. under normal pressure; and the volatile organic material preferably has an asymmetric carbon atom.

Examples of applicable volatile organic material having a boiling point lower than 300° C. under normal pressure and having an asymmetric carbon atom include hydrocarbon solvents having an asymmetric carbon atom. More preferable examples are aliphatic hydrocarbon solvents, aromatic hydrocarbon solvents, and halogen solvents.

Specific examples of the volatile organic material of the present invention include substituted aliphatic hydrocarbon solvents having asymmetric carbon atoms (e.g. acyclic aliphatic hydrocarbon solvent, such as hexane and heptane; cyclic aliphatic hydrocarbon solvent, such as cyclohexane; alcohol solvents, such as methanol, ethanol, n-propanol, and ethylene glycol; ketone solvents, such as acetone and methyl ethyl ketone; and ether solvents, such as diethyl ether, diisopropyl ether, tetrahydrofuran, 1,4-dioxane, and ethylene glycol monomethyl ether); substituted aromatic hydrocarbon solvents having asymmetric carbon atoms (e.g. toluene, xylene, mesitylene, cyclohexylbenzene, and isopropylbiphenyl); and substituted halogen solvents having asymmetric carbon atoms (e.g. methylene chloride, 1,1,2-trichloroethane, and chloroform). More specific examples include 2-ethylhexane, sec-butyl ether, 2-pentanol, 2-methyltetrahydrofuran, 2-propylene glycol monomethyl ether, 2,3-dimethyl-1,4-dioxane, sec-butylbenzene, 4-(sec-butyl)biphenyl, and 2-methylcyclohexylbenzene.

The functional organic compounds of the present invention as described above may be used to form a charge-transporting thin film of the present invention, in combination with any known functional compound corresponding to each function of the layer, provided that the advantageous effect of the present invention is not impaired.

<<Process for Forming Charge-Transporting Thin Film>>

A process for forming the charge-transporting thin film (such as hole injection layer, hole transport layer, electron blocking layer, luminous layer, hole blocking layer, electron transport layer, and electron injection layer) of the present invention will now be described.

The charge-transporting thin film of the present invention may be formed by any conventional method, including vacuum vapor deposition and wet processes.

Examples of the wet process include spin coating, casting, ink jetting, printing, die coating, blade coating, roller coating, spray coating, curtain coating, and Langmuir Blodgett (LB) coating. The charge-transporting thin film of the present invention is preferably formed by a process suitable for a roll-to-roll process, such as die coating, roller coating, ink jetting, or spray coating, from the viewpoints of uniformity and productivity of the layer.

Examples of solvent used to dissolve or disperse the functional organic compounds according to the present invention include ketones, such as methyl ethyl ketone and cyclohexanone; fatty acid esters, such as ethyl acetate; halogenated hydrocarbons, such as dichlorobenzene; aromatic hydrocarbons, such as toluene, xylene, mesitylene, and cyclohexylbenzene; aliphatic hydrocarbons, such as cyclohexane, decaline, and dodecane; and organic solvents, such as DMF and DMSO.

The functional organic compounds can be dispersed by any method, such as ultrasonic wave dispersion, high-shearing force dispersion, or media dispersion.

The individual layers may be deposited by different processes. If a vapor deposition process is employed for film formation, the deposition conditions vary depending on compounds to be used, and are preferably selected appropriately from the following general ranges: a boat heating temperature of 50 to 450° C., a degree of vacuum of $10^{-6}$ to $10^{-2}$ Pa, a deposition rate of 0.01 to 50 nm per second, a substrate temperature of −50 to 300° C., and a layer thickness of 0.1 nm to 5 μm, preferably within the range of 5 to 200 nm.

In production of such a charge-transporting thin film of the present invention, all layers from the hole injection layer to the cathode should preferably be formed in a single vacuuming operation; however, a semi-finished film may be taken out for a different deposition process. In such a case, the process should be performed under a dry inactive gas atmosphere.

The charge-transporting thin film of the present invention containing functional organic compounds may have any appropriate thickness which varies among layers and is preferably within a range of 0.1 nm to 5 μm, preferably within a range of 5 to 200 nm.

<<Anode>>

The anode to apply electric fields to the charge-transporting thin film is preferably composed of an electrode material having a high work function (4 eV or higher, preferably 4.5 V or higher) such as a metal, an alloy, an electrically conductive compound, or a mixture thereof. Specific examples of such an electrode material include metals such as Au; and electrically conductive transparent materials such as CuI, indium-tin oxide (hereinafter, abbreviated as "ITO"), $SnO_2$, and ZnO. Amorphous materials applicable to production of a transparent electrically conductive film, such as IDIXO ($In_2O_3$—ZnO), may also be used.

The anode may also be produced by depositing the electrode material into a thin film by any process such as vapor deposition or sputtering, and then producing a desired pattern by any process such as photolithography. If high patterning accuracy (approximately 100 μm or higher) is not required, the pattern may be formed through a mask having a desired shape by vapor deposition or sputtering of the electrode material.

Alternatively, the film may be formed with a coating material, such as an organic conductive compound, through a wet process, for example, printing or coating. If luminescent light is extracted from the anode, the anode preferably has a transmittance of above 10%. The sheet resistance of the anode is preferably several hundred ohms or lower per sheet.

The thickness of the anode is normally within the range of 10 nm to 1 μm, preferably within the range of 10 to 200 nm, although it depends on the electrode material.

<<Cathode>>

The cathode of the present invention is preferably composed of an electrode material having a low work function (4 eV or lower), such as a metal (referred to as "electron-injecting metal"), an alloy, an electrically conductive compound, or a mixture thereof. Specific examples of such an electrode material include sodium, sodium-potassium alloys, magnesium, lithium, magnesium/copper mixtures, magnesium/silver mixtures, magnesium/aluminum mixtures, magnesium/indium mixtures, aluminum/aluminum oxide ($Al_2O_3$) mixtures, indium, lithium/aluminum mixtures, aluminum, and rare earth metals. From the perspective of electron injection and resistance to oxidation, it is preferable to use a mixture of a metal as an electron-injecting metal and a second metal which is a stable metal with a higher work function than the electron-injecting metal, among these materials. Preferred examples of such a mixture include magnesium/silver mixtures, magnesium/aluminum mixtures, magnesium/indium mixtures, aluminum/aluminum oxide ($Al_2O_3$) mixtures, lithium/aluminum mixtures, and aluminum.

The cathode can be produced by depositing such an electrode material into a thin film using any process, for example, vapor deposition or sputtering. The sheet resistance of the cathode is preferably several hundred ohms or lower per sheet. The thickness of the cathode is normally within the range of 10 nm to 5 μm, preferably within the range of 50 to 200 nm.

After any of the metals exemplified above is deposited into a thin film with a thickness of 1 to 20 nm on a cathode, any of the transparent conductive materials exemplified in the description of the anode is deposited thereon to produce a transparent or translucent cathode. This process can be applied to production of a device having an anode and a cathode that have transparency.

<<Support Substrate>>

The support substrate (hereinafter, also referred to as "substrate" or "support") of the organic EL device, organic thin-film solar cell, and dye-sensitized solar cell of the present invention may be any type of substrate, for example, glass or plastic substrate, and may be transparent or opaque. In the case of an organic EL device, if light is extracted from the support substrate, the support substrate is preferably transparent. Examples of the preferred transparent support substrate include glass, quartz, and transparent resin films. In particular, the support substrate is preferably a resin film which can provide a flexible organic EL device.

Examples of the resin film include polyesters, such as poly(ethylene terephthalate) (PET) and poly(ethylene naphthalate) (PEN); polyethylene; polypropylene; cellophane; cellulose esters and derivatives thereof, such as cellulose diacetate, cellulose triacetate (TAC), cellulose acetate butyrate, cellulose acetate propionate (CAP), cellulose acetate phthalate, and cellulose nitrate; poly(vinylidene chloride); poly(vinyl alcohol); poly(ethylene-vinyl alcohol); syndiotactic polystyrene; polycarbonates; norbornene resins; polymethylpentene; polyether ketone; polyimides; polyethersulfones (PESs); polyphenylene sulfide; polysulfones; polyether imides; polyether ketone imides; polyamides; fluororesins; nylons; poly(methyl methacrylate); acrylics or polyarylates; and cycloolefin resins, such as ARTON (product name; manufactured by JSR) and APEL (product name; manufactured by Mitsui Chemicals, Inc.).

The surface of the resin film may be covered with a coating layer of an inorganic or organic material or a hybrid film of inorganic and organic materials. The resin film is preferably a barrier film having water vapor permeability (measured in accordance with JIS K 7129-1992 (25±0.5° C.; relative humidity: (90±2)% RH)) of $1\times10^{-2}$ g/($m^2 \cdot 24$ h) or lower, and is preferably a high barrier film having oxygen permeability (measured in accordance with JIS K 7126-1987) of $1\times10^{-3}$ $cm^3$/($m^2 \cdot 24$ h·atm) or lower and water vapor permeability of $1\times10^{-5}$ g/($m^2 \cdot 24$ h) or lower.

The barrier film may be composed of any material that can block infiltration of substances, such as moisture and oxygen, which cause deterioration of the electronic device. For example, silicon oxide, silicon dioxide and silicon nitride can be used. In order to prevent the brittleness of the film, the film preferably has a laminated structure composed of one or more inorganic layers and organic layers. The inorganic layers and organic layers may be deposited in any order, preferably alternately.

The barrier film may be formed by any process, for example, vacuum vapor deposition, sputtering, reactive sputtering, molecular beam epitaxy, cluster ion beam deposition, ion plating, plasma polymerization, atmospheric pressure plasma polymerization, plasma chemical vapor deposition (CVD), laser CVD, thermal CVD, and coating. In particular, the gas barrier film is preferably produced by an atmospheric pressure plasma polymerization process as described in Japanese Patent Application Laid-Open Publication No. 2004-68143.

Examples of an opaque support substrate include metal plates such as aluminum plate and stainless steel plate, films, opaque resin substrates, and ceramic substrates.

<<Sealing>>

Examples of a sealing means applicable to the organic EL device, organic thin-film solar cell and dye-sensitized solar cell of the present invention include adhesion of a sealing material, electrodes, and a support substrate with an adhesive. The sealing material may have a concave or flat shape, and transparency and electric insulation are no object.

Specific examples of the sealing material include glass plates, a polymer plate or film, and a metal plate or film. Specific examples of materials for the glass plate include soda-lime glass, barium-strontium-containing glass, lead glass, aluminosilicate glass, borosilicate glass, barium borosilicate glass, and quartz. Examples of materials for the polymer plate include polycarbonates, acrylics, poly(ethylene terephthalate), polyether sulfides, and polyether sulfones. Examples of materials for the metal plate include one or more types of metals or alloys selected from the group consisting of stainless steel, iron, copper, aluminum, magnesium, nickel, zinc, chromium, titanium, molybdenum, silicone, germanium and tantalum.

In the present invention, a polymer film and a metal film may be preferably used as a sealing material. The polymer film preferably has an oxygen permeability (measured in accordance with JIS K 7126-1987) of $1\times10^{-3}$ cm$^3$/(m$^2$·24 h·atm) or lower and a water vapor permeability (measured in accordance with JIS K 7129-1992; 25±0.5° C., relative humidity: (90±2) %) of $1\times10^{-3}$ g/(m$^2$/24 h) or lower.

The sealing material may be processed into a concave shape through any process, for example, sandblasting or chemical etching.

Specific examples of the adhesive for sealing include light-curable or thermosetting adhesives having reactive vinyl groups, such as acrylic acid oligomers and methacrylic acid oligomers; moisture-curable resins, such as 2-cyanoacrylic acid esters; thermosetting and chemically curable adhesives (two-component adhesives), such as epoxy adhesives; hot-melt adhesives, such as polyamide adhesives, polyester adhesives, and polyolefin adhesives; and cation-curable and ultraviolet-curable epoxy resin adhesives.

<<Protective Film and Protective Plate>>

In order to enhance the mechanical strength of the electronic device, a protective film or plate may be provided on the outer face of the sealing film, the outer face being remote from the support substrate across the organic layer. In particular, since sealing with a sealing film does not always ensure high mechanical strength of the electronic device, such a protective film or plate is preferably provided when sealing is processed with the sealing film. Examples of a material usable for such a protective film or plate include the same glass plates, a polymer plate or film, and a metal plate or film as those which can be used for the sealing. A polymer film is preferably used, from the perspective of weight reduction and thinning of the electronic device.

<Example of Impedance Spectroscopic Measurement for Resistance of Thin Film>

In impedance spectroscopy (hereinafter, also referred to as IS), a small-amplitude sinusoidal voltage signal is applied to an organic electroluminescent element, impedance is calculated based on the amplitude and the phase of the current response signal to determine impedance spectrum as a function of frequency of the applied voltage signal.

The impedance thus determined is plotted versus frequency of the applied voltage signal as parameter in a complex plane. Such a plot is referred to as Cole-Cole plot. Basic transfer functions, i.e. modulus, admittance, and permittivity functions, can be determined based on the impedance. A transfer function suitable for the purpose of analysis can be selected from these four transfer functions (see "Impedance Spectroscopy of Organic Electronic Devices", OYO BUTURI, Vol. 76, No. 11 (2007), pp. 1252-1258).

In the present invention, the modulus plot (hereinafter, referred to as "M-plot") was employed. Reciprocals of capacitance components are determined based on the M-plot. In the M-plot, a diameter of an arc-like part of the plot corresponds to a reciprocal of capacitance of a layer, and is proportional to a film thickness. Thus, variations in film thickness can also be detected.

In the IS analysis, in general, an equivalent circuit of an organic electroluminescent element is deduced from the trajectory of the Cole-Cole plot, and a trajectory of the Cole-Cole plot calculated based on the deduced equivalent circuit corresponding to the observed data is retrieved to determine the equivalent circuit.

The IS measurement can be performed with Solartron Impedance Analyzer 1260 and Solartron 1296 dielectric interface (manufactured by Solartron), for example, superimposing an AC voltage of 30 to 100 mVrms (frequency range: 0.1 mHz to 10 MHz) onto a DC voltage.

The equivalent circuit analysis can be performed with ZView software manufactured by Scribner Associates, Inc.

The impedance spectroscopy is applied to determine a resistance of a specific layer in an organic EL device (having the following layer configuration: ITO/HIL (hole injection layer)/HTL (hole transport layer)/EML (luminous layer)/ETL (electron transport layer)/EIL (electron injection layer)/Al). The method of determination is now described. For example, in calculation of the resistance of the electron transport layer (ETL), devices which differ only in the thickness of ETL are produced and compared for M-plot to determine which portion of the curve in the plot corresponds to ETL.

Figure 10:
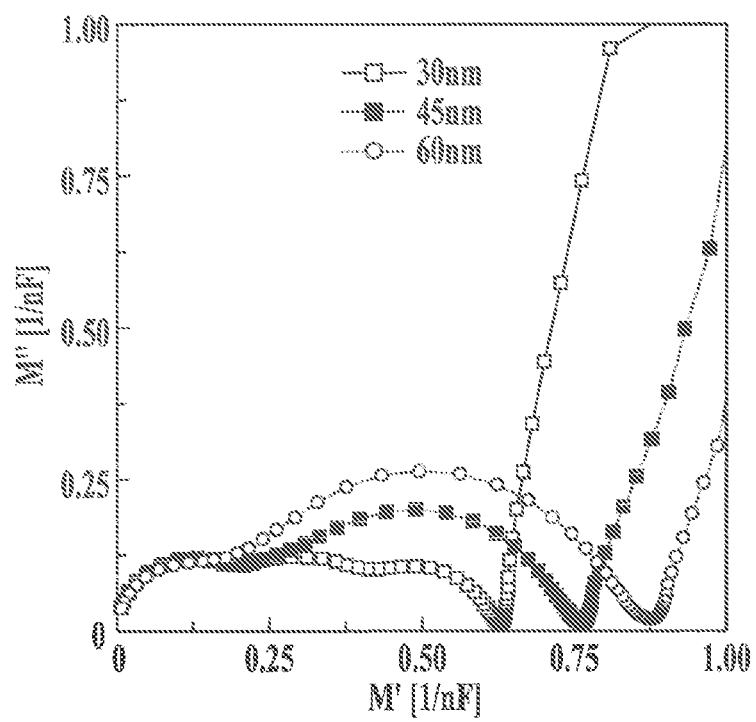
FIG. 10 shows an example of an M-plot of organic EL devices with different thicknesses of the electron transport layer.

FIG. 10 shows an example of an M-plot of organic EL devices with different thicknesses of the electron transport layer, that is, of 30 nm, 45 nm, and 60 nm, respectively. The vertical axis represents the imaginary part M" (1/nF), and the horizontal axis represents the real part M' (1/nF).

Figure 11:
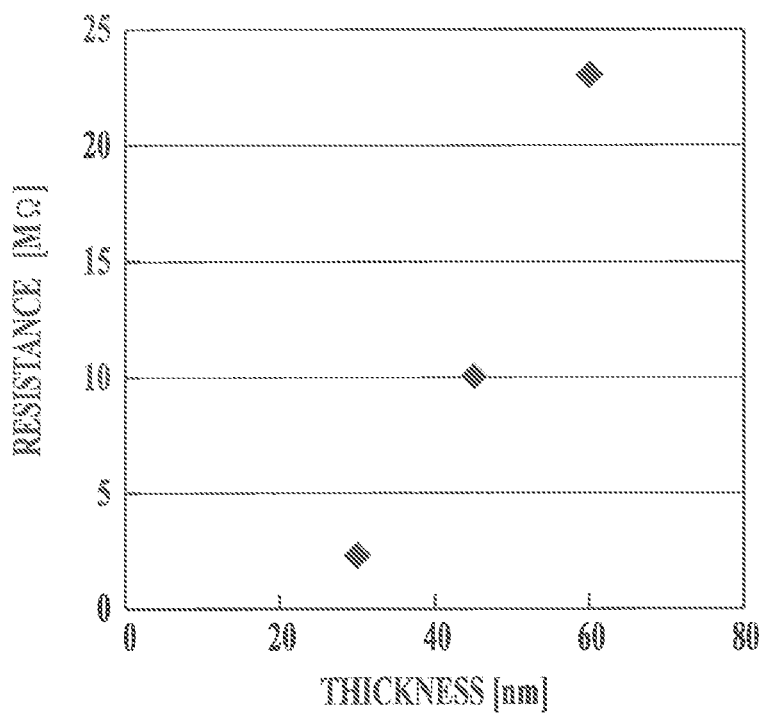
FIG. 11 shows an example relation between the thickness and the resistance of the layer.

The resistance (R) determined from this plots are then plotted versus the thickness of ETL as shown in FIG. 11. Since the plot is almost linear, the resistance value at each layer thicknesses can be determined from the plot.

FIG. 11 shows an example relation between the thickness and the resistance of the ETL. Since the plot is almost linear, the resistance value at each layer thicknesses can be determined based on the relation between the thickness and the resistance of the ETL shown in FIG. 11.

Figure 12:
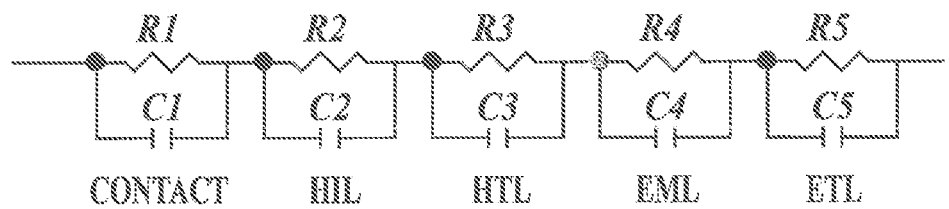
FIG. 12 shows an exemplary equivalent circuit model of the organic electroluminescent element.
Figure 13:
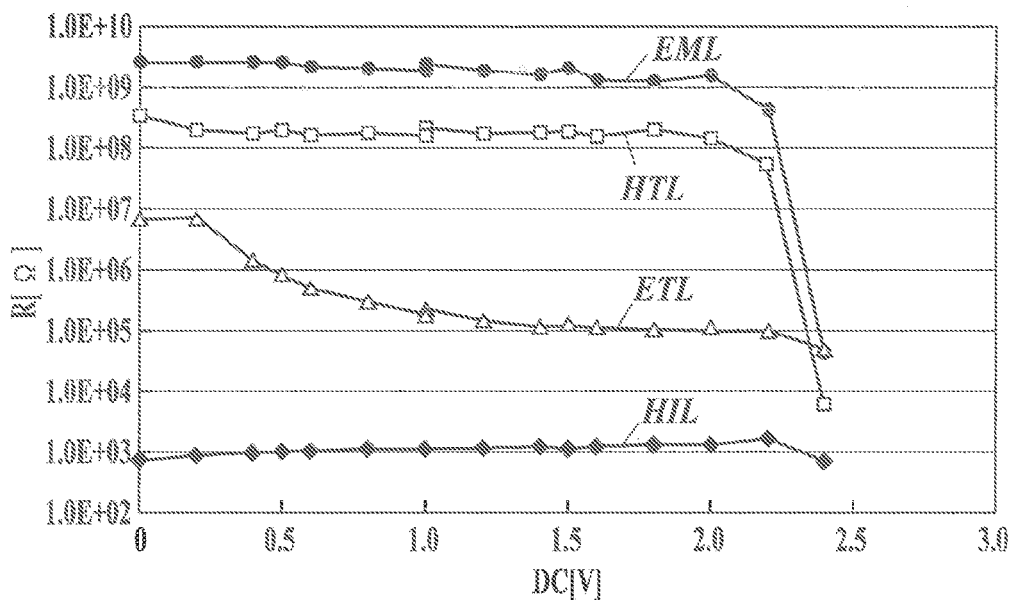
FIG. 13 shows example analytical results indicating the relation between the resistance and the voltage for each layer.

FIG. 12 shows an equivalent circuit model of an organic EL device having the following layer configuration: ITO/HIL/HTL/EML/ETL/Al, and FIG. 13 shows example analytical results for each layer, indicating the relation between the resistance and the voltage for each layer.

Figure 14:
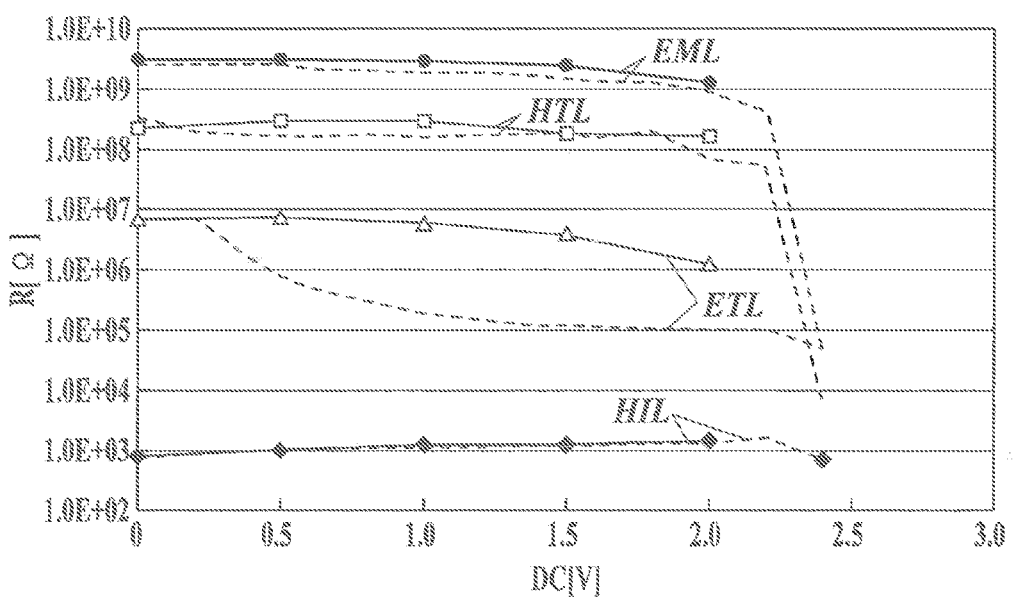
FIG. 14 shows example analytical results of organic EL devices after deterioration.

Meanwhile, the same organic EL device was deteriorated by emitting light for a long time, and was then measured under the same conditions. The results are overlaid with each other, as shown in FIG. 14. The measurement values for each layer at a voltage of 1 V are shown in Table 2. FIG. 14 shows example analytical results of an organic EL device after deterioration.

TABLE 2

|  | HIL(Ω) | ETL(Ω) | HTL(Ω) | EML(Ω) |
|---|---|---|---|---|
| Before driving | 1.1k | 0.2M | 0.2 G | 1.9 G |
| After deterioration | 1.2k | 5.7M | 0.3 G | 2.9 G |

The results indicate that only the ETL in the organic EL device after deterioration has a significantly increased resistance. Specifically, the resistance of the ETL increased to approximately 30 times at a DC voltage of 1 V.

The method described above can be employed to calculate variations in resistance after application of current as described in the Examples of the present invention.

EXAMPLES

The present invention will now be described in more detail by way of Examples. The present invention however should not be limited to these Examples. Throughout the Examples, "part(s)" and the symbol "%" indicate "part (s) by mass" and "% by mass" unless otherwise stated.

The compounds used in the Examples are as follows:

[Chemical Formula 27]

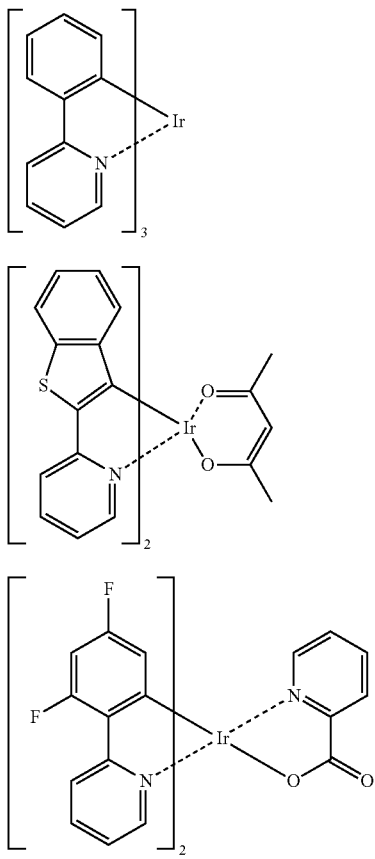

D-1

D-6

D-9

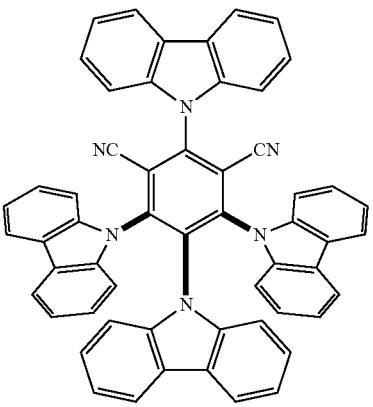

F-01

Compound described in
NATURE 492, pp. 234-240

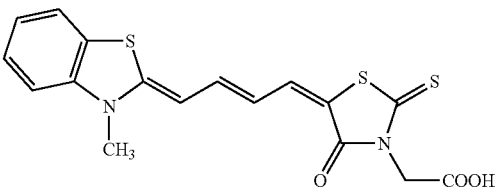

R1

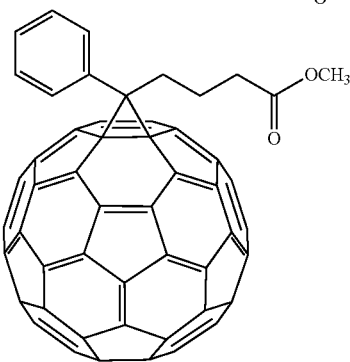

PCBM

Example 1

In the Example below, the charge-transporting thin film is a luminous layer, and the functional organic compounds are a luminescent dopant and a host compound.

<<Preparation of Organic EL Device 1-1>>

Indium tin oxide (ITO) with a thickness of 100 nm was deposited on a glass substrate with dimensions of 100 mm by 100 mm by 1.1 mm (NA 45 manufactured by NH Technoglass Corporation) and was patterned into an anode. A transparent support substrate provided with the transparent ITO electrode was ultrasonically cleaned in isopropyl alcohol, was dried in a dry nitrogen stream, and then was cleaned in a UV ozone environment for five minutes.

A solution of 70% poly(3,4-ethylene dioxythiophene)-polyethylenesulfonate (hereinafter, referred to as PEDOT/PSS; Baytron P Al 4083 available from Bayer) in pure water was applied by spin coating on the transparent support substrate at 3000 rpm for 30 seconds. The coating film was dried at 200° C. for one hour. A hole injection layer with a thickness of 20 nm was thereby formed.

The transparent support substrate was fixed to a substrate holder in a commercially available vacuum vapor deposition system, and 200 mg of α-NPD (4,4'-bis[N-(1-naphthyl)-N-phenylamino]biphenyl) was placed onto a molybdenum resistive heating boat, 200 mg of CBP (4,4'-N,N'-dicarbazole-biphenyl) was placed onto another molybdenum resistive heating boat, 200 mg of compound D-9 was placed onto another molybdenum resistive heating boat, and 200 mg of BCP (2,9-dimethyl-4,7-diphenyl-1,10-phenanthroline) was placed onto another molybdenum resistive heating boat. The molybdenum resistive heating boats were then placed in the vacuum vapor deposition system.

After evacuation of the vacuum vessel to $4\times10^{-4}$ Pa, the heating boat containing α-NPD was electrically heated to deposit α-NPD onto the hole injection layer at a deposition rate of 0.1 nm/sec. A hole transport layer with a thickness of 30 nm was thereby formed.

The heating boats respectively containing CBP and D-9 were electrically heated to codeposit CBP and D-9 onto the hole transport layer at deposition rates of 0.1 nm/sec and 0.010 nm/sec, respectively. A luminous layer with a thickness of 40 nm was thereby formed.

The heating boat containing BCP was then electrically heated to deposit BCP onto the hole blocking layer at a deposition rate of 0.1 nm/sec. An electron transport layer with a thickness of 30 nm was thereby formed.

Subsequently, lithium fluoride was deposited into a thickness of 0.5 nm to form a cathode buffer layer, and then aluminum was deposited into a thickness of 110 nm to form a cathode. The organic EL device 1-1 was thereby prepared.

<<Preparation of Organic EL Devices 1-2 to 1-52>>

The organic EL devices 1-2 to 1-52 were prepared as in the organic EL device 1-1, except that CBP and D-9 were replaced with the individual compounds described in Table 1.

<<Evaluation of Organic EL Devices 1-1 to 1-52>>

Figure 15:
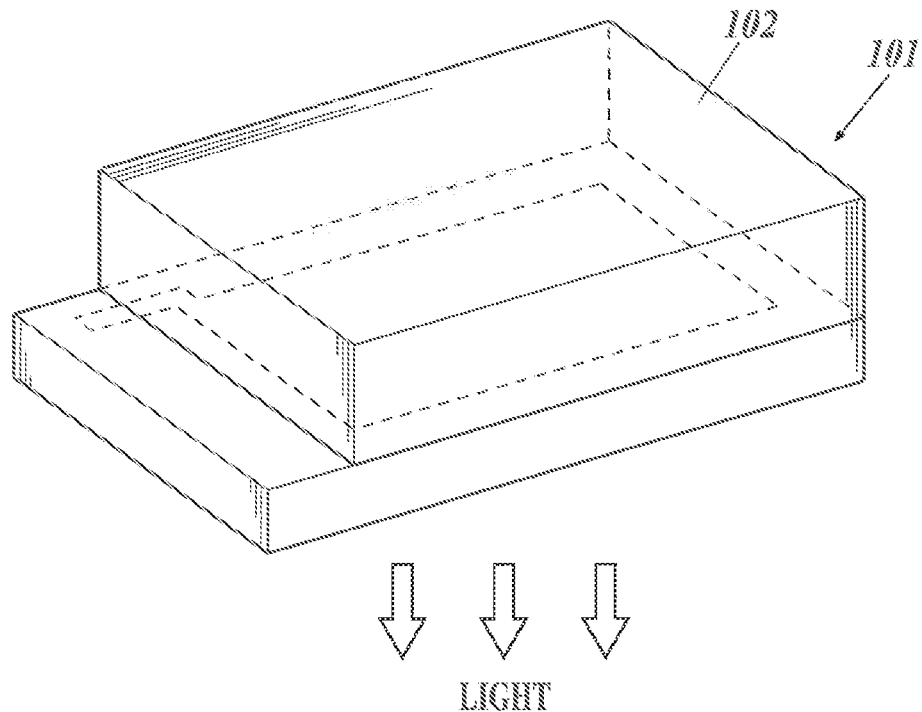
FIG. 15 is a diagrammatic view of a lighting device.
Figure 16:
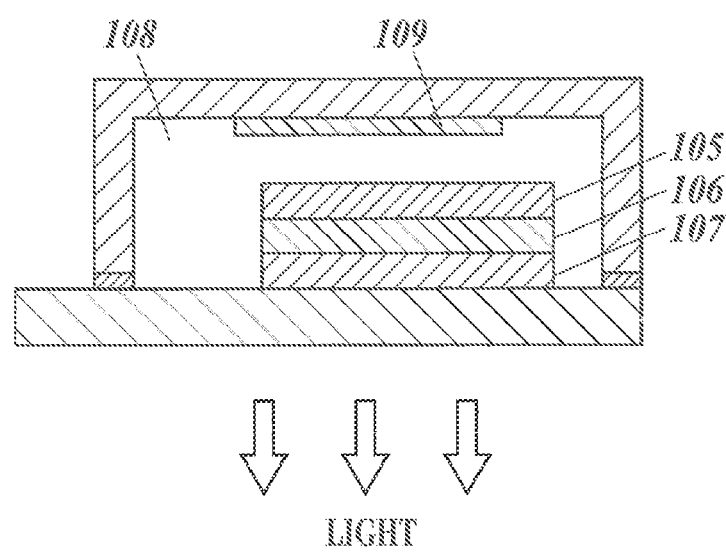
FIG. 16 is a cross-sectional view of the lighting device.
Figure 17A:
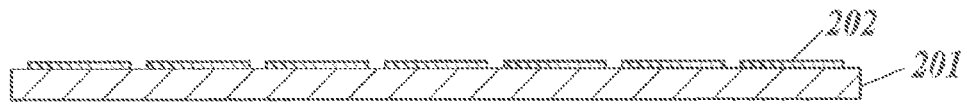
FIG. 17A is a diagrammatic view illustrating a structure of an organic EL full-color display device.
Figure 17B:
FIG. 17B is a diagrammatic view illustrating a structure of an organic EL full-color display device.
Figure 17C:
FIG. 17C is a diagrammatic view illustrating a structure of the organic EL full-color display device.
Figure 17D:
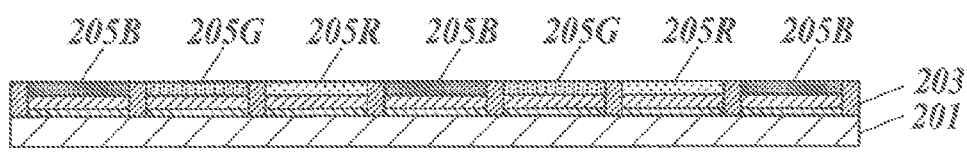
FIG. 17D is a diagrammatic view illustrating a structure of the organic EL full-color display device.
Figure 17E:
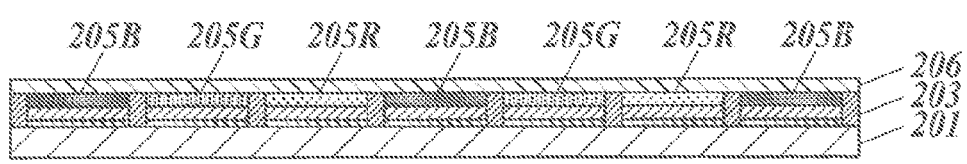
FIG. 17E is a diagrammatic view illustrating a structure of the organic EL full-color display device.

For evaluation of the resulting organic EL devices, lighting devices shown in FIG. 15 and FIG. 16 were produced with the organic EL devices, and were analyzed for variations in resistance of the luminous layer as measured with an impedance spectrometry system and in half-width of the emission spectrum of the organic EL device.

FIG. 15 is a diagrammatic view of a lighting device. The organic EL device 101 of the present invention is covered with a glass case 102 (sealing with the glass case 102 is performed under a high-purity (99.999% or higher) nitrogen gas atmosphere in a glovebox to avoid exposure of the organic EL device 101 to the air). Specifically, an epoxy photo-curable adhesive (LUXTRACK LC0629B, manufactured by TOAGOSEI CO., LTD.) as a sealant was applied onto the periphery of the glass case, where the glass case is in touch with the glass substrate provided with the organic EL device. The glass case was attached on the transparent support substrate to cover the cathode. The adhesive was then cured by irradiation with UV light incident on the side of the glass substrate, except the organic EL device.

FIG. 16 is a cross-sectional view of the lighting device that includes a cathode 105, an organic EL layer 106, and a glass substrate 107 provided with a transparent electrode. The interior of the glass cover 102 is filled with nitrogen gas 108 and is provided with a water-trapping agent 109.

(1) Variation in Resistance after Driving the Organic EL Device

The individual organic EL devices prepared as described above were subjected to measurement of resistance of the luminous layer at a bias voltage of 1 V with Solartron Impedance Analyzer 1260 and Solartron 1296 dielectric interface (manufactured by Solartron), based on the method described in "Hakumaku no Hyoka Handbook (Handbook of Thin Film Characterization Technology)" (published by Technosystem Co., Ltd.) on pages 423 to 425.

The individual organic EL devices were driven for 1000 hours under a constant current density of 2.5 mA/cm² at room temperature (25° C.), and were subjected to measurement of the resistance of the luminous layer before and after the driving of the device. Based on the observed results, a variation in resistance was calculated for each organic EL device by the expression below. Table 3 shows the variation in resistance of the individual organic EL devices as a relative value to that (set as 100) of the organic EL device 1-1.

Variation in resistance between before and after the driving=$Abs$[{(resistance after the driving)/(resistance before the driving)}−1]×100

The expression indicates that the variation in resistance between before and after the driving decreases as the value approaches 0.

(2) Variation in Half-Width of the Emission Spectrum of the Organic EL Device Between Before and after the Driving The individual organic EL devices were driven for 1000 hours under a constant current density of 2.5 mA/cm² at room temperature (25° C.), and were subjected to measurement of the emission spectrum before and after the driving of the device with a spectroradiometer CS-1000 (available from Konica Minolta, Inc.). A variation in half-width to the peak wavelength was calculated for each organic EL device by the expression below. Table 3 shows the variation in half-width of the individual organic EL devices as a relative value to that (set as 100) of the organic EL device 1-1.

Variation in half-width between before and after the driving=$Abs$[{(half-width after the driving)/(half-width before the driving)}−1]×100

The expression indicates that the variation in half-width between before and after the driving decreases as the value approaches 0.

TABLE 3

| Device No. | Host | Luminescent dopant | Variation in resistance of luminous layer (relative value) | Variation in half-width (relative value) | Total number of chiral elements | Remarks |
|---|---|---|---|---|---|---|
| 1-1 | CBP | D-9 | 100 | 100 | 1 | *1 |
| 1-2 | CBP | D-111 | 92 | 80 | 3 | *1 |
| 1-3 | H-104 | D-9 | 88 | 102 | 3 | *1 |
| 1-4 | H-104 | D-101 | 11 | 41 | 6 | *2 |
| 1-5 | H-104 | D-102 | 12 | 32 | 9 | *2 |
| 1-6 | H-104 | D-103 | 11 | 30 | 9 | *2 |
| 1-7 | H-104 | D-104 | 6 | 42 | 6 | *2 |
| 1-8 | H-104 | D-105 | 5 | 48 | 9 | *2 |
| 1-9 | H-104 | D-106 | 9 | 38 | 6 | *2 |

TABLE 3-continued

| Device No. | Host | Luminescent dopant | Variation in resistance of luminous layer (relative value) | Variation in half-width (relative value) | Total number of chiral elements | Remarks |
|---|---|---|---|---|---|---|
| 1-10 | H-104 | D-107 | 9 | 42 | 9 | *2 |
| 1-11 | H-104 | D-108 | 13 | 48 | 6 | *2 |
| 1-12 | H-104 | D-109 | 14 | 38 | 6 | *2 |
| 1-13 | H-104 | D-110 | 13 | 35 | 6 | *2 |
| 1-14 | H-104 | D-111 | 10 | 33 | 5 | *2 |
| 1-15 | H-104 | D-112 | 6 | 47 | 4 | *2 |
| 1-16 | H-104 | D-113 | 13 | 36 | 4 | *2 |
| 1-17 | H-104 | D-114 | 7 | 38 | 4 | *2 |
| 1-18 | H-104 | D-115 | 8 | 45 | 4 | *2 |
| 1-19 | H-104 | D-116 | 11 | 45 | 6 | *2 |
| 1-20 | H-104 | D-117 | 10 | 44 | 6 | *2 |
| 1-21 | H-104 | D-118 | 8 | 40 | 4 | *2 |
| 1-22 | H-104 | D-119 | 13 | 31 | 7 | *2 |
| 1-23 | H-104 | D-120 | 14 | 34 | 6 | *2 |
| 1-24 | H-104 | D-121 | 13 | 44 | 4 | *2 |
| 1-25 | H-104 | D-122 | 11 | 34 | 4 | *2 |
| 1-26 | H-104 | D-123 | 8 | 36 | 5 | *2 |
| 1-27 | H-104 | D-124 | 7 | 41 | 4 | *2 |
| 1-28 | H-104 | D-125 | 7 | 40 | 6 | *2 |
| 1-29 | H-104 | D-126 | 10 | 30 | 6 | *2 |
| 1-30 | H-104 | D-127 | 11 | 38 | 6 | *2 |
| 1-31 | H-104 | D-128 | 9 | 44 | 9 | *2 |
| 1-32 | H-104 | D-129 | 10 | 42 | 6 | *2 |
| 1-33 | H-104 | D-130 | 14 | 39 | 6 | *2 |
| 1-34 | H-101 | D-101 | 13 | 39 | 5 | *2 |
| 1-35 | H-102 | D-101 | 7 | 45 | 6 | *2 |
| 1-36 | H-103 | D-101 | 14 | 42 | 5 | *2 |
| 1-37 | H-105 | D-101 | 10 | 36 | 5 | *2 |
| 1-38 | H-106 | D-101 | 7 | 36 | 6 | *2 |
| 1-39 | H-107 | D-101 | 6 | 44 | 6 | *2 |
| 1-40 | H-108 | D-101 | 6 | 35 | 5 | *2 |
| 1-41 | H-109 | D-101 | 7 | 36 | 5 | *2 |
| 1-42 | H-110 | D-101 | 11 | 39 | 6 | *2 |
| 1-43 | H-111 | D-101 | 8 | 36 | 6 | *2 |
| 1-44 | H-112 | D-101 | 8 | 34 | 5 | *2 |
| 1-45 | H-113 | D-101 | 6 | 43 | 5 | *2 |
| 1-46 | H-114 | D-101 | 11 | 33 | 5 | *2 |
| 1-47 | H-115 | D-101 | 12 | 49 | 5 | *2 |
| 1-48 | H-116 | D-101 | 14 | 35 | 5 | *2 |
| 1-49 | H-117 | D-101 | 14 | 32 | 5 | *2 |
| 1-50 | H-118 | D-101 | 14 | 40 | 8 | *2 |
| 1-51 | H-119 | D-101 | 11 | 40 | 6 | *2 |
| 1-52 | H-120 | D-101 | 6 | 46 | 5 | *2 |

*1: Comparative example
*2: Present invention

The results shown in Table 3 indicate that the organic EL devices 1-4 to 1-52 of the present invention undergo a smaller variation in resistance of the luminous layer and half-width of the emission spectrum, as compared to those of the organic EL devices 1-1 to 1-3 of the comparative examples. Accordingly, the present invention provides an organic EL device which barely undergoes variations in physical properties of the thin film, i.e. luminous layer.

Example 2

Another Example will now be described. In this example, the charge-transporting thin film is a luminous layer, and the functional organic compounds are a luminescent dopant and a host compound, as in Example 1.

<<Preparation of Organic EL Device 2-1>>

Indium tin oxide (ITO) with a thickness of 100 nm was deposited on a glass substrate with dimensions of 100 mm by 100 mm by 1.1 mm (NA 45 manufactured by NH Technoglass Corporation) and was patterned into an anode. A transparent support substrate provided with the transparent ITO electrode was ultrasonically cleaned in isopropyl alcohol, was dried in a dry nitrogen stream, and then was cleaned in a UV ozone environment for five minutes.

A solution of 70% poly(3,4-ethylene dioxythiophene)-polyethylenesulfonate (PEDOT/PSS; Baytron P Al 4083 available from Bayer) in pure water was applied by spin coating on the transparent support substrate at 3000 rpm for 30 seconds. The coating film was dried at 200° C. for one hour. A first hole transport layer with a thickness of 20 nm was thereby formed.

The substrate was transferred into a nitrogen atmosphere, and a solution of ADS254BE (Poly[N,N'-bis(4-butylphenyl)-N,N'-bis(phenyl)-benzidine]; manufactured by American Dye Source, Inc.) (50 mg) dissolved in 10 ml of monochlorobenzene was coated by spin coating onto the first hole transport layer at 2500 rpm for 30 seconds, and the substrate was dried at 130° C. for one hour in the vacuum. A second hole transport layer was thereby formed.

A solution of CBP (100 mg) and D-9 (13 mg) dissolved in 10 ml of butyl acetate was coated by spin coating onto the second hole transport layer at 1000 rpm for 30 seconds, and the substrate was dried at 60° C. for one hour in the vacuum. A luminous layer with a thickness of approximately 45 nm was thereby formed.

A solution of BCP (50 mg) dissolved in 10 ml of Hexafluoroisopropanol (HFIP) was coated by spin coating onto the luminous layer at 1000 rpm for 30 seconds, and the substrate was dried at 60° C. for one hour in the vacuum. An electron transport layer with a thickness of approximately 25 nm was thereby formed.

The substrate was then fixed to a substrate holder in a vacuum vapor deposition system. After evacuation of the vacuum vessel to $4\times10^{-4}$ Pa, potassium fluoride was deposited into a thickness of 0.4 nm to form a cathode buffer layer, and then aluminum was deposited into a thickness of 110 nm to form a cathode. The organic EL device 2-1 was thereby prepared.

<<Preparation of Organic EL Devices 2-2 to 2-52>>

The organic EL devices 2-2 to 2-52 were prepared as in the organic EL device 2-1, except that CBP and D-9 were replaced with the individual compounds described in Table 2.

<<Evaluation of Organic EL Devices 2-1 to 2-52>>

The resulting organic EL devices were each sealed as in the sealing of the organic EL device 1-1 in Example 1 to produce a lighting device shown in FIG. 15 or FIG. 16, and the lighting device was analyzed.

The resulting samples were subjected to evaluation of variations in resistance of the luminous layer and in half-width of the emission spectrum, as in the Example 1. Table 4 shows the variations in resistance of the luminous layer and in half-width of the emission spectrum of the organic EL devices as relative values to those (set as 100) of the organic EL device 2-1. The results are shown in Table 4.

The results shown in Table 4 indicate that the organic EL devices 2-4 to 2-52 of the present invention undergo a smaller variation in resistance of the luminous layer and in half-width of the emission spectrum, as compared to those of the organic EL devices 2-1 to 2-3 of the comparative examples. Accordingly, the present invention provides an organic EL device which barely undergoes variations in physical properties of the thin film, i.e. luminous layer.

Example 3

Another Example will now be described. In this example, the charge-transporting thin film is a luminous layer, and the functional organic compounds are a luminescent dopant and a host compound.

<<Preparation of Organic EL Device 3-1>>

Indium tin oxide (ITO) with a thickness of 100 nm was deposited on a glass substrate with dimensions of 100 mm by 100 mm by 1.1 mm (NA 45 manufactured by NH Technoglass Corporation) and was patterned into an anode. A transparent support substrate provided with the transparent ITO electrode was ultrasonically cleaned in isopropyl alcohol, was dried in a dry nitrogen stream, and then was cleaned in a UV ozone environment for five minutes.

The transparent support substrate was fixed to a substrate holder in a commercially available vacuum vapor deposition system, and 200 mg of TPD (N,N'-bis(3-methylphenyl)-N, N'-diphenyl-(1,1'-biphenyl)-4,4'-diamine) was placed onto a molybdenum resistive heating boat, 200 mg of CBP was placed onto another molybdenum resistive heating boat, 200 mg of compound D-9 was placed onto another molybdenum resistive heating boat, and 200 mg of compound D-1 was

TABLE 4

| Device No. | Host | Luminescent dopant | Variation in resistance of luminous layer (relative value) | Variation in half-width (relative value) | Total number of chiral elements | Remarks |
|---|---|---|---|---|---|---|
| 2-1 | CBP | D-9 | 100 | 100 | 1 | *1 |
| 2-2 | CBP | D-113 | 102 | 88 | 2 | *1 |
| 2-3 | H-102 | D-9 | 81 | 90 | 3 | *1 |
| 2-4 | H-102 | D-101 | 6 | 45 | 6 | *2 |
| 2-5 | H-102 | D-102 | 4 | 57 | 9 | *2 |
| 2-6 | H-102 | D-103 | 5 | 47 | 9 | *2 |
| 2-7 | H-102 | D-104 | 5 | 54 | 6 | *2 |
| 2-8 | H-102 | D-105 | 8 | 47 | 9 | *2 |
| 2-9 | H-102 | D-106 | 6 | 52 | 6 | *2 |
| 2-10 | H-102 | D-107 | 10 | 45 | 9 | *2 |
| 2-11 | H-102 | D-108 | 15 | 57 | 6 | *2 |
| 2-12 | H-102 | D-109 | 8 | 57 | 6 | *2 |
| 2-13 | H-102 | D-110 | 18 | 48 | 6 | *2 |
| 2-14 | H-102 | D-111 | 6 | 53 | 5 | *2 |
| 2-15 | H-102 | D-112 | 8 | 54 | 4 | *2 |
| 2-16 | H-102 | D-113 | 5 | 46 | 4 | *2 |
| 2-17 | H-102 | D-114 | 5 | 50 | 4 | *2 |
| 2-18 | H-102 | D-115 | 11 | 56 | 4 | *2 |
| 2-19 | H-102 | D-116 | 5 | 52 | 6 | *2 |
| 2-20 | H-102 | D-117 | 14 | 57 | 6 | *2 |
| 2-21 | H-102 | D-118 | 16 | 53 | 4 | *2 |
| 2-22 | H-102 | D-119 | 12 | 46 | 7 | *2 |
| 2-23 | H-102 | D-120 | 13 | 56 | 6 | *2 |
| 2-24 | H-102 | D-121 | 8 | 50 | 4 | *2 |
| 2-25 | H-102 | D-122 | 10 | 53 | 4 | *2 |
| 2-26 | H-102 | D-123 | 12 | 46 | 5 | *2 |
| 2-27 | H-102 | D-124 | 9 | 54 | 4 | *2 |
| 2-28 | H-102 | D-125 | 8 | 48 | 6 | *2 |
| 2-29 | H-102 | D-126 | 10 | 45 | 6 | *2 |
| 2-30 | H-102 | D-127 | 18 | 56 | 6 | *2 |
| 2-31 | H-102 | D-128 | 16 | 52 | 9 | *2 |
| 2-32 | H-102 | D-129 | 13 | 52 | 6 | *2 |
| 2-33 | H-102 | D-130 | 10 | 47 | 6 | *2 |

*1: Comparative example
*2: Present invention placed onto another molybdenum resistive heating boat, 200 mg of compound D-6 was placed onto another molybdenum resistive heating boat, and 200 mg of BCP was placed onto another molybdenum resistive heating boat. The molybdenum resistive heating boats were then placed in the vacuum vapor deposition system.

After evacuation of the vacuum vessel to $4 \times 10^{-4}$ Pa, the heating boat containing TPD was electrically heated to deposit TPD onto the transparent support substrate at a deposition rate of 0.1 nm/sec. A hole transport layer with a thickness of 10 nm was thereby formed.

The heating boats respectively containing CBP, D-9, D-1, and D-6 were electrically heated to codeposit CBP, D-9, D-1, and D-6 onto the hole transport layer at deposition rates of 0.1 nm/sec, 0.025 nm/sec, 0.0007 nm/sec, and 0.0002 nm/sec, respectively. A luminous layer with a thickness of 60 nm was thereby formed.

The heating boat containing BCP was then electrically heated to deposit BCP onto the luminous layer at a deposition rate of 0.1 nm/sec. An electron transport layer with a thickness of 20 nm was thereby formed.

Subsequently, potassium fluoride was deposited into a thickness of 0.5 nm to form a cathode buffer layer, and aluminum was deposited into a thickness of 110 nm to form a cathode. The organic EL device 3-1 was thereby prepared.

The organic EL device 3-1 thus prepared was electrically driven, and emitted substantially white light, which indicates that the device can be applied to a lighting device. An organic EL device containing other compounds exemplified above also emitted white light.

<<Preparation of Organic EL Devices 3-2 to 3-52>>

The organic EL devices 3-2 to 3-52 were prepared as in the organic EL device 3-1, except that CBP and D-9 were replaced with the compounds described in Table 5.

<<Evaluation of Organic EL Devices 3-1 to 3-52>>

The individual organic EL devices were subjected to measurement of variations in resistance of the luminous layer, as in Example 1. The results demonstrate that the measured values for the organic EL devices of the present invention are less than half of those of the comparative examples. Table 5 shows the variations in resistance of the luminous layer of the individual organic EL deices as relative values to that (set as 100) of the organic EL device 3-1.

TABLE 5

| Device No. | Host | Luminescent dopant | Variation in resistance of luminous layer (relative value) | Total number of chiral elements | Remarks |
| --- | --- | --- | --- | --- | --- |
| 3-1 | CBP | D-9 | 100 | 1 | *1 |
| 3-2 | CBP | D-111 | 96 | 3 | *1 |
| 3-3 | H-104 | D-9 | 92 | 3 | *1 |
| 3-4 | H-104 | D-101 | 15 | 6 | *2 |
| 3-5 | H-104 | D-102 | 22 | 9 | *2 |
| 3-6 | H-104 | D-103 | 17 | 9 | *2 |
| 3-7 | H-104 | D-104 | 33 | 6 | *2 |
| 3-8 | H-104 | D-105 | 22 | 9 | *2 |
| 3-9 | H-104 | D-106 | 29 | 6 | *2 |
| 3-10 | H-104 | D-107 | 26 | 9 | *2 |
| 3-11 | H-104 | D-108 | 20 | 6 | *2 |
| 3-12 | H-104 | D-109 | 31 | 6 | *2 |
| 3-13 | H-104 | D-110 | 19 | 6 | *2 |
| 3-14 | H-104 | D-111 | 26 | 5 | *2 |
| 3-15 | H-104 | D-112 | 33 | 4 | *2 |
| 3-16 | H-104 | D-113 | 26 | 4 | *2 |
| 3-17 | H-104 | D-114 | 19 | 4 | *2 |
| 3-18 | H-104 | D-115 | 39 | 4 | *2 |
| 3-19 | H-104 | D-116 | 31 | 6 | *2 |
| 3-20 | H-104 | D-117 | 25 | 6 | *2 |
| 3-21 | H-104 | D-118 | 25 | 4 | *2 |
| 3-22 | H-104 | D-119 | 22 | 7 | *2 |
| 3-23 | H-104 | D-120 | 29 | 6 | *2 |
| 3-24 | H-104 | D-121 | 17 | 4 | *2 |
| 3-25 | H-104 | D-122 | 22 | 4 | *2 |
| 3-26 | H-104 | D-123 | 28 | 5 | *2 |
| 3-27 | H-104 | D-124 | 18 | 4 | *2 |
| 3-28 | H-104 | D-125 | 30 | 6 | *2 |
| 3-29 | H-104 | D-126 | 34 | 6 | *2 |
| 3-30 | H-104 | D-127 | 22 | 6 | *2 |
| 3-31 | H-104 | D-128 | 20 | 9 | *2 |
| 3-32 | H-104 | D-129 | 19 | 6 | *2 |
| 3-33 | H-104 | D-130 | 31 | 6 | *2 |
| 3-34 | H-101 | D-101 | 35 | 5 | *2 |
| 3-35 | H-102 | D-101 | 20 | 6 | *2 |
| 3-36 | H-103 | D-101 | 23 | 5 | *2 |
| 3-37 | H-105 | D-101 | 39 | 5 | *2 |
| 3-38 | H-106 | D-101 | 32 | 6 | *2 |
| 3-39 | H-107 | D-101 | 39 | 6 | *2 |
| 3-40 | H-108 | D-101 | 25 | 5 | *2 |
| 3-41 | H-109 | D-101 | 34 | 5 | *2 |
| 3-42 | H-110 | D-101 | 25 | 6 | *2 |
| 3-43 | H-111 | D-101 | 17 | 6 | *2 |
| 3-44 | H-112 | D-101 | 16 | 5 | *2 |
| 3-45 | H-113 | D-101 | 33 | 5 | *2 |
| 3-46 | H-114 | D-101 | 32 | 5 | *2 |
| 3-47 | H-115 | D-101 | 31 | 5 | *2 |
| 3-48 | H-116 | D-101 | 27 | 5 | *2 |
| 3-49 | H-117 | D-101 | 27 | 5 | *2 |
| 3-50 | H-118 | D-101 | 26 | 8 | *2 |
| 3-51 | H-119 | D-101 | 32 | 6 | *2 |
| 3-52 | H-120 | D-101 | 24 | 5 | *2 |

*1: Comparative example
*2: Present invention

The results shown in Table 5 indicate that the organic EL devices 3-4 to 3-52 of the present invention undergo a smaller variation in resistance of the luminous layer as compared to that of the organic EL devices 3-1 to 3-3 of the comparative examples. Accordingly, the present invention provides an organic EL device which barely undergoes variations in physical properties of the thin film, i.e. luminous layer.

Example 4

Another Example will now be described. In this example, the charge-transporting thin film is a luminous layer, and the functional organic compounds are a luminescent dopant and a host compound.

<<Preparation of Organic EL Full-Color Display Device>>

FIG. 17A to FIG. 17E each show a diagrammatic view illustrating a structure of an organic EL full-color display device. Indium tin oxide (ITO) with a thickness of 100 nm (transparent ITO electrodes 202) was deposited on a glass substrate 201 (NA 45 manufactured by NH Technoglass Corporation) and was patterned into an anode at a pitch of 100 μm. Partitions 203 of non-photosensitive polyimide (each having a width of 20 μm and a thickness of 2.0 μm) were formed on the glass substrate between the transparent ITO electrodes by photolithography. The hole injection layer composition containing the components listed below was ejected from an inkjet head (MJ800C, manufactured by Seiko Epson Corporation) between the polyimide partitions on the ITO electrodes. The substrate was then dried at 200° C. for 10 minutes. A hole injection layer 204 with a thickness of 40 nm was thereby formed. The compositions for blue, green, and red luminous layers as described below were individually ejected from the inkjet head onto the hole injection layer to form the respective luminous layers (205B, 205G, and 205R). Finally, aluminum was deposited by vacuum vapor deposition to form a cathode (206) so as to cover the luminous layers 205. The organic EL device 4-1 was thereby prepared.

The organic EL device 4-2 was prepared as in the organic EL device 4-1, except that ethylene glycol monomethyl ether was replaced with 2-propylene glycol monomethyl ether and 4-isopropylbiphenyl was replaced with 4-(sec-butyl)biphenyl.

The resulting organic EL devices 4-1 and 4-2 emitted blue, green, and red light under a voltage applied to the respective electrodes, which indicates that the organic EL devices 4-1 and 4-2 can be applied to a full-color display device.

Other organic EL devices were prepared with one of compounds D-102 to D-130, instead of compound D-101. Such organic EL devices were also confirmed to be applicable to a full-color display device.

| (Hole Injection Layer Composition) Aqueous dispersion of PEDOT/PSS mixture (1.0% by mass): 20 parts by mass | |
|---|---|
| Water: | 65 parts by mass |
| Ethoxyethanol: | 10 parts by mass |
| Ethylene glycol monomethyl ether: | 5 parts by mass |
| (Composition for Blue Luminous Layer) | |
| PVK: | 0.7 parts by mass |
| Compound D-101: | 0.04 parts by mass |
| Cyclohexylbenzene: | 50 parts by mass |
| 4-isopropylbiphenyl: | 50 parts by mass |
| (Composition for Green Luminous Layer) | |
| PVK: | 0.7 parts by mass |
| D-126: | 0.04 parts by mass |
| Cyclohexylbenzene: | 50 parts by mass |
| 4-isopropylbiphenyl: | 50 parts by mass |
| (Composition for Red Luminous Layer) | |
| PVK: | 0.7 parts by mass |
| D-129: | 0.04 parts by mass |
| Cyclohexylbenzene: | 50 parts by mass |
| 4-isopropylbiphenyl: | 50 parts by mass |

<<Evaluation of Organic EL Devices 4-1 and 4-2>>

The individual organic EL devices 4-1 and 4-2 thus prepared were subjected to measurement of variations in resistance of the luminous layer, as in Example 1. The results demonstrate that the measured value of the resistance for the organic EL device 4-2 is less than half of that for the organic EL device 4-1 (the value for the organic EL device 4-2 is 42 relative to that (set as 100) for the organic EL device 4-1).

These results indicate that the organic EL full-color display device which is prepared with the organic EL device 4-2 containing a functional organic compound having chiral elements and a volatile organic material having an asymmetric carbon atom and has higher stability than that prepared with the organic EL device 4-1 which does not contain any volatile organic material having asymmetric carbon atom, although both organic EL device are included in the present invention.

Example 5

An Example will now be described. In this example, the charge-transporting thin film is an electron transport layer, and the functional organic compound is an electron transport material.

<<Preparation of Organic EL Devices 5-1 to 5-15>>

The organic EL devices 5-1 to 5-15 were prepared as in the organic EL device 1-1, except that BCP was replaced with the compounds described in Table 6.

<<Evaluation of Organic EL Devices 5-1 to 5-15>>

These organic EL devices were each sealed as in the sealing of the organic EL device 1-1 in Example 1 to produce a lighting device shown in FIG. 15 or FIG. 16, and the lighting device was evaluated.

The resulting samples were subjected to evaluation of a variation in resistance of the electron transport layer, as in the Example 1. The results are shown in Table 6.

TABLE 6

| Device No. | Electron transport material | Variation in resistance of electron transport layer (relative value) | Total number of chiral elements | Remarks |
|---|---|---|---|---|
| 5-1 | BCP | 100 | 0 | *1 |
| 5-2 | ET-102 | 72 | 2 | *1 |
| 5-3 | ET-103 | 68 | 2 | *1 |
| 5-4 | ET-101 | 37 | 4 | *2 |
| 5-5 | ET-102/ET-103 (1/1) | 17 | 4 | *2 |
| 5-6 | ET-104 | 16 | 4 | *2 |
| 5-7 | ET-105/ET-106 (1/1) | 31 | 4 | *2 |
| 5-8 | ET-107 | 20 | 4 | *2 |
| 5-9 | ET-108 | 26 | 5 | *2 |
| 5-10 | ET-109 | 34 | 4 | *2 |
| 5-11 | ET-110 | 22 | 4 | *2 |
| 5-12 | ET-111 | 28 | 4 | *2 |
| 5-13 | ET-112/ET-113 (1/1) | 19 | 6 | *2 |
| 5-14 | ET-114 | 20 | 4 | *2 |
| 5-15 | ET-115 | 26 | 6 | *2 |

*1: Comparative example
*2: Present invention

The results shown in Table 6 indicate that the organic EL devices 5-4 to 5-15 of the present invention undergo a smaller variation in resistance of the electron transport layer as compared to that of the organic EL devices 5-1 to 5-3 of the comparative examples. Accordingly, the present invention provides an organic EL device which barely undergoes variations in physical properties of the thin film, i.e. electron transport layer.

Example 6

An Example will now be described. In this example, the charge-transporting thin film is a hole transport layer, and the functional organic compound is a hole transport material.

<<Preparation of Organic EL Devices 6-1 to 6-16>>

The organic EL Devices 6-1 to 6-16 were prepared as in the organic EL Device 1-1, except that α-NPD was replaced with the compounds described in Table 7.

<<Evaluation of Organic EL Devices 6-1 to 6-16>>

The resulting organic EL devices were each sealed as in the sealing of the organic EL device 1-1 in Example 1 to produce lighting device shown in FIG. 15 or FIG. 16, and the lighting device was evaluated.

The resulting samples were subjected to evaluation of a variation in resistance of the hole transport layer, as in the Example 1. The results are shown in Table 7.

TABLE 7

| Device No. | Hole transport material | Variation in resistance of hole transport layer (relative value) | Total number of chiral elements | Remarks |
|---|---|---|---|---|
| 6-1 | α-NPD | 100 | 0 | *1 |
| 6-2 | HT-102 | 88 | 2 | *1 |
| 6-3 | HT-104 | 63 | 2 | *1 |
| 6-4 | HT-101 | 25 | 4 | *2 |
| 6-5 | HT-102/HT-104 (1/1) | 30 | 4 | *2 |
| 6-6 | HT-103 | 27 | 5 | *2 |
| 6-7 | HT-105 | 37 | 5 | *2 |
| 6-8 | HT-106 | 34 | 4 | *2 |
| 6-9 | HT-107/HT-108 (1/1) | 39 | 6 | *2 |
| 6-10 | HT-108 | 12 | 4 | *2 |
| 6-11 | HT-109 | 36 | 4 | *2 |
| 6-12 | HT-110 | 10 | 4 | *2 |
| 6-13 | HT-111/HT-112 (1/1) | 20 | 4 | *2 |
| 6-14 | HT-113/HT-114 (1/1) | 32 | 8 | *2 |
| 6-15 | HT-115 | 29 | 4 | *2 |
| 6-16 | HT-116 | 18 | 4 | *2 |

*1: Comparative example
*2: Present invention

The results shown in Table 7 indicate that the organic EL devices 6-4 to 6-16 of the present invention undergo a smaller variation in resistance of the hole transport layer as compared to that of the organic EL devices 6-1 to 6-3 of the comparative examples. Accordingly, the present invention provides an organic EL device which barely undergoes variations in physical properties of the thin film, i.e. hole transport layer.

Example 7

<<Preparation of Organic Photoelectric Device>>

An Example will now be described. In this example, the charge-transporting thin film is a photoelectric layer, and the functional organic compound is selected from compounds C-101 to C-104.

<<Preparation of Organic Photoelectric Device 7-1>>

Indium tin oxide (ITO) with a thickness of 140 nm was deposited on a glass substrate to form a transparent ITO electrically conductive film, and was patterned at a pitch of 2 mm by a normal photolithographic technique and etching with hydrochloric acid. A transparent electrode was thereby prepared.

The patterned transparent electrode was ultrasonically cleaned in a surfactant and ultrapure water, then was ultrasonically cleaned in ultrapure water, and then was dried under a nitrogen stream. The transparent electrode was finally cleaned in a UV-ozone environment. An electrically conductive polymer Baytron P4083 (available from H. C. Starck-V Tech, Ltd.) was coated onto the transparent substrate by spin coating in a thickness of 60 nm. The transparent substrate was then dried in the air at 140° C. for 10 minutes.

The substrate was then placed in a glovebox for subsequent processes in a nitrogen atmosphere. In the first stage, the substrate was heated at 140° C. for 10 minutes in the nitrogen atmosphere.

A solution was prepared by dissolving 1.0 mass % PCP-DTBT (polythiophene copolymer described in Nature Mat. vol. 6 (2007) on page 497) as a p-type semiconductor material, 2.0 mass % PCBM (NANOM SPECTRA E100H, available from Frontier Carbon Corporation) as an n-type semiconductor material, and 2.4 mass % 1,8-octanedithiol in chlorobenzene. The solution was coated by spin coating at 1200 rpm for 60 seconds, while the solution was filtered with a filter having a pore size of 0.45 µm. The substrate was then dried at room temperature for 30 minutes. A photoelectric layer was thereby formed.

The substrate provided with the organic functional layers was placed in a vacuum vapor deposition system such that a shadow mask with a pitch of 2 mm was perpendicular to the transparent electrode. After evacuation of the vacuum vapor deposition system to $10^{-3}$ Pa or lower, lithium fluoride and aluminum were deposited into thicknesses of 0.5 nm and 80 nm, respectively. The resulting laminate was finally heated at 120° C. for 30 minutes. An organic photoelectric device 1 of the comparative example was thereby prepared. In each deposition process, the layer was formed at a deposition rate of 2 nm/sec and into a size of 2 mm square.

The resulting organic photoelectric device 1 was sealed with an aluminum cap and a UV-curable resin (UV RESIN XNR5570-B1, available from Nagase Chemtex Corporation) in a nitrogen atmosphere. The organic photoelectric device 7-1 was thereby prepared.

The organic photoelectric devices 7-2 to 7-5 were prepared as in the organic photoelectric device 7-1, except that PCBM was replaced with the compounds described in Table 8.

<<Evaluation of Organic Photoelectric Devices 7-1 to 7-5>>

The resulting organic photoelectric devices were irradiated with light with an intensity of 100 mW/cm$^2$ emitted from a solar simulator (with AM 1.5 G filter) for 1000 hours. The devices after the irradiation were subjected to measurement of variations in resistance of the organic functional layers containing the functional organic compound of the present invention as in Example 1. The results shown in Table 8 indicate that the organic photoelectric device of the present invention had significantly lower values than the comparative example.

TABLE 8

| Device No. | Compound in organic functional layer | Variation in resistance (relative value) | Total number of chiral elements | Remarks |
|---|---|---|---|---|
| 7-1 | PCBM | 100 | 0 | *1 |
| 7-2 | C-101 | 33 | 4 | *2 |
| 7-3 | C-102 | 36 | 5 | *2 |
| 7-4 | C-103 | 17 | 5 | *2 |
| 7-5 | C-104 | 13 | 5 | *2 |

*1: Comparative example
*2: Present invention

Example 8

An Example will now be described. In this example, the charge-transporting thin film is a photosensitive layer, and the functional organic compound is selected from compounds C-201 to C-205.

<<Preparation of Dye-Sensitized Solar Cell>>
<<Preparation of Photoelectric Device R1>>

Figure 18:
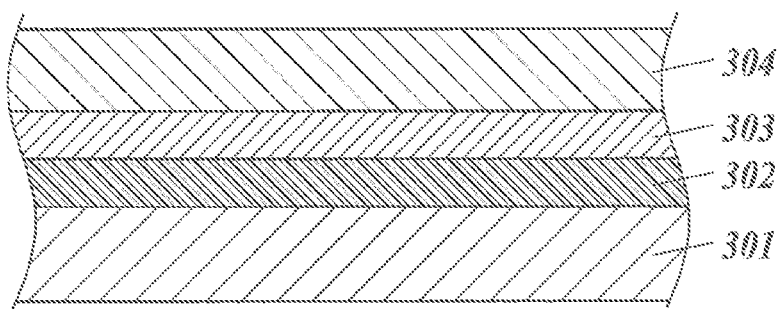
FIG. 18 is a partial cross-sectional view illustrating an exemplary structure of a photoelectric device.

The photoelectric device as shown in FIG. 18 was prepared as follows.

To 375 ml of pure water, 62.5 ml of titanium tetraisopropoxide (first grade, available from Wako Pure Chemical Industries, Ltd.) was added dropwise at room temperature for 10 minutes under vigorous stirring (so that white precipitates were produced). To the resultant solution, 2.65 ml of 70% aqueous nitric acid solution was added. After the reaction system was heated to 80° C., the mixture was continuously stirred for eight hours. The reaction mixture was concentrated under reduced pressure to a volume of approximately 200 ml, and then 125 ml of pure water and 140 g of titanium oxide powder (SUPER-TITANIA F-6, available from Showa Titanium Co., Ltd.) were added to the concentrated mixture to prepare titanium oxide suspension (approximately 800 ml). The titanium oxide suspension was applied onto a transparent electrically conductive glass substrate coated with fluorine-doped tin oxide. The substrate was spontaneously dried, and then was calcined at 300° C. for 60 minutes to form a titanium oxide film on the support.

A solution was then prepared by dissolving 5 g of the compound R1 in 200 ml of methanol solution. The support with the titanium oxide film (semiconductor layer for photoelectric material) was immersed in the resulting solution, and 1 g of trifluoroacetic acid was added. The support was then subjected to insonation for two hours. After the reaction, the titanium oxide film (semiconductor layer for photoelectric material) was cleaned in chloroform, and then was dried in the vacuum. A photosensitive layer 302 (semiconductor for photoelectric material) was thereby prepared.

Fluorine-doped titanium oxide was coated onto a transparent electrically conductive glass substrate, and then platinum was coated onto the fluorine-doped titanium oxide to form a counter electrode 304. A redox electrolyte was prepared by dissolving tetrapropylammonium iodide and iodine in a mixed solvent of acetonitrile and ethylene carbonate at a volume ratio of 1:4, so that the tetrapropylammonium iodide and iodine were contained at concentrations of 0.46 mol/l and 0.06 mol/l, respectively. The redox electrolyte was injected into a space between the electrically conductive support 301 and the counter electrode 304 to form a charge transfer layer 303. The photoelectric device R1 was thereby prepared.

<<Preparation of Solar Cell 8-1>>

The sides of the photoelectric device R1 were sealed with a resin, and the device was provided with lead. The solar cell 8-1 of the comparative example was thereby prepared.

The dye-sensitized solar cells 8-2 to 8-6 were prepared as in the dye-sensitized solar cell 8-1, except that the compound R1 was replaced with the individual compounds described in Table 9.

<<Evaluation of Dye-Sensitized Solar Cells 8-1 to 8-6>>

The resulting organic photoelectric devices were irradiated with light with an intensity of 100 mW/cm² emitted from a solar simulator (with AM 1.5 G filter) for 1000 hours. The devices after the irradiation were subjected to measurement of variations in resistance of the organic functional layers containing the functional organic compound of the present invention as in Example 1. The results shown in Table 9 indicate that the dye-sensitized solar cell of the present invention had significantly lower values than that of the comparative example.

TABLE 9

| Solar cell No. | Compound in organic functional layer | Variation in resistance (relative value) | Total number of chiral elements | Remarks |
| --- | --- | --- | --- | --- |
| 8-1 | R1 | 100 | 1 | *1 |
| 8-2 | C-201 | 37 | 4 | *2 |
| 8-3 | C-202 | 18 | 5 | *2 |
| 8-4 | C-203 | 31 | 4 | *2 |

TABLE 9-continued

| Solar cell No. | Compound in organic functional layer | Variation in resistance (relative value) | Total number of chiral elements | Remarks |
| --- | --- | --- | --- | --- |
| 8-5 | C-204 | 34 | 4 | *2 |
| 8-6 | C-205 | 23 | 4 | *2 |

*1: Comparative example
*2: Present invention

Example 9

An Example will now be described. In this example, the charge-transporting thin film is a luminous layer, and the functional organic compound is selected from compounds F-101 to F-118.

<<Preparation of Organic EL Devices 9-1 to 9-18>>

The organic EL devices 9-1 to 9-18 were prepared as in the organic EL device 1-1, except that D-9 was replaced with the individual compounds described in Table 10.

<<Evaluation of Organic EL Devices 9-1 to 9-18>>

The organic EL devices were each sealed as in the sealing of the organic EL device 1-1 in Example 1 to produce lighting device shown in FIG. 15 or FIG. 16, and the lighting device was analyzed.

The individual samples thus prepared were subjected to evaluation of a variation in resistance of the luminous layer, as in the Example 1. The results are shown in Table 10.

TABLE 10

| Device No. | Compound in organic functional layer | Variation in resistance (relative value) | Total number of chiral elements | Remarks |
| --- | --- | --- | --- | --- |
| 9-1 | D-9 | 100 | 1 | *1 |
| 9-2 | F-01 | 96 | 0 | *1 |
| 9-3 | F-101 | 72 | 2 | *1 |
| 9-4 | F-102 | 81 | 2 | *1 |
| 9-5 | F-101/F-102 (1/1) | 41 | 4 | *2 |
| 9-6 | F-103/F-104 (1/1) | 22 | 4 | *2 |
| 9-7 | F-105/F-106 (1/1) | 24 | 5 | *2 |
| 9-8 | F-107 | 32 | 5 | *2 |
| 9-9 | F-108 | 22 | 4 | *2 |
| 9-10 | F-109 | 37 | 4 | *2 |
| 9-11 | F-110 | 29 | 4 | *2 |
| 9-12 | F-111/F-112 (1/1) | 37 | 4 | *2 |
| 9-13 | F-113/F-114 (1/1) | 25 | 8 | *2 |
| 9-14 | F-114 | 13 | 4 | *2 |
| 9-15 | F-115 | 40 | 4 | *2 |
| 9-16 | F-116 | 46 | 4 | *2 |
| 9-17 | F-117 | 27 | 4 | *2 |
| 9-18 | F-118 | 40 | 4 | *2 |

*1: Comparative example
*2: Present invention

The results shown in Table 10 indicate that the organic EL devices 9-5 to 9-18 of the present invention undergo a smaller variation in resistance of the luminous layer as compared to that of the organic EL devices 9-1 to 9-4 of the comparative examples. Accordingly, the present invention provides an organic EL device which barely undergoes variations in physical properties of the thin film, i.e. luminous layer.

As described above, each Example demonstrates that use of an increased number of components without changing the energy level can reduce variations in the state of the charge-transporting thin film due to disturbance.

According to the present invention, changes in state of a charge transfer film can be compared based on resistance as indicator of the changes occurring in actual devices, by applying a novel nondestructive measurement called impedance spectroscopy. Although this is a novel method and the extent of errors in measured values cannot be specified, a charge-transporting thin film composed of a composition containing a mixture of enantiomers and diastereomers having multiple chiral elements according to the technical idea of the present invention undergoes a significantly smaller variation in resistance than that in comparative charge-transporting thin films. Thus, this method is believed to appropriately indicate the changes occurring in actual devices and to be valid.

In organic EL devices and organic thin-film solar cells having a charge-transporting thin film, the short lifetime of the device is an issue which is an obstacle to practical use. In an extreme argument, the lifetime of the device entirely depends on a variation in resistance of a charge-transporting thin film in the device. Variations in resistance can be quantitatively evaluated from multiple correlation of various factors, including degradation of compounds, a change in a state of aggregation, changes in a shape or size of crystal grains, and a change in the presence (interaction) of different molecules. Application of impedance spectroscopy allows nondestructive detection of a variation in resistance only for any specific film among multiple layers in an actual device after preparation, and is advantageous in identifying a substance or position that causes the undesired variation, unlike in conventional evaluation of the lifetime of the device. The present invention is therefore effective to take specific measures for improving device performance.

The present invention is also significant from academic viewpoints. Compounds having chiral elements are normally applied to human, animals and plants, and higher enantiomeric excess and diastereomeric excess are preferred. Researchers who study on synthesis of such compounds have made great efforts in isolation (increasing purity) of a single compound. Meanwhile, in the technique of the present invention, enantiomers and diastereomer do not work if they are present as a single substance, and the presence of various types of isomers increases the degree of disorder, which increases stability of a film just after formation. Thus, the present invention is characterized by effectiveness and value entirely contrary to conventional theories in chemistry of chiral compounds.

Various mixtures have been used in a charge-transporting thin film, particularly in a film formed by a coating process, for easy preparation of components. Unfortunately, if the components have different energy levels, charges concentrate on a material with the deepest energy level. Thus, even if the conventional methods have entropic effects as in the present invention, they rather cause undesired load on a specific material and no significant improvement in film stability has been actually observed.

One of the characteristics of the present invention is great easiness in synthesis of isomers from viewpoints of synthetic chemistry, in that many types of enantiomers and diastereomers, i.e. isomers having very similar physico-chemical characteristics, can be synthesized simultaneously, without use of chiral sources which are used for increasing enantiomeric excess or diastereomeric excess.

According to the present invention, single or combined use of compounds having multiple chiral elements per molecule prevents charge concentration and provides a fundamentally robust charge-transporting thin film, that is, increases robustness of the film against disturbance, such as electric current, heat, and light, based on entropic effects due to an increase in the number of components. In view of this, the inventors have found a revolutionary technique. The inventors also believe that the invention is an advanced technique which supports future development in organic electronics and which can be applied to general use, because the technical idea of the invention can be universally applied to any charge-transfer or electrically conductive film or article, in addition to the applications described herein in the Examples.

INDUSTRIAL APPLICABILITY

The electronic device of the present invention undergoes small variations in characteristics due to disturbance and small variations in resistance during application of current, and can be suitably applied to organic electroluminescent devices, electrically conductive films, organic thin-film solar cells, and dye-sensitized solar cells.

EXPLANATION OF REFERENCE NUMERALS

1 organic semiconductor layer
2 source electrode
3 drain electrode
4 gate electrode
5 insulation layer
6 support
7 gate bus line
8 source bus line
10 organic TFT sheet
11 organic TFTs
12 output device
13 storage capacitor
14 vertical drive circuit
15 horizontal drive circuit
101 organic EL device
102 glass case
105 cathode
106 organic EL layer
107 glass substrate with a transparent electrode
108 nitrogen gas
109 water-trapping agent
201 glass substrate
202 ITO transparent electrode
203 partitions
204 hole injection layer
205B, 205G, 205R luminous layers
206 cathode
301 electrically conductive support
302 photosensitive layer
303 charge transfer layer
304 counter electrode
A component A
B component B

The invention claimed is:
1. An electronic device comprising a charge-transporting thin film containing at least two types of functional organic compounds having chiral elements,
   wherein the total number of chiral elements per molecule in each type of the functional organic compounds, summed over all the functional organic compounds, is four or more,
   at least one of the functional organic compounds is a metal complex, the metal complex has two or more chiral elements per molecule, and thereby comprises a mixture of enantiomers and diastereomers, and at least one of the functional organic compounds is a host compound and comprises a mixture of enantiomers and diastereomers.

2. The electronic device according to claim 1, wherein the total number of chiral elements per molecule, summed over all the functional organic compounds, is within a range of five to fifteen.

3. The electronic device according to claim 1, wherein each of the at least two types of the functional organic compounds, which are other than the metal complex and the host compound, comprises at least one selected from a mixture of enantiomers and a mixture of diastereomers.

4. The electronic device according to claim 1, wherein all of the at least two types of the functional organic compounds comprise a mixture of enantiomers and diastereomers.

5. The electronic device according to claim 1, wherein at least one of the functional organic compounds having chiral elements have a biaryl structure which has chiral elements due to hindered rotation between two aryl moieties, such that the at least one of the functional organic compounds comprises a mixture of atropisomers.

6. The electronic device according to claim 1, wherein the at least one type of the functional organic compounds having chiral elements is a compound which emits light during excitation under an electric field.

7. The electronic device according to claim 6, wherein the compound which emits light during excitation under an electric field is the metal complex.

8. An electroluminescent element which is the electronic device according to claim 1.

9. An electrically conductive film which is the electronic device according to claim 1.

10. An organic thin-film solar cell which is the electronic device according to claim 1.

11. A dye-sensitized solar cell which is the electronic device according to claim 1.

12. The electronic device according to claim 1, wherein all of the at least two types of the functional organic compounds having chiral elements have a biaryl structure which has chiral elements due to hindered rotation between two aryl moieties, such that all of the at least two types of the functional organic compounds comprise a mixture of atropisomers.

13. An electronic device comprising a charge-transporting thin film containing one or more types of functional organic compounds having chiral elements, wherein the total number of chiral elements per molecule in each type of the functional organic compounds, summed over all the functional organic compounds, is four or more, the charge-transporting thin film contains the functional organic compounds having chiral elements; and the thin film further comprises a volatile organic material having a boiling point lower than 300° C. under normal pressure, wherein the volatile organic material has an asymmetric carbon atom.

14. The electronic device according to claim 1, wherein the charge-transporting thin film contains the functional organic compounds having chiral elements; and the thin film further comprises a volatile organic material having a boiling point lower than 300° C. under normal pressure, wherein the volatile organic material has an asymmetric carbon atom.

15. The electronic device according to claim 10, wherein the volatile organic material comprises at least one selected from the group consisting of a substituted aliphatic hydrocarbon solvent having an asymmetric carbon atom, a substituted aromatic hydrocarbon solvent having an asymmetric carbon atom, and a substituted halogen solvent having an asymmetric carbon atom.

16. The electronic device according to claim 10, wherein the volatile organic material comprises at least one selected from the group consisting of 2-ethylhexane, sec-butyl ether, 2-pentanol, 2-methyltetrahydrofuran, 2-propylene glycol monomethyl ether, 2,3-dimethyl-1,4-dioxane, sec-butylbenzene, 4-(sec-butyl)biphenyl, and 2-methylcyclohexylbenzene.

* * * * *